United States Patent
Sato et al.

(10) Patent No.: US 6,869,966 B2
(45) Date of Patent: Mar. 22, 2005

(54) N-SUBSTITUTED-2-OXODIHYDROPYRIDINE DERIVATIVES

(75) Inventors: Nagaaki Sato, Tsukuba (JP); Makoto Ando, Tsukuba (JP); Shiho Ishikawa, Tsukuba (JP); Tsuyoshi Nagase, Tsukuba (JP); Keita Nagai, Tsukuba (JP); Akio Kanatani, Tsukuba (JP)

(73) Assignee: Banyu Pharmaceutical Co., Ltd., Tokyo (JP)

( * ) Notice: Subject to any disclaimer, the term of this patent is extended or adjusted under 35 U.S.C. 154(b) by 88 days.

(21) Appl. No.: 10/641,017

(22) Filed: Aug. 15, 2003

(65) Prior Publication Data

US 2004/0072874 A1 Apr. 15, 2004

(30) Foreign Application Priority Data

Sep. 30, 2002  (JP) ........................................ 2002-287015
Dec. 5, 2002   (JP) ........................................ 2002-353202

(51) Int. Cl.⁷ .................... C07D 401/02; C07D 213/02; A61K 31/44
(52) U.S. Cl. .................... 514/333; 514/397; 546/256; 546/274.1
(58) Field of Search .............................. 546/274.1, 256; 514/396, 333

(56) References Cited

FOREIGN PATENT DOCUMENTS

| EP | 1 264 826 | 12/2002 |
| WO | 99/48888 | 9/1999 |
| WO | 01/62738 | 8/2001 |

OTHER PUBLICATIONS

Database Crossfire Beilstein Online! Beilstein Institut zur Föderung der Chemischen Wissenschaften, Frankfurt am Main, DE; XP002265820. Database accession No. 150480 abstract.

*Primary Examiner*—Zinna Northington Davis
(74) *Attorney, Agent, or Firm*—Wenderoth, Lind & Ponack, L.L.P.

(57) ABSTRACT

A compound of the formula (I):

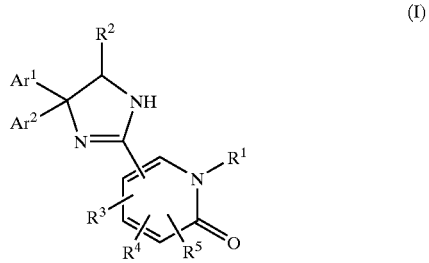

(wherein $Ar^1$ and $Ar^2$ are independently aryl or heteroaryl, any of which is optionally substituted by a substituent selected from the group consisting of cyano, halogen, nitro, lower alkyl, halo-lower alkyl, hydroxy-lower alkyl, cyclo-lower alkyl, cyclo(lower alkyl)-lower alkyl, lower alkenyl, lower alkylamino, di-lower alkylamino, lower alkanoylamino, lower alkylsulfonylamino, arylsulfonylamino, hydroxy, lower alkoxy, halo-lower alkoxy, aryloxy, heteroaryloxy, lower alkylthio, carboxyl, formyl, lower alkanoyl, lower alkoxycarbonyl, carbamoyl, lower alkylcarbamoyl, di-lower alkylcarbamoyl, lower alkylsulfonyl, arylsulfonyl, aryl and heteroaryl;

$R^1$ and $R^2$ are independently lower alkyl, cyclo-lower alkyl, cyclo(lower alkyl)-lower alkyl or lower alkoxy, any of which is optionally substituted by a substituent selected from the group consisting of halogen, lower alkylamino, di-lower alkylamino, lower alkanoylamino, hydroxy, lower alkoxy, formyl, lower alkoxycarbonyl, lower alkylcarbamoyl and di-lower alkylcarbamoyl;

$R^3$, $R^4$ and $R^5$ are independently hydrogen, cyano, halogen or hydroxy, or lower alkyl, lower alkoxy or lower alkylthio, the last three groups being optionally substituted by a substituent selected from the group consisting of halogen, lower alkylamino, di-lower alkylamino, lower alkanoylamino, hydroxy, lower alkoxy, formyl, lower alkoxycarbonyl, lower alkylcarbamoyl and di-lower alkylcarbamoyl), or a salt or ester thereof is useful as a neuropeptide Y receptor antagonist agent and is also useful as an agent for the treatment of bulimia, obesity or diabetes.

41 Claims, No Drawings

N-SUBSTITUTED-2-OXODIHYDROPYRIDINE DERIVATIVES

TECHNICAL FIELD

The present invention is useful in medical fields. In more detail, N-substituted-2-oxodihydropyridine derivatives of the present invention have an effect as neuropeptide Y receptor antagonists and are useful as agents for the treatment of various kinds of cardiovascular disorders, nervous system disorders, metabolic diseases, genital or reproductive disorders, gastro-intestinal disorders, respiratory disorders, inflammatory diseases or glaucoma, and the like.

BACKGROUND ART

Neuropeptide Y (hereinafter referred to as NPY), a peptide consisting of 36 amino acids, was first isolated from porcine brain by Tatemoto et al in 1982 (NATURE, vol. 296, p. 659(1982)). NPY is widely distributed in central nervous system and peripheral nervous system, and plays various roles as one of the most abundant peptides in the nervous system. That is, NPY acts as an orexigenic substance in the central nervous system and markedly promotes fat accumulation via the mediation of secretion of various hormones or the action of the nervous system. It is known that continuous intracerebroventricular administration of NPY induces obesity and insulin resistance due to these actions (INTERNATIONAL JOURNAL OF OBESITY, vol. 19, p. 517(1995); Endocrinology, vol. 133, p. 1753(1993)). It is also known that NPY has central actions such as depression, anxiety, schizophrenia, pain, dementia, circadian rhythm control and the like (DRUGS, vol. 52, p. 371(1996); THE JOURNAL OF NEUROSCIENCE, vol. 18, p. 3014(1998)). Furthermore, in the periphery, NPY coexists with norepinephrine in sympathetic-nerve terminals and is related to the tonicity of the sympathetic nervous system. It is known that peripheral administration of NPY causes vasoconstriction and enhances the activities of other vasoconstrictive substances such as norepinephrine (BRITISH JOURNAL OF PHARMACOLOGY, vol. 95, p. 419(1988)). It is also reported that NPY could participate in the development of cardiac hypertrophy as a result of the sympathetic stimulation (PROCEEDINGS OF THE NATIONAL ACADEMY OF SCIENCES OF THE UNITED STATES OF AMERICA, vol. 97, p. 1595(2000)).

On the other hand, it is reported that NPY is also involved in the secretory function of sexual hormones and growth hormone, sexual behavior and reproductive function, gastro-intestinal motility, bronchoconstriction, inflammation and alcohol preference (LIFE SCIENCE, vol. 55, p. 551(1994); THE JOURNAL OF ALLERGY AND CLINICAL IMMUNOLOGY, vol. 101, p. S345(1998); NATURE, vol. 396, p. 366(1998)).

NPY has a variety of pharmacological effects resulting from NPY binding to some NPY receptors to which peptide YY and pancreatic polypeptide, which are the analogs of NPY, also bind. It is known that these pharmacological effects of NPY are mediated by the action of at least five receptors with or without synergistic interactions (TRENDS IN NEUROSCIENCES, vol. 20, p. 294(1997)).

It is reported that the central effects mediated by NPY Y1 receptor include remarkable orexigenic effect (ENDOCRINOLOGY, vol. 137, p. 3177(1996); ENDOCRINOLOGY, vol. 141, p. 1011(2000)). Further, NPY Y1 receptor is reported to be involved in anxiety and pain (NATURE, vol. 259, p. 528(1993); BRAIN RESEARCH, vol. 859, p. 361(2000). In addition, the pressor effect mediated by the strong vasoconstrictor action in the periphery is also reported (FEBS LETTERS, vol. 362, p. 192(1995); NATURE MEDICINE, vol. 4, p. 722(1998)).

It is known that the effects mediated by NPY Y2 receptor include an inhibitory effect on the release of various neurotransmitters in the sympathetic nerve endings (BRITISH JOURNAL OF PHARMACOLOGY, vol. 102, p. 41(1991); SYNAPSE, vol. 2, p. 299(1988)). In periphery, NPY Y2causes constriction of blood vessel or vas deferens directly or via the control of release of various neurotransmitters (THE JOURNAL OF PHARMACOLOGY AND EXPERIMENTAL THERAPEUTICS, vol. 261, p. 863 (1992); BRITISH JOURNAL OF PHARMACOLOGY, vol. 100, p. 190(1990)). Inhibition of lipolysis in adipose tissues is also known (ENDOCRINOLOGY, vol. 131, p. 1970 (1992)). Further, inhibition of ion secretion in the gastro-intestinal tract is reported (BRITISH JOURNAL OF PHARMACOLOGY, vol. 101, p. 247(1990)). On the other hand, the effects on the central nervous system functions such as memory, anxiety and the like are also known (BRAIN RESEARCH, vol. 503, p. 73(1989); PEPTIDES, vol. 19, p. 359(1998)).

It is reported that NPY Y3 receptor exists mainly in brainstem and heart, and is related to the regulation of blood pressure and heart rate (THE JOURNAL OF PHARMACOLOGY AND EXPERIMENTAL THERAPEUTICS, vol. 258, p. 633(1991); PEPTIDES, vol. 11, p. 545(1990)). It is also known that NPY Y3 is involved in the control of catecholamine secretion in adrenal gland (THE JOURNAL OF PHARMACOLOGY AND EXPERIMENTAL THERAPEUTICS, vol. 244, p. 468(1988); LIFE SCIENCE, vol. 50, p. PL7(1992)).

NPY Y4 receptor has high affinity for pancreatic polypeptide in particular. As for the pharmacological effects of NPY Y4, inhibition of pancreatic exocrine secretion and gastro-intestinal motility is reported (GASTROENTEROLOGY, vol. 85, p. 1411(1983)). Further, it is reported that NPY enhances the secretion of sexual hormones in the central nervous system (ENDOCRINOLOGY, vol. 140, p. 5171 (1999)).

As for the effects mediated by NPY Y5 receptor, fat accumulation effects including orexigenic effect are prominent (NATURE, vol. 382, p. 168(1996); AMERICAN JOURNAL OF PHYSIOLOGY, vol. 277, p. R1428(1999)). It is also reported that the NPY Y5 receptor mediates some CNS effects, such as seizure and epilepsy, or pain and morphine withdrawal symptoms, and the control of circadian rhythm (NATURE MEDICINE, vol. 3, p. 761(1997); PROCEEDINGS OF THE NATIONAL ACADEMY OF SCIENCES OF THE UNITED STATES OF AMERICA, vol. 96, p. 13518(1999); THE JOURNAL OF PHARMACOLOGY AND EXPERIMENTAL THERAPEUTICS, vol. 284, p. 633(1998); THE JOURNAL OF NEUROSCIENCE, vol. 21, p. 5367(2001). In addition, diuretic effect and hypoglicemic effect in the periphery are reported (BRITISH JOURNAL OF PHARMACOLOGY, vol. 120, p. 1335 (1998); ENDOCRINOLOGY, vol. 139, p. 3018(1998)). NPY is also reported to enhance cardiac hypertrophy as a result of the sympathetic accentuation (PROCEEDINGS OF THE NATIONAL ACADEMY OF SCIENCES OF THE UNITED STATES OF AMERICA, vol. 97, p. 1595 (2000)).

The effects of NPY are expressed when NPY binds to the NPY receptors in the central or peripheral nervous system. Therefore, the action of NPY can be prevented by blocking its binding to NPY receptors. For this reason, it is expected that substances antagonize NPY binding to NPY receptors may be useful for the prophylaxis or treatment of various diseases related to NPY, for example cardiovascular disorders such as angina, acute or congestive heart failure, myocardial infarction, hypertension, nephropathy, electrolyte abnormality, vasospasm, etc., central nervous system disorders such as bulimia, depression, anxiety, seizure, epilepsy, dementia, pain, alcoholism, drug withdrawal, circadian rhythm disorders, schizophrenia, memory impairment, sleep disorders, cognitive impairment, etc., metabolic diseases such as obesity, diabetes, hormone abnormality, gout, fatty liver, etc., genital or reproductive disorders such as infertility, preterm labor, sexual dysfunction, etc., gastro-intestinal disorders, respiratory disorders, inflammatory diseases or glaucoma, and the like. (TRENDS IN PHARMACOLOGICAL SCIENCES, vol. 15, p. 153(1994); LIFE SCIENCE, vol. 55, p. 551(1994); DRUGS, vol. 52, p. 371(1996); THE JOURNAL OF ALLERGY AND CLINICAL IMMUNOLOGY, vol. 101, p. S345(1998); NATURE, vol. 396, p. 366(1998); THE JOURNAL OF PHARMACOLOGY AND EXPERIMENTAL THERAPEUTICS, vol. 284, p. 633(1998); TRENDS IN PHARMACOLOGICAL SCIENCES, vol. 20, p. 104(1999); PROCEEDINGS OF THE NATIONAL ACADEMY OF SCIENCES OF THE UNITED STATES OF AMERICA, vol. 97, p. 1595(2000); THE JOURNAL OF NEUROSCIENCE, vol. 21, p. 5367(2001); PHARMACOLOGY & THERAPEUTICS, vol. 65, p 397(1995); ENDOCRINOLOGY, vol. 140, p. 4046(1999); AMERICAN JOURNAL OF PHYSIOLOGY, vol. 280, p. R1061 (2001); AMERICAN JOURNAL OF PHYSIOLOGY, vol. 278, p. R1627(2000); CURRENT OPINION IN CLINICAL NUTRITION AND METABOLIC CARE, vol. 2, p. 425 (1999); CURRENT RHEUMATOLOGY REPORTS, vol. 3, p. 101(2001), AMERICAN JOURNAL OF RESPIRATORY AND CRITICAL CARE MEDICINE, vol. 165, p. 1217 (2002).

It was recently found that, as a result of the study by the present inventors, certain NPY receptor antagonists are useful for the prophylaxis or treatment of hypercholesterolemia, hyperlipidemia and arteriosclerosis (International application publication WO99/27965).

International application publication WO01/62738 discloses a variety of imidazoline derivatives, and mentions that the derivatives have excellent NPY receptor antagonistic actions and also show excellent pharmacokinetics such as transport into brain or transport to cerebrospinal fluid, etc. However, the said literature does not describe the compounds of the present invention.

DISCLOSURE OF INVENTION

The object of the present invention is to provide novel medicines which have NPY antagonistic actions.

The present inventors have discovered that the compounds of the formula (I):

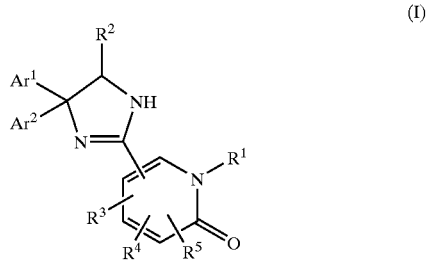

(wherein $Ar^1$ and $Ar^2$ are independently aryl or heteroaryl, any of which is optionally substituted by a substituent selected from the group consisting of cyano, halogen, nitro, lower alkyl, halo-lower alkyl, hydroxy-lower alkyl, cyclo-lower alkyl, cyclo(lower alkyl)-lower alkyl, lower alkenyl, lower alkylamino, di-lower alkylamino, lower alkanoylamino, lower alkylsulfonylamino, arylsulfonylamino, hydroxy, lower alkoxy, halo-lower alkoxy, aryloxy, heteroaryloxy, lower alkylthio, carboxyl, formyl, lower alkanoyl, lower alkoxycarbonyl, carbamoyl, lower alkylcarbamoyl, di-lower alkylcarbamoyl, lower alkylsulfonyl, arylsulfonyl, aryl and heteroaryl;

$R^1$ and $R^2$ are independently lower alkyl, cyclo-lower alkyl, cyclo(lower alkyl)-lower alkyl or lower alkoxy, any of which is optionally substituted by a substituent selected from the group consisting of halogen, lower alkylamino, di-lower alkylamino, lower alkanoylamino, hydroxy, lower alkoxy, formyl, lower alkoxycarbonyl, lower alkylcarbamoyl and di-lower alkylcarbamoyl;

$R^3$, $R^4$ and $R^5$ are independently hydrogen, cyano, halogen or hydroxy, or lower alkyl, lower alkoxy or lower alkylthio, the last three groups being optionally substituted by a substituent selected from the group consisting of halogen, lower alkylamino, di-lower alkylamino, lower alkanoylamino, hydroxy, lower alkoxy, formyl, lower alkoxycarbonyl, lower alkylcarbamoyl and di-lower alkylcarbamoyl) have NPY antagonistic actions especially on NPY Y5 receptors, show excellent pharmacokinetics such as transport into brain or transport to cerebrospinal fluid, etc., and are also very safe, thereby completed the present invention.

The compounds of the present invention (I) have NPY antagonistic actions especially on NPY Y5 receptors, show excellent pharmacokinetics such as transport into brain or transport to cerebrospinal fluid, etc., and are very safe, thus they are useful as agents for the treatment of various diseases related to NPY, for example, cardiovascular disorders such as angina, acute or congestive heart failure, myocardial infarction, hypertension, nephropathy, electrolyte abnormality, vasospasm, arteriosclerosis, etc., central nervous system disorders such as bulimia, depression, anxiety, seizure, epilepsy, dementia, pain, alcoholism, drug withdrawal, circadian rhythm disorders, schizophrenia, memory impairment, sleep disorders, cognitive impairment, etc., metabolic diseases such as obesity, diabetes, hormone abnormality, hypercholesterolemia, hyperlipidemia, gout, fatty liver, etc., genital or reproductive disorders such as infertility, preterm labor, sexual dysfunction, etc., gastro-intestinal disorders, respiratory disorders, inflammatory diseases or glaucoma, and the like, also for example, atherosclerosis, hypogonadism, hyperandrogenism, polycystic ovary syndrome, hirsutism, gastro-intestinal motility disorder, obesity-related gastro-esophageal reflux, obesity hypoventilation (Pickwickian syndrome), sleep apnea, inflammation, systemic inflammation of the vasculature, osteoarthritis, insulin resistance, bronchoconstriction, alcohol preference, metabolic syndrome, Alzheimer's disease, cardiac hypertrophy, left ventricular hypertrophy, hypertriglyceridemia, low HDL cholesterol, cardiovascular disorders such as coronary heart disease (CHD), cerebrovascular disease, stroke, peripheral vascular disease, sudden death, etc., gallbladder diseases, cancer (breast, endometrial, colon), breathlessness, hyperuricemia, impaired fertility, low back pain, or increased anesthetic risk, and the like.

The compounds of the present invention (I) are particularly useful as agents for the treatment of bulimia, obesity, diabetes and the like.

The present invention relates to the compounds of the formula (I), or the salts or esters thereof, and the production methods and the use thereof.

The present invention further relates to the intermediate for the production of the compound of the formula (I), namely a compound of the formula (III-1):

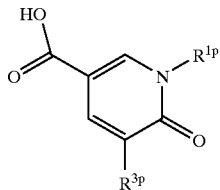

(wherein $R^{1p}$ is lower alkyl, cyclo-lower alkyl, cyclo(lower alkyl)-lower alkyl or lower alkoxy, any of which is optionally substituted by a substituent selected from the group consisting of halogen, di-lower alkylamino, lower alkoxy, formyl, lower alkoxycarbonyl, di-lower alkylcarbamoyl, optionally protected lower alkylamino, optionally protected lower alkanoylamino, optionally protected hydroxy and optionally protected lower alkylcarbamoyl;

$R^{3p}$ is hydrogen, cyano, halogen or optionally protected hydroxy, or lower alkyl, lower alkoxy or lower alkylthio, the last three groups being optionally substituted by a substituent selected from the group consisting of halogen, di-lower alkylamino, lower alkoxy, formyl, lower alkoxycarbonyl, di-lower alkylcarbamoyl, optionally protected lower alkylamino, optionally protected lower alkanoylamino, optionally protected hydroxy and optionally protected lower alkylcarbamoyl, provided that the compound of the formula (III-1) wherein $R^{1p}$ is methyl and $R^{3p}$ is hydrogen, ethyl or methoxy is excluded) and the like.

The means of terms used in the present specification are defined, and more detailed description of this invention is described below.

"Halogen" refers to fluorine, chlorine, bromine and iodine.

"Lower alkyl" refers to a straight- or branched-chain alkyl group of C1 to C6, and its examples are methyl, ethyl, propyl, isopropyl, butyl, isobutyl, sec-butyl, tert-butyl, pentyl, isopentyl, hexyl, isohexyl and the like.

"Halo-lower alkyl" refers to said lower alkyl substituted with identically or differently one, two or more, preferably one to three said halogen at the substitutable, arbitrary position(s), and its examples are fluoromethyl, difluoromethyl, trifluoromethyl, 2-fluoroethyl, 1,2-difluoroethyl, chloromethyl, 2-chloroethyl, 1,2-dichloroethyl, bromomethyl, iodomethyl and the like.

"Hydroxy-lower alkyl" refers to said lower alkyl substituted with one, two or more, preferably one or two hydroxy at the substitutable, arbitrary position(s), and its examples are hydroxymethyl, 2-hydroxyethyl, 1-hydroxy-1-methylethyl, 1,2-dihydroxyethyl, 3-hydroxypropyl and the like.

"Cyclo-lower alkyl" refers to a cycloalkyl group of C3 to C6, and its examples are cyclopropyl, cyclobutyl, cyclopentyl, cyclohexyl and the like.

"Cyclo(lower alkyl)-lower alkyl" refers to said lower alkyl substituted with one, two or more, preferably one said cyclo-lower alkyl at the substitutable, arbitrary position(s), and its examples are cyclopropylmethyl, 2-cyclopropylethyl, 3-cyclopropylpropyl, cyclobutylmethyl, 2-cyclobutylethyl, 3-cyclobutylpropyl, cyclopentylmethyl, 2-cyclopentylethyl, 3-cyclopentylpropyl, cyclohexylmethyl, 2-cyclohexylethyl, 3-cyclohexylpropyl and the like.

"Lower alkenyl" refers to a straight- or branched-chain alkenyl group of C2 to C6, and its examples are vinyl, 1-propenyl, 2-propenyl, isopropenyl, 3-butenyl, 2-butenyl, 1-butenyl, 1-methyl-2-propenyl, 1-methyl-1-propenyl, 1-ethyl-1-ethenyl, 2-methyl-2-propenyl, 2-methyl-1-propenyl, 3-methyl-2-butenyl, 4-pentenyl and the like.

"Lower alkylamino" refers to an amino group mono-substituted with said lower alkyl, and its examples are methylamino, ethylamino, propylamino, isopropylamino, butylamino, sec-butylamino, tert-butylamino, and the like.

"Di-lower alkylamino" refers to an amino group di-substituted with identically or differently said lower alkyl, and its examples are dimethylamino, diethylamino, ethylmethylamino, dipropylamino, methylpropylamino, diisopropylamino and the like.

"Lower alkanoyl" refers to an alkanoyl group containing said lower alkyl, that is, an alkanoyl group of C2 to C7, and its examples are acetyl, propionyl, butyryl, isobutyryl, valeryl, isovaleryl, pivaloyl and the like.

"Lower alkanoylamino" refers to an amino group mono-substituted with said lower alkanoyl, and its examples are acetylamino, propionylamino, butyrylamino, isobutyrylamino, valerylamino, isovalerylamino, pivaloylamino and the like.

"Lower alkylsulfonyl" refers to an alkylsulfonyl group containing said lower alkyl, and its examples are methylsulfonyl, ethylsulfonyl, propylsulfonyl, isopropylsulfonyl, butylsulfonyl, sec-butylsulfonyl, tert-butylsulfonyl, and the like.

"Lower alkylsulfonylamino" refers to an amino group mono-substituted with said lower alkylsulfonyl, and its examples are methylsulfonylamino, ethylsulfonylamino, propylsulfonylamino, isopropylsulfonylamino, butylsulfonylamino, sec-butylsulfonylamino, tert-butylsulfonylamino and the like.

"Aryl" refers to phenyl, naphthyl and the like.

"Arylsulfonyl" refers to an arylsulfonyl group containing said aryl, and its examples are phenylsulfonyl, 1-naphthylsulfonyl, 2-naphthylsulfonyl and the like.

"Arylsulfonylamino" refers to an amino group mono-substituted with said arylsulfonyl, and its examples are phenylsulfonylamino, 1-naphthylsulfonylamino, 2-naphthylsulfonylamino and the like.

"Lower alkoxy" refers to a straight- or branched-chain alkoxy group of C1 to C6, and its examples are methoxy, ethoxy, propoxy, isopropoxy, butoxy, sec-butoxy, isobutoxy, tert-butoxy, pentyloxy, isopentyloxy, hexyloxy, isohexyloxy, and the like.

"Halo-lower alkoxy" refers to said lower alkoxy substituted with identically or differently one, two or more, preferably one to three said halogen at the substitutable, arbitrary position(s), and its examples are fluoromethoxy, difluoromethoxy, trifluoromethoxy, 2-fluoroethoxy, 1,2-difluoroethoxy, chloromethoxy, 2-chloroethoxy, 1,2-dichloroethoxy, bromomethoxy, iodomethoxy and the like.

"Aryloxy" refers to aryloxy containing said aryl, and its examples are, phenoxy, 1-naphthoxy, 2-naphthoxy and the like.

"Lower alkylthio" refers to a straight- or branched-chain alkylthio group of C1 to C6, and its examples are methylthio, ethylthio, propylthio, isopropylthio, butylthio, sec-butylthio, isobutylthio, tert-butylthio, pentylthio, isopentylthio, hexylthio, isohexylthio and the like.

"Lower alkoxycarbonyl" refers to an alkoxycarbonyl group containing said lower alkoxy, that is, an alkoxycarbonyl group of C2 to C7, and its examples are methoxycarbonyl, ethoxycarbonyl, propoxycarbonyl, isopropoxycarbonyl, butoxycarbonyl, isobutoxycarbonyl, tert-butoxycarbonyl, pentyloxycarbonyl and the like.

"Lower alkylcarbamoyl" refers to a carbamoyl group mono-substituted with said lower alkyl, and its examples are methylcarbamoyl, ethylcarbamoyl, propylcarbamoyl, isopropylcarbamoyl, butylcarbamoyl, sec-butylcarbamoyl, tert-butylcarbamoyl and the like.

"Di-lower alkylcarbamoyl" refers to a carbamoyl group di-substituted with said lower alkyl, and its examples are dimethylcarbamoyl, diethylcarbamoyl, ethylmethylcarbamoyl, dipropylcarbamoyl, methylpropylcarbamoyl, diisopropylcarbamoyl and the like.

"Heteroaryl" refers to 5- or 6-membered monocyclic heteroaromatic group which contains one, two or more, preferably one to three hetero atom(s) identically or differently selected from the group consisting of oxygen, nitrogen and sulfur; or condensed cyclic heteroaromatic group, where said monocyclic heteroaromatic group is condensed with said aryl group or condensed each other with the same or different said monocyclic heteroaromatic group, and its examples are pyrrolyl, furyl, thienyl, imidazolyl, pyrazolyl, thiazolyl, isothiazolyl, oxazolyl, isoxazolyl, triazolyl, tetrazolyl, oxadiazolyl, 1,2,3-thiadiazolyl, 1,2,4-thiadiazolyl, 1,2,5-thiadiazolyl, 1,3,4-thiadiazolyl, pyridyl, pyrazinyl, pyrimidinyl, pyridazinyl, 1,2,4-triazinyl, 1,3,5-triazinyl, indolyl, benzofuranyl, benzothienyl, benzoimidazolyl, benzoxazolyl, benzoisoxazolyl, benzothiazolyl, benzoisothiazolyl, indazolyl, purinyl, quinolyl, isoquinolyl, phthalazinyl, naphthylidinyl, quinoxalinyl, quinazolinyl, cinnolinyl, pteridinyl, 1,5-naphthyridinyl and the like.

"Heteroaryloxy" refers to a heteroaryloxy group containing said heteroaryl, and its examples are 2-thienyloxy, 3-thienyloxy, 2-pyridyloxy, 3-pyridyloxy, 4-pyridyloxy, 3-indolyloxy, 4-indolyloxy, 5-indolyloxy, 6-indolyloxy and the like.

The salts of the compounds of the formula (I) refer to the pharmaceutically acceptable, common salts, and examples thereof are base addition salt to said carboxyl group or hydroxy when the compound has a carboxyl group or a hydroxy, or acid addition salt to said amino or basic heterocyclyl when the compound has an amino or a basic heterocyclyl group and the like.

Said base addition salts include salts with alkali metals (e.g. sodium, potassium); salts with alkaline earth metals (e.g. calcium, magnesium); ammonium salts; salts with organic amines (e.g. trimethylamine, triethylamine, dicyclohexylamine, ethanolamine, diethanolamine, triethanolamine, procaine, N,N'-dibenzylethylenediamine) and the like.

Said acid addition salts include salts with inorganic acids (e.g. hydrochloric acid, sulfuric acid, nitric acid, phosphoric acid, perchloric acid), salts with organic acids (e.g. maleic acid, fumaric acid, tartaric acid, citric acid, ascorbic acid, trifluoroacetic acid), salts with sulfonic acids (e.g. methanesulfonic acid, isethionic acid, benzenesulfonic acid, p-toluenesulfonic acid) and the like.

The esters of the compounds of the formula (I) refer to, for example, the pharmaceutically acceptable, common esters of said carboxyl group when the compound has a carboxyl group, and examples thereof are esters with lower alkyl (e.g. methyl, ethyl, propyl, isopropyl, butyl, sec-butyl, tert-butyl, pentyl, isopentyl, neopentyl, cyclopropyl, cyclobutyl, cyclopentyl), esters with aralkyl (e.g. benzyl, phenethyl), esters with lower alkenyl (e.g. allyl, 2-butenyl), esters with lower-alkoxy-lower-alkyl (e.g. methoxymethyl, 2-methoxyethyl, 2-ethoxyethyl), esters with lower-alkanoyloxy-lower-alkyl (e.g. acetoxymethyl, pivaloyloxymethyl, 1-pivaloyloxyethyl), esters with lower-alkoxycarbonyl-lower-alkyl (e.g. methoxycarbonylmethyl, isopropoxycarbonylmethyl), esters with carboxy-lower alkyl (e.g. carboxymethyl), esters with lower-alkoxycarbonyloxy-lower-alkyl (e.g. 1-(ethoxycarbonyloxy)ethyl, 1-(cyclohexyloxycarbonyloxy)ethyl), esters with carbamoyloxy-lower alkyl (e.g. carbamoyloxymethyl), esters with phthalidyl, esters with (5-substituted-2-oxo-1,3-dioxol-4-yl)methyl (e.g. (5-methyl-2-oxo-1,3-dioxol-4-yl) methyl) and the like.

"An agent for treatment" refers to a medicament which is employed for the treatment and/or prophylaxis of various diseases.

In order to disclose the aforesaid compounds of the formula (I) of the present invention more specifically, the various symbols used in the formula (I) are explained in more detail by presenting preferred embodiments.

$Ar^1$ and $Ar^2$ are independently aryl or heteroaryl, any of which is optionally substituted by a substituent selected from the group consisting of cyano, halogen, nitro, lower alkyl, halo-lower alkyl, hydroxy-lower alkyl, cyclo-lower alkyl, cyclo(lower alkyl)-lower alkyl, lower alkenyl, lower alkylamino, di-lower alkylamino, lower alkanoylamino, lower alkylsulfonylamino, arylsulfonylamino, hydroxy, lower alkoxy, halo-lower alkoxy, aryloxy, heteroaryloxy, lower alkylthio, carboxyl, formyl, lower alkanoyl, lower alkoxycarbonyl, carbamoyl, lower alkylcarbamoyl, di-lower alkylcarbamoyl, lower alkylsulfonyl, arylsulfonyl, aryl and heteroaryl.

"Aryl or heteroaryl, any of which is optionally substituted by a substituent selected from the group consisting of cyano, halogen, nitro, lower alkyl, halo-lower alkyl, hydroxy-lower alkyl, cyclo-lower alkyl, cyclo(lower alkyl)-lower alkyl, lower alkenyl, lower alkylamino, di-lower alkylamino, lower alkanoylamino, lower alkylsulfonylamino, arylsulfonylamino, hydroxy, lower alkoxy, halo-lower alkoxy, aryloxy, heteroaryloxy, lower alkylthio, carboxyl, formyl, lower alkanoyl, lower alkoxycarbonyl, carbamoyl, lower alkylcarbamoyl, di-lower alkylcarbamoyl, lower alkylsulfonyl, arylsulfonyl, aryl and heteroaryl" refers to unsubstituted said aryl or said heteroaryl, or said aryl or said heteroaryl, the last two groups having substituent(s) at the substitutable, arbitrary position(s) wherein said substituent (s) may be one, two or more, preferably one or two member (s) identically or differently selected from the group consisting of cyano, halogen, nitro, lower alkyl, halo-lower alkyl, hydroxy-lower alkyl, cyclo-lower alkyl, cyclo(lower alkyl)-lower alkyl, lower alkenyl, lower alkylamino, di-lower alkylamino, lower alkanoylamino, lower alkylsulfonylamino, arylsulfonylamino, hydroxy, lower alkoxy, halo-lower alkoxy, aryloxy, heteroaryloxy, lower alkylthio, carboxyl, formyl, lower alkanoyl, lower alkoxycarbonyl, carbamoyl, lower alkylcarbamoyl, di-lower alkylcarbamoyl, lower alkylsulfonyl, arylsulfonyl, aryl and heteroaryl.

Halogen as said substituent includes preferably fluorine, chlorine, bromine and the like, more preferably fluorine and the like.

Lower alkyl as said substituent preferably includes methyl, ethyl, propyl, isopropyl and the like.

Halo-lower alkyl as said substituent preferably includes difluoromethyl, trifluoromethyl and the like.

Hydroxy-lower alkyl as said substituent preferably includes hydroxymethyl, 2-hydroxyethyl, 1-hydroxy-1-methylethyl and the like.

Cyclo-lower alkyl as said substituent preferably includes cyclopropyl and the like.

Cyclo(lower alkyl)-lower alkyl as said substituent preferably includes cyclopropylmethyl, cyclobutylmethyl, cyclopentylmethyl and the like.

Lower alkenyl as said substituent preferably includes vinyl, 1-propenyl, 2-methyl-1-propenyl and the like.

Lower alkylamino as said substituent preferably includes methylamino, ethylamino and the like.

Di-lower alkylamino as said substituent preferably includes dimethylamino, diethylamino and the like.

Lower alkanoylamino as said substituent preferably includes acetylamino, propionylamino and the like.

Lower alkylsulfonylamino as said substituent preferably includes methylsulfonylamino, ethylsulfonylamino and the like.

Arylsulfonylamino as said substituent preferably includes phenylsulfonylamino and the like.

Lower alkoxy as said substituent preferably includes methoxy, ethoxy and the like.

Halo-lower alkoxy as said substituent preferably includes fluoromethoxy, difluoromethoxy, trifluoromethoxy and the like.

Aryloxy as said substituent preferably includes phenoxy and the like.

Heteroaryloxy as said substituent preferably includes 2-pyridyloxy, 3-pyridyloxy, 4-pyridyloxy and the like.

Lower alkylthio as said substituent preferably includes methylthio, ethylthio and the like.

Lower alkanoyl as said substituent preferably includes formyl, acetyl, propionyl and the like.

Lower alkoxycarbonyl as said substituent preferably includes methoxycarbonyl, ethoxycarbonyl and the like.

Lower alkylcarbamoyl as said substituent preferably includes methylcarbamoyl, ethylcarbamoyl and the like.

Di-lower alkylcarbamoyl as said substituent preferably includes dimethylcarbamoyl, diethylcarbamoyl and the like.

Lower alkylsulfonyl as said substituent preferably includes methylsulfonyl, ethylsulfonyl and the like.

Arylsulfonyl as said substituent preferably includes phenylsulfonyl and the like.

Aryl as said substituent preferably includes phenyl and the like.

Heteroaryl as said substituent preferably includes thienyl, thiazolyl, isothiazolyl, pyridyl, pyrazinyl and the like.

The substituents of $Ar^1$ or $Ar^2$ preferably include halogen, halo-lower alkyl and the like.

Aryl as $Ar^1$ or $Ar^2$ preferably includes phenyl and the like, and heteroaryl as $Ar^1$ or $Ar^2$ preferably includes pyridyl and the like.

More specifically, $Ar^1$ or $Ar^2$ includes, for example, phenyl, 2-fluorophenyl, 3-fluorophenyl, 4-fluorophenyl, 2-chlorophenyl, 3-chlorophenyl, 4-chlorophenyl, 2-bromophenyl, 3-bromophenyl, 3-bromo-4-fluorophenyl, 4-bromophenyl, 2-methylphenyl, 3-methylphenyl, 4-methylphenyl, 2-trifluoromethylphenyl, 3-trifluoromethylphenyl, 4-trifluoromethylphenyl, 2-hydroxymethylphenyl, 3-hydroxymethylphenyl, 4-hydroxymethylphenyl, 2-methoxyphenyl, 3-methoxyphenyl, 4-methoxyphenyl, 2-difluoromethoxyphenyl, 3-difluoromethoxyphenyl, 4-difluoromethoxyphenyl, 2-trifluoromethoxyphenyl, 3-trifluoromethoxyphenyl, 4-trifluoromethoxyphenyl, 2-formylphenyl, 3-formylphenyl, 4-formylphenyl, 2-thienyl, 4-chloro-2-thienyl, 5-chloro-2-thienyl, 4-bromo-2-thienyl, 5-bromo-2-thienyl, 4-methyl-2-thienyl, 5-methyl-2-thienyl, 4-methoxy-2-thienyl, 5-methoxy-2-thienyl, 3-thienyl, 5-chloro-3-thienyl, 5-methyl-3-thienyl, 5-methoxy-3-thienyl, 2-pyridyl, 4-methyl-2-pyridyl, 5-methyl-2-pyridyl, 4-methoxy-2-pyridyl, 5-methoxy-2-pyridyl, 4-chloro-2-pyridyl, 5-chloro-2-pyridyl, 3-pyridyl, 4-methyl-3-pyridyl, 5-methyl-3-pyridyl, 4-methoxy-3-pyridyl, 5-methoxy-3-pyridyl, 6-fluoro-3-pyridyl, 4-chloro-3-pyridyl, 5-chloro-3-pyridyl, 6-difluoromethyl-3-pyridyl, 6-trifluoromethyl-3-pyridyl, 6-cyclopropyl-3-pyridyl, 4-pyridyl, 2-fluoro-4-pyridyl, 2-chloro-4-pyridyl, 3-chloro-4-pyridyl, 2-methyl-4-pyridyl, 3-methyl-4-pyridyl, 2-methoxy-4-pyridyl, 3-methoxy-4-pyridyl, etc. Among the above, the preferable examples are 2-fluorophenyl, 3-fluorophenyl, 4-fluorophenyl, 2-chlorophenyl, 3-chlorophenyl, 4-chlorophenyl, 3-bromophenyl, 3-bromo-4-fluorophenyl, 4-bromophenyl, 3-methylphenyl, 3-trifluoromethylphenyl, 4-trifluoromethylphenyl, 3-methoxyphenyl, 4-methoxyphenyl, 3-trifluoromethoxyphenyl, 4-trifluoromethoxyphenyl, 3-difluoromethoxyphenyl, 4-difluoromethoxyphenyl, 2-thienyl, 4-chloro-2-thienyl, 5-chloro-2-thienyl, 4-bromo-2-thienyl, 5-bromo-2-thienyl, 3-pyridyl, 4-methoxy-3-pyridyl, 5-methoxy-3-pyridyl, 6-fluoro-3-pyridyl, 4-chloro-3-pyridyl, 5-chloro-3-pyridyl, 6-difluoromethyl-3-pyridyl, 6-trifluoromethyl-3-pyridyl, 6-cyclopropyl-3-pyridyl, 2-fluoro-4-pyridyl, etc., and the particularly preferable examples are 4-fluorophenyl, 4-chlorophenyl, 3-bromo-4-fluorophenyl, 3-trifluoromethylphenyl, 4-trifluoromethylphenyl, 6-fluoro-3-pyridyl, 6-difluoromethyl-3-pyridyl, 6-trifluoromethyl-3-pyridyl, 2-fluoro-4-pyridyl, etc.

The preferred embodiment of $Ar^1$ and $Ar^2$ includes, for example, the case where one of them is aryl which is substituted by a substituent selected from the group consisting of halogen and halo-lower alkyl, and the other is heteroaryl which is substituted by a substituent selected from the group consisting of halogen and halo-lower alkyl. The particularly preferable embodiment of $Ar^1$ and $Ar^2$ includes, for example, the case where one of them is 4-fluorophenyl, 4-chlorophenyl, 3-trifluoromethylphenyl or 4-trifluoromethylphenyl, and the other is 6-fluoro-3-pyridyl; the case where one of them is 4-fluorophenyl, 4-chlorophenyl, 3-trifluoromethylphenyl or 4-trifluoromethylphenyl, and the other is 2-fluoro-4-pyridyl; the case where one of them is 4-fluorophenyl, 4-chlorophenyl, 3-trifluoromethylphenyl or 4-trifluoromethylphenyl, and the other is 6-trifluoromethyl-3-pyridyl; the case where one of them is 4-fluorophenyl or 4-chlorophenyl, and the other is 6-difluoromethyl-3-pyridyl.

$R^1$ and $R^2$ are independently lower alkyl, cyclo-lower alkyl, cyclo(lower alkyl)-lower alkyl or lower alkoxy, any of which is optionally substituted by a substituent selected from the group consisting of halogen, lower alkylamino, di-lower alkylamino, lower alkanoylamino, hydroxy, lower alkoxy, formyl, lower alkoxycarbonyl, lower alkylcarbamoyl and di-lower alkylcarbamoyl.

"Lower alkyl, cyclo-lower alkyl, cyclo(lower alkyl)-lower alkyl or lower alkoxy, any of which is optionally substituted by a substituent selected from the group consisting of halogen, lower alkylamino, di-lower alkylamino, lower alkanoylamino, hydroxy, lower alkoxy, formyl, lower alkoxycarbonyl, lower alkylcarbamoyl and di-lower alkylcarbamoyl" refers to unsubstituted said lower alkyl, cyclo-lower alkyl, cyclo(lower alkyl)-lower alkyl or lower alkoxy, or said lower alkyl, cyclo-lower alkyl, cyclo(lower alkyl)-lower alkyl or lower alkoxy, the last four groups having substituent(s) at the substitutable, arbitrary position(s) wherein said substituent(s) may be one, two or more, preferably one or two member(s) identically or differently selected from the group consisting of halogen, lower alkylamino, di-lower alkylamino, lower alkanoylamino, hydroxy, lower alkoxy, formyl, lower alkoxycarbonyl, lower alkylcarbamoyl and di-lower alkylcarbamoyl.

Halogen as said substituent preferably includes fluorine and the like.

Lower alkylamino as said substituent preferably includes methylamino, ethylamino and the like.

Di-lower alkylamino as said substituent preferably includes dimethylamino, diethylamino and the like.

Lower alkanoylamino as said substituent preferably includes acetylamino, propionylamino and the like.

Lower alkoxy as said substituent preferably includes methoxy, ethoxy and the like.

Lower alkoxycarbonyl as said substituent preferably includes methoxycarbonyl, ethoxycarbonyl and the like.

Lower alkylcarbamoyl as said substituent preferably includes methylcarbamoyl, ethylcarbamoyl and the like.

Di-lower alkylcarbamoyl as said substituent preferably includes dimethylcarbamoyl, diethylcarbamoyl and the like.

The substituent of lower alkyl, cyclo-lower alkyl, cyclo (lower alkyl)-lower alkyl or lower alkoxy as $R^1$ preferably includes halogen and the like.

Lower alkyl as $R^1$ preferably includes methyl, ethyl, propyl, isopropyl, isobutyl and the like.

Cyclo-lower alkyl as $R^1$ preferably includes cyclopropyl, cyclobutyl and the like.

Cyclo (lower alkyl)-lower alkyl as $R^1$ preferably includes cyclopropylmethyl, 2-cyclopropylethyl, cyclobutylmethyl and the like.

Lower alkoxy as $R^1$ preferably includes methoxy, ethoxy, propoxy, isopropoxy, isobutoxy and the like.

$R^1$ preferably includes lower alkyl, cyclo-lower alkyl or lower alkoxy, any of which is optionally substituted by said substituent(s).

More specifically, $R^1$ includes, for example, methyl, fluoromethyl, difluoromethyl, trifluoromethyl, ethyl, cyclopropyl, cyclobutyl, 2-fluoroethyl, 2,2-difluoroethyl, propyl, isopropyl, isobutyl, methoxy, difluoromethoxy, ethoxy, 2-fluoroethoxy, 2,2-difluoroethoxy, propoxy, isopropoxy, isobutoxy and the like, preferably methyl, difluoromethyl, ethyl, 2,2-difluoroethyl, propyl, isopropyl, cyclopropyl, methoxy, ethoxy and the like.

The substituent of lower alkyl, cyclo-lower alkyl, cyclo (lower alkyl)-lower alkyl or lower alkoxy as $R^2$ preferably includes halogen, lower alkylamino, di-lower alkylamino, hydroxy, lower alkoxy and the like.

Lower alkyl as $R^2$ includes preferably methyl, ethyl, propyl, isopropyl, isobutyl and the like, more preferably methyl and the like.

Cyclo-lower alkyl as $R^2$ preferably includes cyclopropyl, cyclobutyl and the like.

Cyclo (lower alkyl)-lower alkyl as $R^2$ preferably includes cyclopropylmethyl, 2-cyclopropylethyl, cyclobutylmethyl and the like.

Lower alkoxy as $R^2$ includes preferably methoxy, ethoxy, propoxy, isopropoxy, isobutoxy and the like, more preferably methoxy and the like.

$R^2$ includes preferably lower alkyl which is optionally substituted by said substituent and the like, more preferably methyl and the like.

$R^3$, $R^4$ and $R^5$ are independently hydrogen, cyano, halogen or hydroxy, or lower alkyl, lower alkoxy or lower alkylthio, the last three groups being optionally substituted by a substituent selected from the group consisting of halogen, lower alkylamino, di-lower alkylamino, lower alkanoylamino, hydroxy, lower alkoxy, formyl, lower alkoxycarbonyl, lower alkylcarbamoyl and di-lower alkylcarbamoyl.

Halogen as $R^3$, $R^4$ or $R^5$ includes, for example, preferably fluorine, chlorine, bromine and the like, more preferably fluorine, chlorine and the like.

"Lower alkyl, lower alkoxy or lower alkylthio, any of which is optionally substituted by a substituent selected from the group consisting of halogen, lower alkylamino, di-lower alkylamino, lower alkanoylamino, hydroxy, lower alkoxy, formyl, lower alkoxycarbonyl, lower alkylcarbamoyl and di-lower alkylcarbamoyl" refers to unsubstituted said lower alkyl, lower alkoxy or lower alkylthio, or said lower alkyl, lower alkoxy or lower alkylthio, the last three groups having substituent(s) at the substitutable, arbitrary position(s) wherein said substituent(s) may be one, two or more, preferably one or two member(s) identically or differently selected from the group consisting of halogen, lower alkylamino, di-lower alkylamino, lower alkanoylamino, hydroxy, lower alkoxy, formyl, lower alkoxycarbonyl, lower alkylcarbamoyl and di-lower alkylcarbamoyl.

Halogen as said substituent preferably includes fluorine and the like.

Lower alkylamino as said substituent preferably includes methylamino, ethylamino and the like.

Di-lower alkylamino as said substituent preferably includes dimethylamino, diethylamino and the like.

Lower alkanoylamino as said substituent preferably includes acetylamino, propionylamino and the like.

Lower alkoxy as said substituent preferably includes methoxy, ethoxy and the like.

Lower alkoxycarbonyl as said substituent preferably includes methoxycarbonyl, ethoxycarbonyl and the like.

Lower alkylcarbamoyl as said substituent preferably includes methylcarbamoyl, ethylcarbamoyl and the like.

Di-lower alkylcarbamoyl as said substituent preferably includes dimethylcarbamoyl, diethylcarbamoyl and the like.

The substituent of lower alkyl, lower alkoxy or lower alkylthio as $R^3$, $R^4$ or $R^5$ preferably includes halogen and the like.

Lower alkyl being optionally substituted by said substituent as $R^3$, $R^4$ or $R^5$ includes methyl, fluoromethyl, difluoromethyl, trifluoromethyl, ethyl, 2-fluoroethyl, 2,2-difluoroethyl, propyl, isopropyl, isobutyl and the like, among which the preferred are methyl, ethyl and the like. Lower alkoxy being optionally substituted by said substituent as $R^3$, $R^4$ or $R^5$ includes methoxy, difluoromethoxy, ethoxy, 2-fluoroethoxy, 2,2-difluoroethoxy, propoxy, isopropoxy, isobutoxy and the like, among which the preferred is methoxy and the like. Lower alkylthio being optionally substituted by said substituent as $R^3$, $R^4$ or $R^5$ includes methylthio, ethylthio, propylthio, isopropylthio, isobutylthio and the like, among which the preferred is methylthio and the like.

The preferable examples of $R^3$, $R^4$ or $R^5$ are hydrogen, halogen, hydroxy, lower alkyl optionally having said substituent(s) and the like, and among which, for example, the case where $R^3$ is hydrogen, halogen or hydroxy or lower alkyl optionally having said substituent(s), and both $R^4$ and $R^5$ are hydrogen is more preferable.

In the formula (I), the group represented by the formula (a):

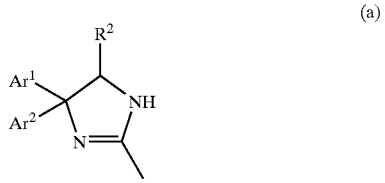

$R^3$, $R^4$ and $R^5$ each can be present at the substitutable, arbitrary position(s) on N-substituted-2-oxodihydropyridine ring represented by the formula (b):

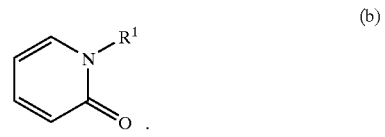

Among the compounds of the formula (I), the compound of the formula (I-1):

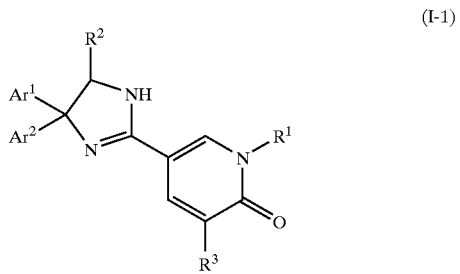

(wherein $Ar^1$, $Ar^2$, $R^1$, $R^2$ and $R^3$ have each the same meaning as defined above) and the like are preferable.

Among the compounds of the formula (I) or formula (I-1), the preferable compounds is, for example, the compound in which one of $Ar^1$ and $Ar^2$ is aryl, more preferably phenyl, substituted by a substituent selected from the group consisting of halogen and halo-lower alkyl, and the other is heteroaryl, more preferably 3-pyridyl or 4-pyridyl, substituted by a substituent selected from the group consisting of halogen and halo-lower alkyl; $R^1$ is lower alkyl, cyclo-lower alkyl or lower alkoxy, any of which is optionally substituted by said substituent(s); $R^2$ is lower alkyl, preferably methyl, optionally substituted by said substituent (s); and $R^3$ is hydrogen, halogen or hydroxy, or lower alkyl optionally having said substituent(s). Among the compound of the formula (I), in addition to the above embodiment, the compound in which both $R^4$ and $R^5$ are hydrogen is preferable.

The compounds of the present invention may include stereoisomers such as optical isomers, diastereoisomers and geometrical isomers, or tautomers depending upon the mode of substituents. The compounds of the present invention include all the stereoisomers, tautomers and their mixtures.

Also included within the scope of the invention are polymorphs, hydrates and solvates of the compounds of the present invention.

The present invention also includes prodrugs of the compounds of the present invention within its scope. In general, such prodrugs are functional derivatives of the compounds of the present invention which can be readily converted in vivo into the required compound. Thus, in the treatment methods for various diseases according to the present invention, the term "administering" shall encompass not only administration of the compound specified in this disclosure but also administration of a compound which is converted in vivo into the specified compound when it is administered to a patient. Conventional procedures for selection and preparation of suitable prodrug derivatives are described, for example, in "Design of Prodrugs," ed. H. Bundgaard, Elsevier (1985), which are referred and entirely incorporated in this specification. The metabolites of these compounds include active compounds which are produced upon introduction of compounds of the present invention into the biological milieu, and they are encompassed in the scope of the present invention.

The specific compounds of the formula (I) are, for example,

5-[(4S,5S)-4-(4-fluorophenyl)-4-(6-fluoro-3-pyridyl)-5-methyl-2-imidazolin-2-yl]-1-methyl-2-pyridone, 1-difluoromethyl-5-[(4S,5S)-4-(4-fluorophenyl)-4-(6-fluoro-3-pyridyl)-5-methyl-2-imidazolin-2-yl]-2-pyridone, 1-ethyl-5-[(4S,5S)-4-(4-fluorophenyl)-4-(6-fluoro-3-pyridyl)-5-methyl-2-imidazolin-2-yl]-2-pyridone, 1-difluoromethyl-5-[(4R,5S)-4-(4-fluorophenyl)-4-(2-fluoro-4-pyridyl)-5-methyl-2-imidazolin-2-yl]-2-pyridone, 1-(2,2-difluoroethyl)-5-[(4S,5S)-4-(4-fluorophenyl)-4-(6-fluoro-3-pyridyl)-5-methyl-2-imidazolin-2-yl]-2-pyridone, 5-[(4S,5S)-4-(4-fluorophenyl)-4-(6-fluoro-3-pyridyl)-5-methyl-2-imidazolin-2-yl]-1-propyl-2-pyridone, 5-[(4S,5S)-4-(4-fluorophenyl)-4-(6-fluoro-3-pyridyl)-5-methyl-2-imidazolin-2-yl]-1-isopropyl-2-pyridone, 1-difluoromethyl-5-[(4R,5S)-4-(4-fluorophenyl)-5-methyl-4-(6-trifluoromethyl-3-pyridyl)-2-imidazolin-2-yl]-2-pyridone, 1-difluoromethyl-5-[(4S,5S)-4-(4-fluorophenyl)-5-methyl-4-(6-trifluoromethyl-3-pyridyl)-2-imidazolin-2-yl]-2-pyridone, 1-ethyl-5-[(4R,5S)-4-(4-fluorophenyl)-5-methyl-4-(6-trifluoromethyl-3-pyridyl)-2-imidazolin-2-yl]-2-pyridone, 1-ethyl-5-[(4S,5S)-4-(4-fluorophenyl)-5-methyl-4-(6-trifluoromethyl-3-pyridyl)-2-imidazolin-2-yl]-2-pyridone, 5-[(4R,5S)-4-(4-fluorophenyl)-5-methyl-4-(6-trifluoromethyl-3-pyridyl)-2-imidazolin-2-yl]-1-propyl-2-pyridone, 5-[(4S,5S)-4-(4-fluorophenyl)-5-methyl-4-(6-trifluoromethyl-3-pyridyl)-2-imidazolin-2-yl]-1-propyl-2-pyridone, 1-(2,2-difluoroethyl)-5-[(4R,5S)-4-(4-fluorophenyl)-5-methyl-4-(6-trifluoromethyl-3-pyridyl)-2-imidazolin-2-yl]-2-pyridone, 1-(2,2-difluoroethyl)-5-[(4S,5S)-4-(4-fluorophenyl)-5-methyl-4-(6-trifluoromethyl-3-pyridyl)-2-imidazolin-2-yl]-2-pyridone, 3-chloro-1-ethyl-5-[(4R,5S)-4-(4-fluorophenyl)-5-methyl-4-(6-trifluoromethyl-3-pyridyl)-2-imidazolin-2-yl]-2-pyridone, 3-chloro-1-ethyl-5-[(4S,5S)-4-(4-fluorophenyl)-5-methyl-4-(6-trifluoromethyl-3-pyridyl)-2-imidazolin-2-yl]-2-pyridone, 5-[(4S,5S)-4-(3-bromo-4-fluorophenyl)-4-(6-fluoro-3-pyridyl)-5-methyl-2-imidazolin-2-yl]-1-difluoromethyl-2-pyridone, 1-difluoromethyl-5-[(4S,5S)-4-(4-fluorophenyl)-4-(2-fluoro-4-pyridyl)-5-methyl-2-imidazolin-2-yl]-2-pyridone, 1-ethyl-5-[(4S,5S)-4-(4-fluorophenyl)-4-(2-fluoro-4-pyridyl)-5-methyl-2-2-imidazolin-2-yl]-2-pyridone, 1-(2,2-difluoroethyl)-5-[(4S,5S)-4-(4-fluorophenyl)-4-(2-fluoro-4-pyridyl)-5-methyl-2-imidazolin-2-yl]-2-pyridone, 1-difluoromethyl-5-[(4S,5S)-4-(2-fluoro-4-pyridyl)-5-methyl-4-(4-trifluorophenyl)-2-imidazolin-2-yl]-2-pyridone, 1-difluoromethyl-5-[(4S,5S)-4-(2-fluoro-4-pyridyl)-5-methyl-4-(4-trifluorophenyl)-2-imidazolin-2-yl]-2-pyridone, 1-ethyl-5-[(4R,5S)-4-(4-fluorophenyl)-4-(2-fluoro-4-pyridyl)-5-methyl-2-imidazolin-2-yl]-2-pyridone, 3-chloro-1-ethyl-5-[(4S,5S)-4-(4-fluorophenyl)-4-(6-fluoro-3-pyridyl)-5-methyl-2-imidazolin-2-yl]-2-pyridone, 5-[(4R,5S)-4-(4-fluorophenyl)-5-methyl-4-(6-trifluoromethyl-3-pyridyl)-2-imidazolin-2-yl]-2-pyridone, 5-[(4S,5S)-4-(4-fluorophenyl)-5-methyl-4-(6-trifluoromethyl-3-pyridyl)-2-imidazolin-2-yl]-2-pyridone, 1-difluoromethyl-5-[(4R,5S)-4-(4-fluorophenyl)-4-(6-fluoro-3-pyridyl)-5-methyl-2-imidazolin-2-yl]-2-pyridone, 1-difluoromethyl-5-[(4R,5S)-4-(4-chlorophenyl)-4-(2-fluoro-4-pyridyl)-5-methyl-2-imidazolin-2-yl]-2-pyridone, 1-difluoromethyl-5-[(4S,5S)-4-(4-chlorophenyl)-4-(2-fluoro-4-pyridyl)-5-methyl-2-imidazolin-2-yl]-2-pyridone, 1-ethyl-5-[(4R,5S)-4-(2-fluoro-4-pyridyl)-5-methyl-4-(4-trifluoromethylphenyl)-2-imidazolin-2-yl]-2-pyridone, 1-ethyl-5-[(4S,5S)-4-(2-fluoro-4-pyridyl)-5-methyl-4-(4-trifluoromethylphenyl)-2-imidazolin-2-yl]-2-pyridone, 1-ethyl-5-[(4R,5S)-4-(4-chlorophenyl)-4-(2-fluoro-4-pyridyl)-5-methyl-2-imidazolin-2-yl]-2-pyridone, 1-ethyl-5-[(4S,5S)-4-(4-chlorophenyl)-4-(2-fluoro-4-pyridyl)-5-methyl-2-imidazolin-2-yl]-2-pyridone, 3-chloro-1-ethyl-5-[(4R,5S)-4-(4-fluorophenyl)-4-(2-fluoro-4-pyridyl)-5-methyl-2-imidazolin-2-yl]-2-pyridone, 1-ethyl-3-fluoro-5-[(4S,5S)-4-(4-fluorophenyl)-4-(6-fluoro-3-pyridyl)-5-methyl-2-imidazolin-2-yl]-1-methyl-2-pyridone, 3-chloro-5-[(4S,5S)-4-(4-fluorophenyl)-4-(6-fluoro-3-pyridyl)-5-methyl-2-imidazolin-2-yl]-3methyl-2-pyridone, 1-ethyl-5-[(4S,5S)-4-(4-fluorophenyl)-4-(6-fluoro-3-pyridyl)-5-methyl-2-imidazolin-2-yl]-3-methyl-2-pyridone, 3-chloro-5-[(4R,5S)-4-(4-fluorophenyl)-5-methyl-4-(6-trifluoromethyl-3-pyridyl)-2-imidazolin-2-yl]-1-methyl-2-pyridone, 3-chloro-5-[(4S,5S)-4-(4-fluorophenyl)-5-methyl-4-(6-trifluoromethyl-3-pyridyl)-2-imidazolin-2-yl]-1-methyl-2-pyridone, 1-ethyl-3-fluoro-5-[(4R,5S)-4-(4-fluorophenyl)-5-methyl-4-(6-trifluoromethyl-3-pyridyl)-2-imidazolin-2-yl]-2-pyridone, 1-ethyl-3-fluoro-5-[(4S,5S)-4-(4-fluorophenyl)-5-methyl-4-(6-trifluoromethyl-3-pyridyl)-2-imidazolin-2-yl]-2-pyridone, 1-ethyl-5-[(4R,5S)-4-(4-fluorophenyl)-4-(6-fluoro-3-pyridyl)-5-methyl-2-imidazolin-2-yl]-2-pyridone, 1-(2,2-difluoroethyl)-5-[(4R,5S)-4-(4-fluorophenyl)-4-(6-fluoro-3-pyridyl)-5-methyl-2-imidazolin-2-yl]-2-pyridone, 5-[(4S,5S)-4-(4-fluorophenyl)-4-(6-fluoro-3-pyridyl)-5-methyl-2-imidazolin-2-yl]-1,3-dimethyl-2-pyridone, 3-chloro-5-[(4R,5S)-4-(4-fluorophenyl)-4-(6-fluoro-3-pyridyl)-5-methyl-2-imidazolin-2-yl]-1-methyl-2-pyridone, 3-chloro-1-ethyl-5-[(4R,5S)-4-(4-fluorophenyl)-4-(6-fluoro-3-pyridyl)-5-methyl-2-imidazolin-2-yl]-2-pyridone, 1-ethyl-3-fluoro-5-[(4R,5S)-4-(4-fluorophenyl)-4-(6-fluoro-3-pyridyl)-5-methyl-2-imidazolin-2-yl]-2-pyridone, 1-difluoromethyl-5-[(4R,5S)-4-(6-difluoromethyl-3-pyridyl)-4-(4-fluorophenyl)-5-methyl-2-imidazolin-2-yl]-2-pyridone, 1-difluoromethyl-5-[(4S,5S)-4-(6-difluoromethyl-3-pyridyl)-4-(4-fluorophenyl)-5-methyl-2-imidazolin-2-yl]-2-pyridone, 5-[(4R,5S)-4-(4-fluorophenyl)-4-(6-fluoro-3-pyridyl)-5-methyl-2-imidazolin-2-yl]-1-methyl-2-pyridone, 1-ethyl-3-fluoro-5-[(4R,5S)-4-(4-chlorophenyl)-4-(2-fluoro-4-pyridyl)-5-methyl-2-imidazolin-2-yl]-2-pyridone, 1-ethyl-3-fluoro-5-[(4S,5S)-4-(4-chlorophenyl)-4-(2-fluoro-4-pyridyl)-5-methyl-2-imidazolin-2-yl]-2-pyridone, 3-ethyl-5-[(4S,5S)-4-(4-fluorophenyl)-4-(6-fluoro-3-pyridyl)-5-methyl-2-imidazolin-2-yl]-1-methyl-2-pyridone, 3-ethyl-5-[(4R,5S)-4-(4-fluorophenyl)-4-(2-fluoro-4-pyridyl)-5-methyl-2-imidazolin-2-yl]-1-methyl-2-pyridone, 3-ethyl-5-[(4R,5S)-4-(4-fluorophenyl)-4-(6-fluoro-3-pyridyl)-5-methyl-2-imidazolin-2-yl]-1-methyl-2-pyridone, 1-ethyl-5-[(4S,5S)-4-(4-fluorophenyl)-4-(6-fluoro-3-pyridyl)-5-methyl-2-imidazolin-2-yl]-3-methoxy-2-pyridone, 1-difluoromethyl-5-[(4R,5S)-4-(6-difluoromethyl-3-pyridyl)-4-(4-fluorophenyl)-5-methyl-2-imidazolin-2-yl]-2-pyridone, 1-difluoromethyl-5-[(4S,5S)-4-(6-difluoromethyl-3-pyridyl)-4-(4-fluorophenyl)-5-methyl-2-imidazolin-2-yl]-2-pyridone, 5-[(4R,5S)-4-(6-difluoromethyl-3-pyridyl)-4-(4-fluorophenyl)-5-methyl-2-imidazolin-2-yl]-1-ethyl-2-pyridone, 5-[(4S,5S)-4-(6-difluoromethyl-3-pyridyl)-4-(4-fluorophenyl)-5-methyl-2-imidazolin-2-yl]-1-ethyl-2-pyridone, 5-[(4R,5S)-4-(6-difluoromethyl-3-pyridyl)-4-(4-fluorophenyl)-5-methyl-2-imidazolin-2-yl]-1-ethyl-3-fluoro-2-pyridone,
5-[(4S,5S)-4-(6-difluoromethyl-3-pyridyl)-4-(4-fluorophenyl)-5-methyl-2-imidazolin-2-yl]-1-ethyl-3-fluoro-2-pyridone,
5-[(4S,5S)-4-(4-fluorophenyl)-4-(6-fluoro-3-pyridyl)-5-methyl-2-imidazolin-2-yl]-1-methoxy-2-pyridone,
5-[(4R,5S)-4-(4-fluorophenyl)-4-(6-fluoro-3-pyridyl)-5-methyl-2-imidazolin-2-yl]-1-methoxy-2-pyridone,
1-ethoxy-5-[(4R,5S)-4-(4-fluorophenyl)-4-(6-fluoro-3-pyridyl)-5-methyl-2-imidazolin-2-yl]-2-pyridone,
1-cyclopropyl-5-[(4S,5S)-4-(4-fluorophenyl)-4-(6-fluoro-3-pyridyl)-5-methyl-2-imidazolin-2-yl]-2-pyridone,
1-cyclopropyl-5-[(4R,5S)-4-(4-fluorophenyl)-5-methyl-4-(6-trifluoromethyl-3-pyridyl)-2-imidazolin-2-yl]-2-pyridone,
5-[(4S,5S)-4-(4-fluorophenyl)-4-(2-fluoro-4-pyridyl)-5-methyl-2-imidazolin-2-yl]-1-methoxy-2-pyridone,
5-[(4R,5S)-4-(4-fluorophenyl)-5-methyl-4-(6-trifluoromethyl-3-pyridyl)-2-imidazolin-2-yl]-1-methoxy-2-pyridone,
5-[(4R,5S)-4-(4-chlorophenyl)-4-(2-fluoro-4-pyridyl)-5-methyl-2-imidazolin-2-yl]-1-methoxy-2-pyridone,
1-difluoromethyl-5-[(4S,5S)-4-(4-fluorophenyl)-4-(6-fluoro-3-pyridyl)-5-methyl-2-imidazolin-2-yl]-3-methyl-2-pyridone,
1-difluoromethyl-5-[(4R,5S)-4-(4-fluorophenyl)-4-(6-fluoro-3-pyridyl)-5-methyl-2-imidazolin-2-yl]-3-methyl-2-pyridone,
1-difluoromethyl-5-[(4S,5S)-4-(4-fluorophenyl)-4-(6-fluoro-3-pyridyl)-5-methyl-2-imidazolin-2-yl]-3-methoxy-2-pyridone,
1-difluoromethyl-5-[(4R,5S)-4-(4-fluorophenyl)-4-(6-fluoro-3-pyridyl)-5-methyl-2-imidazolin-2-yl]-3-methoxy-2-pyridone,
5-[(5S)-4,4-bis(4-fluorophenyl)-5-methyl-2-imidazolin-2-yl]-1-methoxy-2-pyridone,
1-difluoromethyl-5-[(4S,5S)-4-(6-cyclopropyl-3-pyridyl)-4-(4-fluorophenyl)-5-methyl-2-imidazolin-2-yl]-2-pyridone,
5-[(4S,5S)-4-(6-cyclopropyl-3-pyridyl)-4-(4-fluorophenyl)-5-methyl-2-imidazolin-2-yl]-1-ethyl-2-pyridone,
5-[(4S,5S)-4-(4-chlorophenyl)-4-(6-fluoro-3-pyridyl)-5-methyl-2-imidazolin-2-yl]-1-methoxy-2-pyridone,
5-[(4S,5S)-4-(6-fluoro-3-pyridyl)-5-methyl-4-(4-trifluoro-methylphenyl)-2-imidazolin-2-yl]-1-methoxy-2-pyridone,
5-[(4R,5S)-4-(4-fluorophenyl)-4-(2-fluoro-4-pyridyl)-5-methyl-2-imidazolin-2-yl]-1-methoxy-2-pyridone,
1-cyclopropyl-5-[(4R,5S)-4-(4-fluorophenyl)-4-(6-fluoro-3-pyridyl)-5-methyl-2-imidazolin-2-yl]-2-pyridone,
1-cyclopropyl-5-[(4R,5S)-4-(4-fluorophenyl)-4-(2-fluoro-4-pyridyl)-5-methyl-2-imidazolin-2-yl]-2-pyridone,
1-ethyl-5-[(5S)-4,4-bis(6-fluoro-3-pyridyl)-5-methyl-2-imidazolin-2-yl]-2-pyridone,
5-[(5S)-4,4-bis(6-fluoro-3-pyridyl)-5-methyl-2-imidazolin-2-yl]-1-difluoromethyl-2-pyridone,
1-cyclopropyl-5-[(4S,5S)-4-(4-fluorophenyl)-4-(2-fluoro-4-pyridyl)-5-methyl-2-imidazolin-2-yl]-2-pyridone,
1-difluoromethyl-3-ethyl-5-[(4S,5S)-4-(4-fluorophenyl)-4-(6-fluoro-3-pyridyl)-5-methyl-2-imidazolin-2-yl]-2-pyridone,
1-difluoromethyl-3-ethyl-5-[(4R,5S)-4-(4-fluorophenyl)-4-(6-fluoro-3-pyridyl)-5-methyl-2-imidazolin-2-yl]-2-pyridone,
1-difluoromethoxy-5-[(4S,5S)-4-(4-fluorophenyl)-4-(6-fluoro-3-pyridyl)-5-methyl-2-imidazolin-2-yl]-2-pyridone,
5-[(4R,5S)-4-(6-difluoromethyl-3-pyridyl)-4-(4-fluorophenyl)-5-methyl-2-imidazolin-2-yl]-1-methoxy-2-pyridone,
5-[(4S,5S)-4-(6-difluoromethyl-3-pyridyl)-4-(4-fluorophenyl)-5-methyl-2-imidazolin-2-yl]-1-methoxy-2-pyridone,
1-difluoromethoxy-5-[(4R,5S)-4-(4-fluorophenyl)-4-(6-fluoro-3-pyridyl)-5-methyl-2-imidazolin-2-yl]-methoxy-2-pyridone,
1-difluoromethyl-3-ethyl-5-[(4R,5S)-4-(4-fluorophenyl)-4-(2-fluoro-4-pyridyl)-5-methyl-2-imidazolin-2-yl]-2-pyridone,
1-difluoromethyl-5-[(4S,5S)-4-(4-fluorophenyl)-4-(6-fluoro-3-pyridyl)-5-methyl-2-imidazolin-2-yl]-3-hydroxy-2-pyridone,
1-difluoromethyl-5-[(4S,5S)-4-(4-fluoro-3-hydroxyphenyl)-4-(6-fluoro-3-pyridyl)-5-methyl-2-imidazolin-2-yl]-2-pyridone, or
1-difluoromethyl-5-[(4S,5R)-4-(4-fluorophenyl)-4-(6-fluoro-3-pyridyl)-5-hydroxymethyl-2-imidazolin-2-yl]-2-pyridone and the like.

Among the above compounds, the preferable compounds are, for example,
1-difluoromethyl-5-[(4S,5S)-4-(4-fluorophenyl)-4-(6-fluoro-3-pyridyl)-5-methyl-2-imidazolin-2-yl]-2-pyridone,
1-ethyl-5-[(4S,5S)-4-(4-fluorophenyl)-4-(6-fluoro-3-pyridyl)-5-methyl-2-imidazolin-2-yl]-2-pyridone,
5-[(4S,5S)-4-(4-fluorophenyl)-4-(6-fluoro-3-pyridyl)-5-methyl-2-imidazolin-2-yl]-1-propyl-2-pyridone,
5-[(4S,5S)-4-(4-fluorophenyl)-4-(6-fluoro-3-pyridyl)-5-methyl-2-imidazolin-2-yl]-1-isopropyl-2-pyridone,
1-difluoromethyl-5-[(4R,5S)-4-(4-fluorophenyl)-5-methyl-4-(6-trifluoromethyl-3-pyridyl)-2-imidazolin-2-yl]-2-pyridone,
1-difluoromethyl-5-[(4S,5S)-4-(4-fluorophenyl)-5-methyl-4-(6-trifluoromethyl-3-pyridyl)-2-imidazolin-2-yl]-2-pyridone,
1-ethyl-5-[(4R,5S)-4-(4-fluorophenyl)-5-methyl-4-(6-trifluoromethyl-3-pyridyl)-2-imidazolin-2-yl]-2-pyridone,
1-ethyl-5-[(4S,5S)-4-(4-fluorophenyl)-5-methyl-4-(6-trifluoromethyl-3-pyridyl)-2-imidazolin-2-yl]-2-pyridone,
5-[(4R,5S)-4-(4-fluorophenyl)-5-methyl-4-(6-trifluoromethyl-3-pyridyl)-2-imidazolin-2-yl]-1-propyl-2-pyridone,
5-[(4S,5S)-4-(4-fluorophenyl)-5-methyl-4-(6-trifluoromethyl-3-pyridyl)-2-imidazolin-2-yl]-1-propyl-2-pyridone,
3-chloro-1-ethyl-5-[(4R,5S)-4-(4-fluorophenyl)-5-methyl-4-(6-trifluoromethyl-3-pyridyl)-2-imidazolin-2-yl]-2-pyridone,
3-chloro-1-ethyl-5-[(4S,5S)-4-(4-fluorophenyl)-5-methyl-4-(6-trifluoromethyl-3-pyridyl)-2-imidazolin-2-yl]-2-pyridone, 1-difluoromethyl-5-[(4R,5S)-4-(4-fluorophenyl)-4-(6-fluoro-3-pyridyl)-5-methyl-2-imidazolin-2-yl]-2-pyridone, 1-difluoromethyl-5-[(4R,5S)-4-(4-chlorophenyl)-4-(2-fluoro-4-pyridyl)-5-methyl-2-imidazolin-2-yl]-2-pyridone, 1-difluoromethyl-5-[(4S,5S)-4-(4-chlorophenyl)-4-(2-fluoro-4-pyridyl)-5-methyl-2-imidazolin-2-yl]-2-pyridone, 1-ethyl-5-[(4R,5S)-4-(4-chlorophenyl)-4-(2-fluoro-4-pyridyl)-5-methyl-2-imidazolin-2-yl]-2-pyridone, 1-ethyl-5-[(4S,5S)-4-(4-chlorophenyl)-4-(2-fluoro-4-pyridyl)-5-methyl-2-imidazolin-2-yl]-2-pyridone, 1-ethyl-3-fluoro-5-[(4S,5S)-4-(4-fluorophenyl)-4-(6-fluoro-3-pyridyl)-5-methyl-2-imidazolin-2-yl]-2-pyridone, 1-ethyl-3-fluoro-5-[(4R,5S)-4-(4-fluorophenyl)-5-methyl-4-(6-trifluoromethyl-3-pyridyl)-2-imidazolin-2-yl]-2-pyridone, 1-ethyl-3-fluoro-5-[(4S,5S)-4-(4-fluorophenyl)-5-methyl-4-(6-trifluoromethyl-3-pyridyl)-2-imidazolin-2-yl]-2-pyridone, 3-ethyl-5-[(4S,5S)-4-(4-fluorophenyl)-4-(6-fluoro-3-pyridyl)-5-methyl-2-imidazolin-2-yl]-1-methyl-2-pyridone, 1-difluoromethyl-5-[(4R,5S)-4-(6-difluoromethyl-3-pyridyl)-4-(4-fluorophenyl)-5-methyl-2-imidazolin-2-yl]-2-pyridone, 1-difluoromethyl-5-[(4S,5S)-4-(6-difluoromethyl-3-pyridyl)-4-(4-fluorophenyl)-5-methyl-2-imidazolin-2-yl]-2-pyridone, 5-[(4R,5S)-4-(6-difluoromethyl-3-pyridyl)-4-(4-fluorophenyl)-5-methyl-2-imidazolin-2-yl]-1-ethyl-3-fluoro-2-pyridone, 5-[(4S,5S)-4-(6-difluoromethyl-3-pyridyl)-4-(4-fluorophenyl)-5-methyl-2-imidazolin-2-yl]-1-ethyl-3-fluoro-2-pyridone, 5-[(4S,5S)-4-(4-fluorophenyl)-4-(6-fluoro-3-pyridyl)-5-methyl-2-imidazolin-2-yl]-1-methoxy-2-pyridone, 5-[(4R,5S)-4-(4-fluorophenyl)-5-methyl-4-(6-trifluoromethyl-3-pyridyl)-2-imidazolin-2-yl]-1-methoxy-2-pyridone, 1-difluoromethyl-3-ethyl-5-[(4S,5S)-4-(4-fluorophenyl)-4-(6-fluoro-3-pyridyl)-5-methyl-2-imidazolin-2-yl]-2-pyridone and the like.

The processes for producing the compounds of the present invention are illustrated as follows.

The compounds (I) of the present invention can be prepared, for example, by the following Production Processes or the methods shown in Examples, but Manufacturing methods of the compounds (I) of the present invention are not limited to these embodiments.

Production Process 1

The compound of the formula (I) can be prepared by reacting a compound of the formula (II):

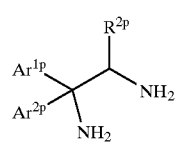

(II)

(wherein $Ar^{1p}$ and $Ar^{2p}$ are independently aryl or heteroaryl, any of which is optionally substituted by a substituent selected from the group consisting of cyano, halogen, nitro, lower alkyl, halo-lower alkyl, cyclo-lower alkyl, cyclo (lower alkyl)-lower alkyl, lower alkenyl, di-lower alkylamino, lower alkoxy, halo-lower alkoxy, aryloxy, heteroaryloxy, lower alkylthio, formyl, lower alkanoyl, lower alkoxycarbonyl, di-lower alkylcarbamoyl, lower alkylsulfonyl, arylsulfonyl, aryl, heteroaryl, optionally protected hydroxy-lower alkyl, optionally protected lower alkylamino, optionally protected lower alkanoylamino, optionally protected lower alkylsulfonylamino, optionally protected arylsulfonylamino, optionally protected hydroxy, optionally protected carboxyl, optionally protected carbamoyl and optionally protected lower alkylcarbamoyl;

$R^{2p}$ is lower alkyl, cyclo-lower alkyl, cyclo(lower alkyl)-lower alkyl or lower alkoxy, any of which is optionally substituted by a substituent selected from the group consisting of halogen, di-lower alkylamino, lower alkoxy, formyl, lower alkoxycarbonyl, di-lower alkylcarbamoyl, optionally protected lower alkylamino, optionally protected lower alkanoylamino, optionally protected hydroxy and optionally protected lower alkylcarbamoyl)

with a compound of the formula (III):

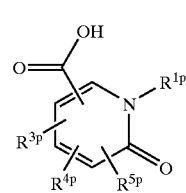

(III)

(wherein $R^{1p}$ is lower alkyl, cyclo-lower alkyl, cyclo(lower alkyl)-lower alkyl or lower alkoxy, any of which is optionally substituted by a substituent selected from the group consisting of halogen, di-lower alkylamino, lower alkoxy, formyl, lower alkoxycarbonyl, di-lower alkylcarbamoyl, optionally protected lower alkylamino, optionally protected lower alkanoylamino, optionally protected hydroxy and optionally protected lower alkylcarbamoyl;

$R^{3p}$, $R^{4p}$ and $R^{5p}$ are independently hydrogen, cyano, halogen or optionally protected hydroxy, or lower alkyl, lower alkoxy or lower alkylthio, the last three groups being optionally substituted by a substituent selected from the group consisting of halogen, di-lower alkylamino, lower alkoxy, formyl, lower alkoxycarbonyl, di-lower alkylcarbamoyl, optionally protected lower alkylamino, optionally protected lower alkanoylamino, optionally protected hydroxy and optionally protected lower alkylcarbamoyl), subjecting the resulting compound of the formula (IV):

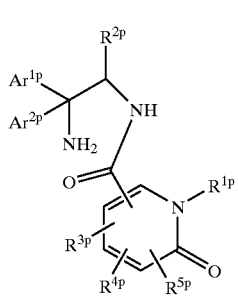

(IV)

(wherein $Ar^{1p}$, $Ar^{2p}$, $R^{1p}$, $R^{2p}$, $R^{3p}$, $R^{4p}$ and $R^{5p}$ have each the same meaning as defined above) to intramolecular ring closure condensation to give a compound of the formula (V):

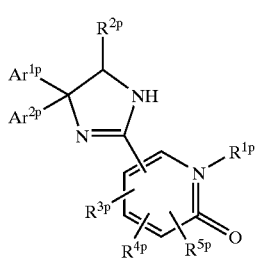

(V)

(wherein $Ar^{1p}$, $Ar^{2p}$, $R^{1p}$, $R^{2p}$, $R^{3p}$, $R^{4p}$ and $R^{5p}$ have each the same meaning as defined above), and optionally removing the protecting group(s) from the compound (V).

In the above reaction, when a reactant has an amino, imino, hydroxy, carboxyl or the like which does not participate in the reaction, the reaction may be carried out after protecting the amino, imino, hydroxy or carboxyl with an amino- or imino-protecting group, a hydroxy-protecting group, or a carboxyl-protecting group, followed by the removal of said protecting groups after completion of the reaction.

The "amino- or imino-protecting group" includes, for example, aralkyl (e.g. benzyl, p-methoxybenzyl, 3,4-dimethoxybenzyl, o-nitrobenzyl, p-nitrobenzyl, benzhydryl, trityl); lower alkanoyl (e.g. formyl, acetyl, propionyl, butyryl, pivaloyl); benzoyl; arylalkanoyl (e.g. phenylacetyl, phenoxyacetyl); lower alkoxycarbonyl(e.g. methoxycarbonyl, ethoxycarbonyl, propyloxycarbonyl, tert-butoxycarbonyl); aralkyloxycarbonyl (e.g. benzyloxycarbonyl, p-nitrobenzyloxycarbonyl, phenethyloxycarbonyl); lower alkylsilyl (e.g. trimethylsilyl, tert-butyldimethylsilyl) and the like, among which the preferable examples are acetyl, pivaloyl, benzoyl, ethoxycarbonyl, tert-butoxycarbonyl and the like.

The "hydroxy-protecting group" includes, for example, lower alkylsilyl (e.g. trimethylsilyl, tert-butyldimethylsilyl); lower alkoxymethyl (e.g. methoxymethyl, 2-methoxyethoxymethyl); tetrahydropyranyl; trimethylsilylethoxymethyl; aralkyl (e.g. benzyl, p-methoxybenzyl, 2,3-dimethoxybenzyl, o-nitrobenzyl, p-nitrobenzyl, trityl); and acyl (e.g. formyl, acetyl), among which the preferable examples are methoxymethyl, tetrahydropyranyl, trityl, trimethylsilylethoxymethyl, tert-butyldimethylsilyl, acetyl and the like.

The "carboxyl-protecting group" includes, for example, lower alkyl (e.g. methyl, ethyl, propyl, isopropyl, tert-butyl); halo-lower alkyl (e.g. 2,2,2-trichloroethyl); lower alkenyl (e.g. 2-propenyl); aralkyl (e.g. benzyl, p-methoxybenzyl, p-nitrobenzyl, benzhydryl, trityl) and the like, among which the preferable examples are methyl, ethyl, tert-butyl, 2-propenyl, benzyl, p-methoxybenzyl or benzhydryl and the like.

The reaction between a compound of the formula (II) and a compound of the formula (III) is usually carried out by employing 0.5 moles to excessive mole, preferably 1 mole to 2 moles of compound (III), relative to 1 mole of compound (II).

The reaction is usually carried out in an inert solvent, and preferable examples of such solvent are methylene chloride, chloroform, tetrahydrofuran, dimethylformamide, pyridine, etc., or a mixture thereof and the like.

The above reaction is preferably carried out in the presence of a condensing reagent, and the examples of such condensing reagents are N,N'-dicyclohexylcarbodiimide, N,N'-diisopropylcarbodiimide, 1-(3-dimethylaminopropyl)-3-ethylcarbodiimide, 1-(3-dimethylaminopropyl)-3-ethylcarbodiimide hydrochloride, benzotriazol-1-yloxy-tris-(dimethylamino)phosphonium hexafluorophosphate, benzotriazol-1-yloxy-tris-pyrrolidinophosphonium hexafluorophosphate, diphenylphosphoric azide, 1,1-carbonyldiimidazole and the like.

Such condensing reagents can be usually used in 1 mole to excess moles, preferably 1 to 3 moles, relative to 1 mole of a compound of the formula (II).

The reaction temperature is usually from −20° C. to the boiling point of the solvent used in the reaction, preferably from −0° C. to 60° C.

The reaction time is usually 30 minutes to 3 days, preferably 1 to 24 hours.

A usual workup procedure is applied after completion of the reaction to obtain a crude product of a compound of the formula (IV). The resulting compound of the formula (IV) may be, with or without purification according to the conventional manner, subjected to intramolecular ring closure condensation.

The intramolecular ring closure condensation for preparing a compound of the formula (V) from the compound (IV) is usually carried out in the presence of an inert solvent or without any solvent.

Preferred examples of such inert solvents are ethanol, propanol, butanol, pentanol, 1,4-dioxane, dimethoxyethane, dimethylformamide, dimethyl sulfoxide, benzene, toluene, xylene, etc., and a mixture thereof and the like.

The reaction temperature is usually from room temperature to the boiling point of the solvent used, preferably from 80° C. to 190° C.

The reaction time is usually 1 hour to 7 days, preferably 2 hours to 3 days.

The above ring closure may be carried out in the presence of a dehydrating reagent or a catalytic-amount of Lewis acid. The dehydrating reagent includes, for example, phosphorus oxychloride, phosphorus pentachloride, polyphosphoric acid, thionyl chloride and the like. As the Lewis acid, there are exemplified by scandium trifluoromethanesulfonate, yttrium trifluoromethanesulfonate, lanthanum trifluoromethanesulfonate, lanthanide trifluoromethanesulfonate and the like. Preferably the ring closure is carried out without any solvent, or in the presence of a solvent such as methylene chloride, chloroform, benzene, toluene, xylene, etc. or a mixture thereof.

The amount of the dehydrating agent used is usually 1 mole to excessive mole, preferably 2 to 10 moles, relative to 1 mole of a compound of the formula(IV), and that of the Lewis acid is 1 to 50 mole %, preferably 5 to 30 mole %.

In general, the reaction temperature is preferably from room temperature to the boiling point of the solvent used.

The reaction time is from one hour to 7 days, preferably from 5 hours to 3 days.

The above ring closure may also be carried out while removing the generated water with a Dean-Stark water separator, and it is preferable to conduct the reaction in a solvent such as benzene, toluene, xylene or a mixture thereof and the like.

In general, the reaction temperature is preferably from room temperature to the boiling point of the solvent used.

The reaction time is usually from one hour to 7 days, preferably from 2 hours to 3 days.

Usual workup procedures are applied after completion of the reaction to obtain a crude product of a compound of the formula (V). The resulting compound of the formula (V) is, with or without purification according to the common method, subjected to optional, proper combination of removal of the protecting group(s) for the amino, imino, hydroxy and carboxyl, thereby a compound of the formula (I) can be prepared.

Although the method for the removal of said protecting groups depends upon the kinds of the protecting groups, the stability of a desired compound (I), etc., it is carried out by, for example, a solvolysis using an acid or a base, that is, a method wherein for example 0.01 mole to a large excess of an acid, preferably trifluoroacetic acid, formic acid, hydrochloric acid and the like, or an equivalent mole to a large excess of a base, preferably potassium hydroxide, calcium hydroxide and the like is acted; a chemical reduction using a metal hydride complex; or a catalytic reduction using a palladium-carbon catalyst, a Raney-nickel catalyst, etc., according to, for example, a method described in the literature (Protective Groups in Organic Synthesis, T. W. Greene, John Wiley & Sons, (1981)) or its similar methods.

Production Process 2

The compound of the formula (I) can be prepared by reacting a compound of the formula (II):

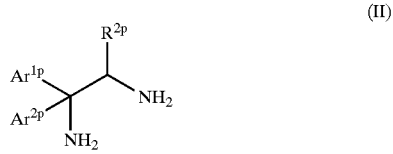

(wherein $Ar^{1p}$, $Ar^{2p}$ and $R^{2p}$ have each the same meaning as defined above) with an acid addition salt of a compound of the formula (VI):

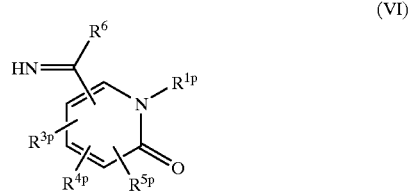

(wherein $R^6$ is amino or lower alkoxy, and $R^{1p}$, $R^{3p}$, $R^{4p}$ and $R^{5p}$ have each the same meaning as defined above)to give a compound of the formula (V):

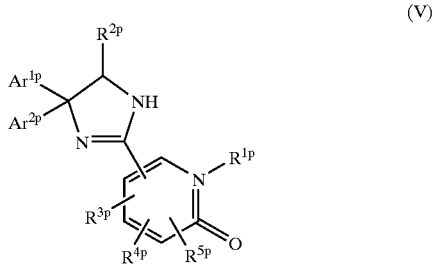

(wherein $Ar^{1p}$, $Ar^{2p}$, $R^{1p}$, $R^{2p}$, $R^{3p}$, $R^{4p}$ and $R^{5p}$ have each the same meaning as defined above), and optionally removing the protecting group(s) from the compound (V).

A preferable example of the acid addition salt of the compound (VI) is hydrochloride and the like.

The reaction between a compound of the formula (II) and a compound of the formula (VI) is usually carried out in an inert solvent, and the preferable examples of such solvents are alcohols such as methanol, ethanol, etc., dimethylformamide, dimethyl sulfoxide, etc., or a mixture thereof and the like.

The reaction temperature is usually from −30° C. to 200° C., preferably from 0° C. to 150° C.

The reaction time is usually 30 minutes to 7 days, preferably 2 hours to 5 days.

A compound of the formula (I) can be produced by working up a reaction mixture in the usual way after removal of the said protecting group(s) when the product has a protecting group after completion of the reaction, or by working up the mixture directly in the usual way when the protecting group is absent.

The removal of the protecting group(s) and the workup procedure may be carried out according to the method described in the above Production Process 1.

The compounds of the formula (I) may be readily isolated and purified by the conventional separation technique, and examples of such technique are solvent extraction, recrystallization, column chromatography, preparative thin layer chromatography, HPLC and the like.

These compounds can be converted into the pharmaceutically acceptable salts or esters by the conventional method, and on the contrary, the conversion of the salts or esters into free compounds can also be carried out according to the conventional method.

The compounds of the formulae (II), (III) and (VI) are commercially available, or can be prepared according to the common methods described in literature such as International Patent Publication WO 01/62738 or analogous methods thereto, or the Processes described below or the methods shown in Examples and Reference Examples, optionally employed in combination.

Production Process A

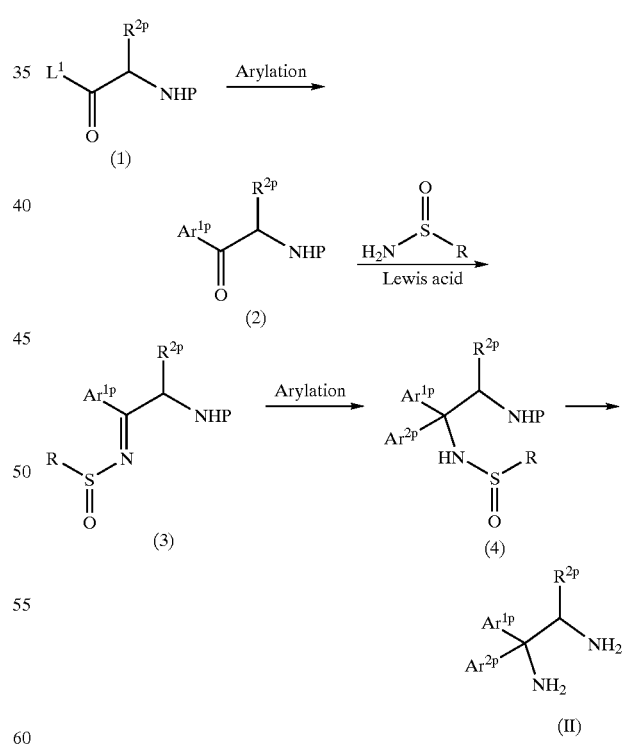

In the above reaction scheme, $L^1$ is hydrogen or a leaving group; P is an amino-protecting group; R is a bulky group; and $Ar^{1p}$, $Ar^{2p}$ and $R^{2p}$ have each the same meaning as defined above.

The present process is a process for preparing a compound of the formula (II).

According to the present process, the compound of the formula (II) can be prepared by the arylation of a compound of the formula (1) to give a compound of the formula (2), converting the carbonyl group of the compound (2) into the sulfinylimide group to give a compound of the formula (3), arylating said compound (3) again to give a compound of the formula (4), and removing the amino-protecting group represented by P and a group represented by —S(=O)—R from said compound (4).

The preferable examples of leaving group represented by $L^1$ include, halogen, lower alkoxy, a group capable of forming an amide such as methoxy(methyl)amide together with the adjacent carbonyl group and the like.

Examples of the amino-protecting group represented by P include those described in Production process 1, and the method described in Production process 1 can also be used for their removal.

The bulky group represented by R means a group constituting steric hindrance in the molecule of compounds, and the examples thereof are secondary alkyl or tertiary alkyl, among which tertiary alkyl, etc. is preferable. More specifically, the examples of such bulky group are isopropyl, sec-butyl and tert-butyl and the like, among which tert-butyl, etc. is preferable.

The step for preparing a compound (2) from a compound (1) is usually carried out by reacting a compound (1) with an organometallic compound such as aryl lithium, aryl magnesium, aryl zinc or aryl copper, wherein said organometallic compound has an aryl moiety represented by $Ar^{1p}$.

The reaction is usually carried out by employing 1 mole to excessive mole, preferably 2 moles to 5 moles of said organometallic compound, relative to 1 mole of the compound (1) in an inert solvent such as ethers (e.g. diethyl ether, tetrahydrofuran, 1,2-dimethoxyethane) or the mixture thereof and the like.

The reaction temperature is usually from $-130°$ C. to the boiling point of the solvent used, preferably from $-100°$ C. to room temperature. The reaction time is usually 30 minutes to 2 days, preferably one hour to one day.

When $L^1$ is hydrogen, a ketone (2) can be prepared by oxidation of an alcohol which is obtained by arylation, wherein the oxidation per se is well known in the field of organic chemistry.

The step of producing the compound (3) from the compound (2) may be carried out according to the common method described in literatures such as Journal of Organic Chemistry, vol. 64, p. 1278 (1999) and similar method thereof, and the like. That is, the compound (3) can be usually prepared by reacting the compound (2) with a sulfinyl amide represented by the following formula:

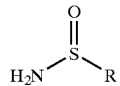

(wherein R has the same meaning as defined above) in the presence of a Lewis acid such as tetraisopropoxy titanium, tetraethoxy titanium, magnesium sulfate, copper sulfide, etc.

The reaction is usually carried out by employing 1 mole to excessive mole, preferably 2 moles to 7 moles of said Lewis acid, and 0.5 moles to excessive mole, preferably 1 mole to 5 moles of sulfinylamide, relative to 1 mole of the compound (2) in an inert solvent such as diethyl ether, tetrahydrofuran, 1,2-dimethoxyethane, toluene, benzene, dichloromethane, 1,2-dichloroethane, chloroform, acetonitrile, etc., and the mixture thereof, etc.

The reaction temperature is usually from $0°$ C. to the boiling point of the solvent used, preferably from $0°$ C. to $100°$ C. The reaction time is usually 30 minutes to 3 days, preferably one hour to 24 hours.

The step of producing the compound (4) from the compound (3) can be usually carried out by reacting the compound (3) with an organometallic compound such as aryl lithium, aryl magnesium, aryl zinc or aryl copper, etc., wherein said organometallic compound has an aryl moiety represented by $Ar^{2p}$.

The reaction is usually carried out by employing 0.5 moles to excessive mole, preferably 1 mole to 3 moles of said organometallic compound, relative to 1 mole of the compound (3) at $-130°$ C. to the boiling point of the solvent used, preferably $-110°$ C. to room temperature in an inert solvent such as diethyl ether, tetrahydrofuran, 1,2-dimethoxyethane, toluene, benzene, dichloromethane, etc., and the mixture thereof, etc. for 5 minutes to 24 hours, preferably 15 minutes to 2 hours.

Alternatively, the compound (4) can be prepared by activating the compound (3) with a Lewis acid such as trimethylaluminum, triethylaluminum, triisopropylaluminum, boron trifluoride-ether complex, zinc chloride, tin chloride and the like, followed by subjecting to the above reaction with the organometallic compound. The reaction is usually carried out by employing 0.5 moles to excessive mole, preferably 1 mole to 3 moles of said Lewis acid, relative to 1 mole of the compound (3) at $-100°$ C. to the boiling point of the solvent used, preferably $-78°$ C. to room temperature in an inert solvent such as diethyl ether, tetrahydrofuran, 1,2-dimethoxyethane, toluene, benzene, dichloromethane, etc., and the mixture thereof, etc. for 5 minutes to 24 hours, preferably 15 minutes to 3 hours.

The reaction between the Lewis acid complex obtained in the above process and said organometallic compound can be carried out by employing 1 mole to excessive mole, preferably 2 moles to 5 moles of said organometallic compound, relative to the compound (3) in an inert solvent such as diethyl ether, tetrahydrofuran, 1,2-dimethoxyethane, toluene, benzene, dichloromethane, etc., and the mixture thereof, etc.

The reaction temperature is usually from $-130°$ C. to the boiling point of the solvent used, preferably from $-100°$ C. to room temperature. The reaction time is usually 30 minutes to 2 days, preferably one hour to 24 hours.

After that, the amino-protecting group represented by P and a group represented by —S(=O)—R are removed from the compound (4), thereby the compound of the formula(II) can be prepared.

Although the removal of amino-protecting group represented by P depends upon the kinds of the protecting groups, the stability of the desired compound (II), etc., it is carried out by, for example, a solvolysis using an acid or a base, that is, a method wherein for example 0.01 mole to a large excess of an acid, preferably trifluoroacetic acid, formic acid, hydrochloric acid and the like, or an equivalent mole to a large excess of a base, preferably potassium hydroxide, calcium hydroxide and the like is acted; a chemical reduction using a metal hydride complex; or a catalytic reduction using a palladium-carbon catalyst, a Raney-nickel catalyst, etc.; and the like, according to, for example, a method described in the literature (Protective Groups in Organic Synthesis, T. W. Greene, John Wiley & Sons, (1981)) or its similar method.

The removal of the group represented by —S(=O)—R may be carried out by reacting it with hydrogen halide such as hydrogen chloride, hydrogen bromide, hydrogen iodide, etc. in a solvent such as water, methanol, ethanol, propanol, dioxane, ethyl acetate, acetonitrile, dimethylformamide, dimethyl sulfoxide, etc., and the mixture thereof. The concentration of hydrogen halide used in the reaction is usually 1 N to 20 N, preferably 2 N to 10 N. The reaction temperature is usually from −20° C. to the boiling point of the solvent used, preferably from 0° C. to 40° C.

The stereo configuration of the carbon atom to which $R^{2p}$ is attached is retained during a series of above processes for preparing the compound (II) from the compound (1). Accordingly, when $Ar^{1p}$ and $Ar^{2p}$ are the same each other in the desired compounds, the use of an optically active amino acid derivative as the starting compound represented by the formula (1) enable the production of a corresponding optically active compound (II). In the case where $Ar^{1p}$ and $Ar^{2p}$ are different from each other in the desired compounds, a corresponding optically active compound (II) can also be prepared because of the high diastereoselectivity in the reaction of producing the compound (4) from the compound (3).

The compounds of the formula (I) and an organometallic compound used for arylation are commercially available, or can be prepared according to the common methods or the methods shown in Examples and Reference Examples, optionally employed in combination.

Production Process B

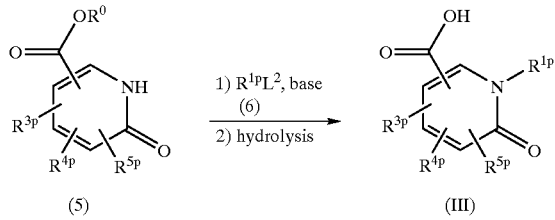

(5)     (III)

In the above reaction scheme, $L^2$ is a leaving group; $R^0$ is an ester residue; $R^{1p}$, $R^{3p}$, $R^{4p}$ and $R^{5p}$ have each the same meaning as defined above.

The present process is a process for preparing a compound of the formula (III).

According to the present process, the compound of the formula (III) can be prepared by reacting a compound of the formula (5) with a compound of the formula (6) in the presence of a base so that a group represented by $R^{1p}$ is introduced on the nitrogen atom of the pyridone ring of the compound (5), followed by hydrolysis of said ester compound.

The preferable examples of the leaving group represented by $L^2$ are halogen, sulfonate and the like.

There is no particular limitation to the ester residue represented by $R^0$ so long as it is hydrolysable under such condition that other functional groups not participating in the reaction are not undesirably affected during the hydrolysis. The preferable examples of such ester residue are lower alkyl (e.g. methyl, ethyl, tert-butyl), allyl, benzyl and the like, any of which may have an appropriate substituent not affecting the reaction undesirably.

The preferable examples of the base used in the reaction are sodium hydride, butyllithium, potassium carbonate, cesium fluoride and the like.

The reaction between the compound of the formula (5) and the compound of the formula (6) may be carried out according to the common methods described in literatures such as Tetrahedron Lett., vol. 36, p. 8917 (1995); Synlett, p. 845 (1995), or similar methods thereof, etc.

The reaction is usually carried out by employing 1 mole to excessive mole, preferably 2 moles to 5 moles of the compound (6), relative to 1 mole of the compound (5) in an solvent such as methanol, ethanol, tetrahydrofuran, acetonitrile, dimethylformamide, dimethyl sulfoxide, N-methylpyrrolidone, etc. and the mixture thereof, etc.

The reaction temperature is usually from −78° C. to the boiling point of the solvent used, preferably from 0° C. to 100° C. The reaction time is usually 5 minutes to 2 days, preferably 30 minutes to one day. In the above reaction, an additive such as lithium bromide may be optionally added, and the additive is employed by 1 mole to excessive mole, preferably 2 moles to 5 moles, relative to 1 mole of the compound of the formula (5).

The ester obtained is hydrolyzed to a carboxylic acid by an ester hydrolysis method well known per se in the field of organic chemistry, thereby a compound of the formula (III) can be prepared.

The compounds of the formulae (5) and (6) are commercially available, or can be prepared according to the common methods or analogous methods thereto, or the methods shown in Examples and Reference Examples, optionally employed in combination.

The compound of the formula (III-1):

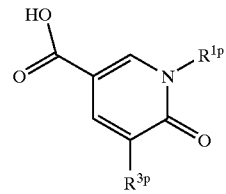

(III-1)

(wherein $R^{1p}$ and $R^{3p}$ have each the same meaning as defined above) is a novel compound which has never been disclosed in literatures.

The specific examples of the compound of the formula (III-1) are, 1-ethyl-2-pyridone-5-carboxylic acid,
1-difluoromethyl-2-pyridone-5-carboxylic acid,
1-propyl-2-pyridone-5-carboxylic acid,
1-isopropyl-2-pyridone-5-carboxylic acid,
1-(2,2-difluoroethyl)-2-pyridone-5-carboxylic acid,
3-chloro-1-methyl-2-pyridone-5-carboxylic acid,
3-chloro-1-ethyl-2-pyridone-5-carboxylic acid,
1-ethyl-3-fluoro-2-pyridone-5-carboxylic acid,
1,3-dimethyl-2-pyridone-5-carboxylic acid,
1-ethyl-3-methyl-2-pyridone-5-carboxylic acid,
1-ethyl-3-methoxy-2-pyridone-5-carboxylic acid,
1-difluoromethyl-3-methyl-2-pyridone-5-carboxylic acid,
1-difluoromethyl-3-ethyl-2-pyridone-5-carboxylic acid,
1-methoxy-2-pyridone-5-carboxylic acid,
1-ethoxy-2-pyridone-5-carboxylic acid,
1-difluoromethoxy-2-pyridone-5-carboxylic acid,
1-difluoromethyl-3-methoxy-2-pyridone-5-carboxylic acid,
1-cyclopropyl-2-pyridone-5-carboxylic acid, and the like.

The utility of compounds of the present invention as a medicament is proved by the following pharmacological tests.

Pharmacological Test 1 (NPY Binding Inhibition Test)

cDNA sequence encoding human NPY Y5 receptor (c.f. International patent publication number WO96/16542) was cloned into expression vectors pcDNA3, pRc/RSV (made by Invitrogen Inc.) and pCI-neo (made by Promega Inc.). The expression vectors thus obtained were transfected to host cells COS-7, CHO and LM(tk−) (American Type Culture Collection) by cationic lipid method (Proceedings of the National Academy of Sciences of the United States of America, vol. 84: p. 7413(1987)) to give NPY Y5 receptor expression cells.

A membrane sample prepared from the cells which expressed NPY Y5 receptor was incubated together with a test compound and [$^{125}$I]peptideYY (made by NEN) (20,000 cpm) in an assay buffer (25 mM Tris buffer, pH7.4, containing 10 mM magnesium chloride, 1 mM phenylmethylsulfonyl fluoride, 0.1% bacitracin and 0.5% bovine serum albumin) at 25° C. for 2 hours, then filtered through a glass filter GF/C and washed with 5 mM Tris buffer (pH7.4) containing 0.3% BSA. The radioactivity of the cake on the glass filter was measured. Non-specific binding was measured in the presence of 1 μM peptide YY, and a 50% Inhibitory Concentration ($IC_{50}$) of the test compound against specific peptideYY binding was determined (Endocrinology, vol. 131: p. 2090(1992)). The results are shown in Table 1.

TABLE 1

| compounds | $IC_{50}$ (nM) |
| --- | --- |
| Example 1-1 | 2.8 |
| Example 1-2 | 2.9 |
| Example 1-5 | 3.8 |
| Example 1-6 | 3.8 |
| Example 1-7 | 2.7 |
| Example 1-8 | 2.1 |
| Example 1-9 | 1.5 |
| Example 1-11 | 2.3 |
| Example 1-20 | 2.2 |
| Example 1-21 | 2.7 |
| Example 1-23 | 2.8 |
| Example 1-25 | 2.9 |
| Example 1-29 | 2.9 |
| Example 1-39 | 2.6 |
| Example 1-42 | 2.8 |
| Example 1-45 | 2.8 |
| Example 1-47 | 2.9 |
| Example 1-53 | 2.5 |
| Example 1-70 | 2.9 |

As shown above, the compounds of this invention potently inhibited peptideYY (NPY analogue) binding to NPY Y5 receptors.

Pharmacological Test 2 (Antagonistic Effect on D-Trp$^{34}$NPY-induced Feeding Behavior)

A chronic guide cannula (26 gauge, length 11 mm) was inserted stereotaxicly into the third cerebral ventricle of male SD rats (7–8 weeks old, 200–300 g) anesthetized with ketamine/xylazine (single intraperitoneal administration of 74 and 11 mg/kg) and fixed by dental resin. The tip of the guide cannula was located 2.2 mm posterior to bregma, 8 mm ventral to the skull surface, and on the median line. After about 1-week recovery period, D-Trp$^{34}$NPY (NPY analogue, 1 μg/0.4 μL/head, artificial cerebrospinal fluid containing 0.05% bovine serum albumin) was injected into the third ventricle. A test compound suspended in 0.5% aqueous methylcellulose solution was administered orally 2 hours before the administration of D-Trp$^{34}$NPY, and the food consumption was measured 2 hours after the administration of D-Trp$^{34}$NPY.

The results revealed that 10 mg/kg of the compound of this invention significantly suppressed the increase in food consumption induced by D-Trp$^{34}$NPY which was administered to the third ventricle.

Pharmacological Test 3 (Pharmacokinetics Test)

A test compound was orally or intravenously administered to male SD rats (7–10 weeks old, 200–400 g) under the overnight fasting condition. About 100 μL of blood was collected from the tail vein by heparinized capillary at designated time. The blood was centrifuged (4° C., 6,000 r.p.m., 10 minutes) to obtain the plasma. 3-fold amount of ethanol containing an internal standard was added to plasma. The mixture was stirred, allowed to stand at −20° C. for 20 minutes, and then centrifuged (4° C., 10,000 r.p.m., 10 minutes). The supernatant was analyzed by LC/MS/MS, and the concentration of the test compound in the plasma was measured using a relative calibration curve.

The results revealed that, for example, the bioavailability of the compound of Examples 1–7 was 94% and its half-life in the plasma was 8.5 hours.

Pharmacological Test 4 (Brain/cerebrospinal Fluid Transport Test)

A test compound was orally or intravenously administered to male SD rats (7–10 weeks old, 200–400 g), and whole blood was collected from the abdominal aorta using a heparin-treated syringe under the ether anesthesia at designated time. Then, the head skin was cut out, and a dental 30G needle was inserted between the cervical vertebrae, and it was further inserted into the cavum subarachnoideale. After 50 to 100 μL cerebrospinal fluid had been collected by a 1 ml-syringe through a tube connected to dental 30G needle, the brain was extracted. The blood sample was centrifuged (4° C., 6,000 r.p.m., 10 minutes) to obtain the plasma. 3-fold amount of ethanol containing an internal standard was added, and stirred. The brain sample was homogenized after addition of 2 ml water, an aliquot of the homogenate was taken and 3-fold amount of ethanol containing an internal standard was added, and stirred. The cerebrospinal fluid was stirred after adding 3-fold amount of ethanol containing an internal standard. These samples were allowed to stand at −20° C. for 20 minutes, and then centrifuged (4° C., 12,000 g, 10 minutes). The supernatant was analyzed by LC/MS/MS, and the concentration of the test compound in the plasma, brain, and cerebrospinal fluid were measured by the method using a relative calibration curve.

The results revealed that, for example, concentrations of the compounds of Example 1–7 in the brain, cerebrospinal fluid and plasma were 2.48 nmol/g, 0.15 μM and 3.17 μM, respectively, 2 hours after oral administration (10 mg/kg).

The compounds of the formula (I) can be administered orally or parenterally and, by formulating into a suitable administrable form, may be administered as a therapeutic agent for various diseases, including, for example, cardiovascular disorders such as angina, acute or congestive heart failure, myocardial infarction, hypertension, nephropathy, electrolyte abnormality, vasospasm, arteriosclerosis, etc., central nervous system disorders such as bulimia, depression, anxiety, seizure, epilepsy, dementia, pain, alcoholism, drug withdrawal, circadian rhythm disorders, schizophrenia, memory impairment, sleep disorders, cognitive impairment, etc., metabolic diseases such as obesity, diabetes, hormone abnormality, hypercholesterolemia, hyperlipidemia, gout, fatty liver, etc., genital or reproductive disorders such as infertility, preterm labor, sexual dysfunction, etc., gastrointestinal disorders, respiratory disorders, inflammatory diseases or glaucoma, and the like, also for example, atherosclerosis, hypogonadism, hyperandrogenism, polycystic ovary syndrome, hirsutism, gastro-intestinal motility disorder, obesity-related gastro-esophageal reflux, obesity hypoventilation (Pickwickian syndrome), sleep apnea, inflammation, systemic inflammation of the vasculature, osteoarthritis, insulin resistance, bronchoconstriction, alcohol preference, metabolic syndrome, Alzheimer's disease, cardiac hypertrophy, left ventricular hypertrophy, hypertriglyceridemia, low HDL cholesterol, cardiovascular disorders such as coronary heart disease (CHD), cerebrovascular disease, stroke, peripheral vascular disease, sudden death, etc., gallbladder diseases, cancer (breast, endometrial, colon), breathlessness, hyperuricemia, impaired fertility, low back pain, or increased anesthetic risk, and the like. In clinical use, the compounds of this invention may be administered after being formulated, together with pharmaceutically acceptable additives, into an appropriate preparation according to the mode of administration. As for said additives, those which are usually used in the field of pharmaceutical formulation, for example, gelatin, lactose, sucrose, titanium oxide, starch, crystalline cellulose, hydroxypropyl methylcellulose, carboxymethylcellulose, corn starch, microcrystalline wax, white petrolatum, magnesium methasilicate aluminate, anhydrous calcium phosphate, citric acid, trisodium citrate, hydroxypropyl cellulose, sorbitol, sorbitan fatty acid ester, polysorbate, sucrose fatty acid ester, polyoxyethylene, hydrogenated castor oil, polyvinylpyrrolidone, magnesium stearate, light silicic anhydride, talc, vegetable oil, benzyl alcohol, gum arabic, propylene glycol, polyalkylene glycol, cyclodextrin or hydroxypropyl cyclodextrin, etc. may be used.

The formulations prepared by mixing the compound of the present invention with said additives include, for example, solid preparations (e.g. tablets, capsules, granules, powder, suppositories); or liquid preparations (e.g. syrups, elixirs, injections). Such preparations may be formulated according to the techniques well-known in the art of pharmaceutical formulation. Liquid preparations may be in the form of preparations which are dissolved or suspended in water or other appropriate media when used. In the case of injectable preparations in particular, they may be dissolved or suspended in physiological saline or glucose solution if necessary, optionally together with a buffer and a preservative.

When compounds of this invention are used clinically, for example, a daily dose for an adult is 0.01–100 mg/kg, preferably 0.03–1 mg/kg with simultaneous or divided administration when administered orally, and 0.001–10 mg/kg, preferably 0.001–0.1 mg/kg, more preferably 0.01–0.1 mg/kg with simultaneous or divided administration when administered parenterally, though the dose and the frequency of dosage may vary depending upon the sex, age, body weight, the degree of symptoms and the kind and range of the desired treatment effects.

An ordinarily skilled physician, veterinarian or clinician can readily determine and prescribe the effective amount of the drug required to prevent, suppress or arrest the progress of diseases.

All the said preparations may contain 1.0 to 100 wt. %, preferably 1.0 to 60 wt. % of compounds of the present invention and may also contain other therapeutically effective compounds.

The compounds of the present invention can be used in combination with other agents useful for treating metabolic disorders and/or eating disorders. The individual component of such combinations can be administered separately at different times or concurrently in divided or single combination forms during the course of therapy. The present invention is therefore to be understood as embracing all such regimes of simultaneous or divided administration and the term "administering" is to be interpreted accordingly. The scope of combinations of the compounds of this invention with other agents useful for treating metabolic disorders and/or eating disorders includes in principle any combination of any pharmaceutical composition useful for treating metabolic disorders and/or eating disorders.

Diabetes is caused by multiple factors and is most simply characterized by elevated levels of plasma glucose (hyperglycemia) in the fasting state. There are two generally recognized forms of diabetes: type 1 diabetes, or insulin-dependent diabetes mellitus (IDDM), in which patients produce little or no insulin, the hormone which regulates glucose utilization, and type 2 diabetes, or noninsulin-dependent diabetes mellitus (NIDDM), wherein patients produce insulin and even exhibit hyperinsulinemia (plasma insulin levels that are the same or even elevated in comparison with non-diabetic subjects), while at the same time demonstrating hyperglycemia. Type 1 diabetes is typically treated with exogenous insulin administered via injection. However, type 2 diabetics often develop "insulin resistance", such that the effect of insulin in stimulating glucose and lipid metabolism in the main insulin-sensitive tissues, namely, muscle, liver and adipose tissues, is diminished. Patients who are insulin resistant but not diabetic have elevated insulin levels that compensate for their insulin resistance, so that serum glucose levels are not elevated. In patients with NIDDM, the plasma insulin levels, even when they are elevated, are insufficient to overcome the pronounced insulin resistance, resulting in hyperglycemia.

Insulin resistance is primarily due to a receptor binding defect that is not yet completely understood. Resistance to insulin results in insufficient activation of glucose uptake, diminished oxidation of glucose and storage of glycogen in muscle, inadequate insulin repression of lipolysis in adipose tissue and inadequate glucose production and secretion by the liver.

The persistent or uncontrolled hyperglycemia that occurs in diabetics is associated with increased morbidity and premature mortality. Type 2 diabetics are at increased risk of developing cardiovascular complications, e.g., atherosclerosis, coronary heart disease, stroke, peripheral vascular disease, hypertension, nephropathy, neuropathy and retinopathy.

Non-insulin dependent diabetes is also associated with cardiac hypertrophy, in particular left ventricular hypertrophy (Devereux, R. B., Circulation, 101:2271–2276 (2000)). Cardiac hypertrophy, such as left ventricular hypertrophy, is due to the response of the heart to chronic pressure or volume overload. Left ventricular hypertrophy (LVH) is characterized by thickening of the left ventricular wall, including increased left ventricular mass and increased left ventricular wall thickness, and is defined as a left ventricular mass index exceeding 131 g/m$^2$ of the body surface area in men, and 100 g/m$^2$ in women (Savage et al., The Framingham Study, Circulation, 75 (1 Pt 2): 26–33 (1987).

Left ventricular hypertrophy is independently associated with increased incidence of cardiovascular disease, such as congestive heart failure, ischaemic heart disease, cardiovascular and all-cause mortality, sudden death, and stroke. Regression of left ventricular hypertrophy has been associated with a reduction in cardiovascular risk. It has also been found that the incidence of morbid events in patients with progression of left ventricular hypertrophy is greater than in patients with regression of left ventricular hypertrophy.

Current treatments for hypertrophy include non-pharmacological interventions, such as weight reduction, sodium restriction, and aerobic physical exercise can reduce left ventricular mass (Ghali, J. K. et al., American Journal of Geriatric Cardiology, 6:38–49 (1997).

Many patients who have insulin resistance but have not yet developed type 2 diabetes are also at a risk of developing metabolic syndrome, also referred to as syndrome X, insulin resistance syndrome, or plurimetabolic syndrome. The period of 5 to 10 years preceding the development of impaired glucose tolerance is associated with a number of hormonal imbalances, which give rise to an enlargement of visceral fat mass, hypertension, insulin resistance, and hyperlipidemia (Bjornstop, P., Current Topics in Diabetes Research, eds. Belfore, F., Bergman, R. N., and Molinath, G. M., Front Diabetes, Basel, Karger, 12:182–192 (1993)). Similarly, metabolic syndrome is characterized by insulin resistance, along with abdominal obesity, hyperinsulinemia, high blood pressure, low HDL and high VLDL. Although the causal relationship between the various components of metabolic syndrome remains to be confirmed, insulin resistance appears to play an important role (Requen, G. M., et al., N. Eng. J. Med. 334:374–381 (1996); Despres, J-P., et al., N. Engl. J. Med. 334:952–957(1996); Wajchenberg, B. L., et al., Diabetes/Metabolism Rev. 10:19–29 (1994)). Metabolic syndrome patients, whether or not they develop overt diabetes mellitus, are at increased risk of developing the cardiovascular complications listed above. Associations have also been found between left ventricular hypertrophy and metabolic syndrome (Marcus, R. et al. Circulation, 90:928–936 (1994); Lind, L. et al., J Hypertens. 13:433–38 (1995); Paolisso, G et al., Am J Hypertens., 10:1250–1256 (1997).

Diabetes is treated with a variety of therapeutic agents including insulin sensitizers, such as PPARγ agonists, such as glitazones; biguanides; protein tyrosine phosphatase-1B inhibitors; dipeptidyl peptidase IV inhibitors; insulin; insulin mimetics; sulfonylureas; meglitinides; α-glucoside hydrolase inhibitors; and α-amylase inhibitors.

Increasing the plasma level of insulin by administration of sulfonylureas (e.g. tolbutamide and glipizide) or meglitinides, which stimulate the pancreatic β-cells to secrete more insulin, and/or by injection of insulin when sulfonylureas or meglitinides become ineffective, can result in insulin concentrations high enough to stimulate insulin-resistant tissues. However, dangerously low levels of plasma glucose can result, and increasing insulin resistance due to the even higher plasma insulin levels can occur. The biguanides increase insulin sensitivity resulting in some correction of hyperglycemia. Metformin monotherapy is often used for treating type 2 diabetic patients who are also obese and/or dyslipidemic. Lack of appropriate response to metformin is often followed by treatment with sulfonylureas, thiazolidinediones, insulin, or alpha glucosidase inhibitors. However, the two biguanides, phenformin and metformin, can also induce lactic acidosis and nausea/diarrhea, respectively. Alpha glucosidase inhibitors, such as acarbose, work by delaying absorption of glucose in the intestine. Alpha-amylase inhibitors inhibit the enzymatic degradation of starch or glycogen into maltose, which also reduces the amounts of bioavailable sugars.

The glitazones, also known as thiazolidinediones (i.e. 5-benzylthiazolidine-2,4-diones), are a more recently described class of compounds with potential for a novel mode of action in ameliorating many symptoms of type 2diabetes. These agents substantially increase insulin sensitivity in muscle, liver and adipose tissue in several animal models of type 2 diabetes resulting in partial or complete correction of the elevated plasma levels of glucose without occurrence of hypoglycemia. The glitazones that are currently marketed are agonists of the peroxisome proliferator activated receptor (PPAR) gamma subtype. PPAR-gamma agonism is generally believed to be responsible for the improved insulin sensitization that is observed with the glitazones. Newer PPAR agonists that are being developed for treatment of Type 2 diabetes and/or dyslipidemia are agonists of one or more of the PPAR alpha, gamma and delta subtypes.

However, treatment of diabetes with PPARγ agonists has been associated with cardiac hypertrophy, or an increase in heart weight. Recent labeling revisions for Avandia (rosiglitazone maleate), a PPARγ agonist, indicate that patients may experience fluid accumulation and volume-related events such as edema and congestive heart failure. Cardiac hypertrophy related to PPARγ agonist treatment is typically treated by withdrawing PPAR treatment.

Treatment of type 2 diabetes also typically includes physical exercise, weight control and dieting. While physical exercise and reductions in dietary intake of calories will dramatically improve the diabetic condition, compliance with this treatment is very poor because of well-entrenched sedentary lifestyles and excess food consumption, especially of foods containing high amounts of saturated fat. However, weight reduction and increased exercise are difficult for most people with diabetes.

Abnormal glucose homeostasis is also associated both directly and indirectly with obesity, hypertension and alterations in lipid, lipoprotein and apolipoprotein metabolism. Obesity increases the likelihood of insulin resistance, and increases the likelihood that the resulting insulin resistance will increase with increasing body weight. Therefore, therapeutic control of glucose homeostasis, lipid metabolism, obesity and hypertension are critically important in the clinical management and treatment of diabetes mellitus.

Obesity, which can be defined as a body weight more than 20% above the ideal body weight, is a major health concern in Western societies. It is estimated that about 97 million adults in the United States are overweight or obese. Obesity is the result of a positive energy balance, as a consequence of increased ratio of caloric intake to energy expenditure. The molecular factors regulating food intake and body weight balance are incompletely understood. [B. Staels et al., J. Biol. Chem. 270(27), 15958(1995); F. Lonnquist et al., Nature Medicine 1(9), 950 (1995)]. Although the genetic and/or environmental factors leading to obesity are poorly understood, several genetic factors have been identified.

Epidemiological studies have shown that increasing degrees of overweight and obesity are important predictors of decreased life expectancy. Obesity causes or exacerbates many health problems, both independently and in association with other diseases. The medical problems associated with obesity, which can be serious and life-threatening, include type 2 diabetes mellitus, hypertension, elevated plasma insulin concentrations, insulin resistance, dyslipidemias, hyperlipidemia, endometrial, breast, prostate, kidney and colon cancer, osteoarthritis; respiratory complications, such as obstructive sleep apnea, gallstones, arteriosclerosis, heart disease, abnormal heart rhythms, and heart arrythmias (Kopelman, P. G., Nature 404, 635–643 (2000)). Obesity is also associated with metabolic syndrome, cardiac hypertrophy, in particular left ventricular hypertrophy, premature death, and with a significant increase in mortality and morbidity from stroke, myocardial infarction, congestive heart failure, coronary heart disease, and sudden death.

Abdominal obesity has been linked with a much higher risk of coronary artery disease, and with three of its major risk factors: high blood pressure, diabetes that starts in adulthood, and high levels of fats (lipids) in the blood. Losing weight dramatically reduces these risks. Abdominal obesity is further closely associated with glucose intolerance, hyperinsulinemia, hypertriglyceridemia, and other disorders associated with metabolic syndrome (syndrome X), such as raised high blood pressure, decreased levels of high density lipoproteins (HDL) and increased levels of very low density lipoproteins (VLDL) (Montague et al., Diabetes, 2000, 49: 883–888).

Obesity and obesity-related disorders, such as diabetes, are often treated by encouraging patients to lose weight by reducing their food intake or by increasing their exercise level, thereby increasing their energy output. A sustained weight loss of 5% to 10% of body weight has been shown to improve the comorbidities associated with obesity, such as diabetes, and can lead to improvement of obesity-related disorders such as diabetes, left ventricular hypertrophy, osteoarthritis, and pulmonary and cardiac dysfunction.

Weight loss drugs used for the treatment of obesity include orlistat (Davidson, M. H. et al. (1999) JAMA 281:235–42), dexfenfluramine (Guy Grand, B. et al. (1989) Lancet 2:1142–5), sibutramine (Bray, G. A. et al. (1999) Obes. Res. &:189–98) and phentermine (Douglas, A. et al. (1983) Int. J. Obes. 7:591–5). However, the side effects of these drugs and anti-obesity agents may limit their use. Dexfenfluramine was withdrawn from the market because of suspected heart valvulopathy; orlistat is limited by gastrointestinal side effects; and the use of sibutramine is limited by its cardiovascular side effects which have led to reports of deaths and its withdrawal from the market in Italy.

The term "diabetes," as used herein, includes both insulin-dependent diabetes mellitus (i.e., IDDM, also known as type 1 diabetes) and non-insulin-dependent diabetes mellitus (i.e., NIDDM, also known as Type 2 diabetes). The compositions of the present invention are useful for treating both Type 1 and Type 2 diabetes. The compositions are especially effective for treating Type 2 diabetes. The compositions of the present invention are also useful for treating and/or preventing gestational diabetes mellitus.

Treatment of diabetes mellitus refers to the administration of a compound or combination of the present invention to treat diabetes. One outcome of treatment may be decreasing the glucose level in a subject with elevated glucose levels. Another outcome of treatment may be decreasing insulin levels in a subject with elevated insulin levels. Another outcome of treatment is decreasing plasma triglycerides in a subject with elevated plasma triglycerides. Another outcome of treatment is decreasing LDL cholesterol in a subject with high LDL cholesterol levels. Another outcome of treatment is increasing HDL cholesterol in a subject with low HDL cholesterol levels. Another outcome of treatment is increasing insulin sensitivity. Another outcome of treatment may be enhancing glucose tolerance in a subject with glucose intolerance. Yet another outcome of treatment may be decreasing insulin resistance in a subject with increased insulin resistance or elevated levels of insulin.

Prevention of diabetes mellitus refers to the administration of a compound or combination of the present invention to prevent the onset of diabetes in a subject in need thereof.

The term "hypertension" as used herein includes essential, or primary, hypertension wherein the cause is not known or where hypertension is due to greater than one cause, such as changes in both the heart and blood vessels; and secondary hypertension wherein the cause is known. Causes of secondary hypertension include, but are not limited to obesity; kidney disease; hormonal disorders; use of certain drugs, such as oral contraceptives, corticosteroids, cyclosporin, and the like. The term "hypertension" encompasses high blood pressure, in which both the systolic and diastolic pressure levels are elevated, and isolated systolic hypertension, in which only the systolic pressure is elevated to greater than or equal to 140 mm Hg, while the diastolic pressure is less than 90 mm Hg. One outcome of treatment is decreasing blood pressure in a subject with high blood pressure.

Dyslipidemias or disorders of lipid metabolism, include various conditions characterized by abnormal concentrations of one or more lipids (i.e. cholesterol and triglycerides), and/or apolipoproteins (i.e., apolipoproteins A, B, C and E), and/or lipoproteins (i.e., the macromolecular complexes formed by the lipid and the apolipoprotein that allow lipids to circulate in blood, such as LDL, VLDL and IDL). Hyperlipidemia is associated with abnormally high levels of lipids, LDL and VLDL cholesterol, and/or triglycerides.

The term "metabolic syndrome", also known as syndrome X, is defined in the Third Report of the National Cholesterol Education Program Expert Panel on Detection, Evaluation and Treatment of High Blood Cholesterol in Adults (ATP-III). E. S. Ford et al., JAMA, vol. 287 (3), Jan. 16, 2002, pp 356–359. Briefly, a person is defined as having metabolic syndrome if the person has three or more of the following symptoms: abdominal obesity, hypertriglyceridemia, low HDL cholesterol, high blood pressure, and high fasting plasma glucose. The criteria for these are defined in ATP-III.

The term "left venticular hypertrophy" (LVH) as used herein includes three patterns of left ventricular hypertrophy that have been identified based on left ventricular mass index (LVMI=left ventricular mass in grams divided by body surface area in meters2) and relative wall thickness (RWT=2×posterior wall thickness/left ventricular end diastolic diameter). Concentric LVH is typically exemplified by a left ventricular mass index of 144 and a relative wall thickness of 0.52; eccentric LVH is typically exemplified by a left ventricular mass index of 136 and a relative wall thickness of 0.38; and concentric left ventricular remodeling which is typically exemplified by a LVMI of 93 and a relative wall thickness of 0.49. Normal LVMI are typically 85 and normal RWT approximately 0.36. Patients with concentric left ventricular (LV) remodeling have a cardiovascular risk intermediate between those with normal left ventricular structure and those with left ventricular hypertrophy.

One outcome of treatment of diabetes while minimizing cardiac hypertrophy, or left ventricular hypertrophy, may be a decrease in ventricular mass. Another outcome of treatment of diabetes while minimizing cardiac hypertrophy or left ventricular hypertrophy may be a decrease in the rate of increase of ventricular mass. Another outcome of treatment of diabetes while minimizing cardiac hypertrophy or left ventricular hypertrophy may be a decrease in ventricular wall thickness. Another outcome of treatment of diabetes while minimizing cardiac hypertrophy of left ventricular hypertrophy may be the decrease in the rate of increase in ventricular wall thickness.

The term "obesity" as used herein is a condition in which there is an excess of body fat. The operational definition of obesity is based on the Body Mass Index (BMI), which is calculated as body weight per height in meters squared ($kg/m^2$). "Obesity" refers to a condition whereby an otherwise healthy subject has a Body Mass Index (BMI) greater than or equal to 30 $kg/m^2$, or a condition whereby a subject with at least one co-morbidity has a BMI greater than or equal to 27 kg/m². An "obese subject" is an otherwise healthy subject with a Body Mass Index (BMI) greater than or equal to 30 kg/m² or a subject with at least one co-morbidity with a BMI greater than or equal to 27 kg/m². A "subject at risk of obesity" is an otherwise healthy subject with a BMI of 25 kg/m² to less than 30 kg/m² or a subject with at least one co-morbidity with a BMI of 25 kg/m² to less than 27 kg/m².

The increased risks associated with obesity occur at a lower Body Mass Index (BMI) in Asians. In Asian countries, including Japan, "obesity" refers to a condition whereby a subject with at least one obesity-induced or obesity-related co-morbidity, that requires weight reduction or that would be improved by weight reduction, has a BMI greater than or equal to 25 kg/m². In Asian countries, including Japan, an "obese subject" refers to a subject with at least one obesity-induced or obesity-related co-morbidity that requires weight reduction or that would be improved by weight reduction, with a BMI greater than or equal to 25 kg/m². In Asia-Pacific, a "subject at risk of obesity" is a subject with a BMI of greater than 23 kg/m² to less than 25 kg/m².

As used herein, the term "obesity" is meant to encompass all of the above definitions of obesity.

Obesity-induced or obesity-related co-morbidities include, but are not limited to, diabetes, non-insulin dependent diabetes mellitus—type 2, diabetes associated with obesity, impaired glucose tolerance, impaired fasting glucose, insulin resistance syndrome, dyslipidemia, hypertension, hypertension associated with obesity, hyperuricacidemia, gout, coronary artery disease, myocardial infarction, angina pectoris, sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, diabetes mellitus, and other obesity-related conditions.

Treatment of obesity and obesity-related disorders refers to the administration of the compounds or combinations of the present invention to reduce or maintain the body weight of an obese subject. One outcome of treatment may be reducing the body weight of an obese subject relative to that subject's body weight immediately before the administration of the compounds or combinations of the present invention. Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate; and in weight reduction in patients in need thereof. The treatment may also result in an alteration of metabolic rate, such as an increase in metabolic rate, rather than or in addition to an inhibition of the reduction of metabolic rate; and/or in minimization of the metabolic resistance that normally results from weight loss.

Prevention of obesity and obesity-related disorders refers to the administration of the compounds or combinations of the present invention to reduce or maintain the body weight of a subject at risk of obesity. One outcome of prevention may be reducing the body weight of a subject at risk of obesity relative to that subject's body weight immediately before the administration of the compounds or combinations of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type 2 diabetes, polycystic ovary disease, cardiovascular diseases, osteoarthritis, dermatological disorders, hypertension, insulin resistance, hypercholesterolemia, hypertriglyceridemia, and cholelithiasis.

The term "atherosclerosis" as used herein encompasses vascular diseases and conditions that are recognized and understood by physicians practicing in the relevant fields of medicine. Atherosclerotic cardiovascular disease, coronary heart disease (also known as coronary artery disease or ischemic heart disease), cerebrovascular disease and peripheral vessel disease are all clinical manifestations of atherosclerosis and are therefore encompassed by the terms "atherosclerosis" and "atherosclerotic disease." The combination comprised of a therapeutically effective amount of an anti-obesity agent in combination with a therapeutically effective amount of an anti-diabetic agent may be administered to prevent or reduce the risk of occurrence, or recurrence where the potential exists, of a coronary heart disease event, a cerebrovascular event, or intermittent claudication. Coronary heart disease events are intended to include CHD death, myocardial infarction (i.e., a heart attack), and coronary revascularization procedures. Cerebrovascular events are intended to include ischemic or hemorrhagic stroke (also known as cerebrovascular accidents) and transient ischemic attacks. Intermittent claudication is a clinical manifestation of peripheral vessel disease. The term "atherosclerotic disease event" as used herein is intended to encompass coronary heart disease events, cerebrovascular events, and intermittent claudication. It is intended that persons who have previously experienced one or more non-fatal atherosclerotic disease events are those for whom the potential for recurrence of such an event exists.

Circadian rhythms affect a variety of physiological parameters: rest-activity, sleep-wake cycles, body temperature, rhythms in hormone levels, oscillations in general physiology and the like. When these parameters are out of synchrony with the daily clock, a circadian rhythm imbalance occurs which can affect physiology, performance on a variety of tasks and one's emotional well being. The present invention is useful, for example, in the prevention or treatment of conditions associated with circadian rhythmicity as well as mental and physical disorders associated with travel across time zones and with rotating shift-work schedules.

In another embodiment, the present invention provides a method for the prevention or treatment of a circadian rhythm disorder in a mammal, including time-zone change (jet-lag) syndrome, shift-work sleep disorder, delayed sleep-phase syndrome, advanced sleep-phase syndrome, and non-24-hour sleep-wake disorder, which comprises administering to the mammal an effective amount of a compound of the present invention.

In another embodiment, the present invention provides a method for shortening the time of re-entrainment (return to normal entrainment of the circadian rhythms; synchronized to the environmental light-dark cycle) in a subject following a shift in the sleep-wake cycle which comprises administering to the subject an appropriate amount of a compound of the present invention.

In another embodiment, the present invention provides a method for alleviating the effects of jet lag in a traveler, especially a mammal, which comprises administering to the traveler an alertness increasing amount of a compound of the present invention. The purpose of this embodiment is to assist the body to adjust physiologically to the changes in sleep and feeding patterns when crossing several time zones.

In another more preferred embodiment, the present invention provides a method for resetting the internal circadian clock in a subject to match the subject's current activity/sleep cycle. For example shift workers changing from a day to a night shift or vice versa, which comprises administering to the subject an appropriate amount of a compound of the present invention.

The present invention is further directed to the use of a compound of the present invention, for enhancing or improving sleep quality as well as preventing and treating sleep disorders and sleep disturbances in a mammal. In particular, the present invention provides a method for enhancing or improving sleep quality by increasing sleep efficiency and augmenting sleep maintenance. In addition, the present invention provides a method for preventing and treating sleep disorders and sleep disturbances in a mammal which comprising the administration of a compound of the present invention. The present invention further provides a pharmaceutical composition for enhancing or improving sleep quality and increasing sleep efficiency and sleep maintenance. The present invention is useful for the treatment of sleep disorders, including Disorders of Initiating and Maintaining Sleep (insomnias) ("DIMS") which can arise from psychophysiological causes, as a consequence of psychiatric disorders (particularly related to anxiety), from drugs and alcohol use and abuse (particularly during withdrawal stages), childhood onset DIMS, nocturnal myoclonus and restless legs and non specific REM disturbances as seen in ageing.

The following outcomes in a subject which are provided by the present invention may be correlated to enhancement in sleep quality: an increase in the value which is calculated from the time that a subject sleeps divided by the time that a subject is attempting to sleep; a decrease in sleep latency (the time it takes to fall asleep); a decrease in the number of awakenings during sleep; a decrease in the time spent awake following the initial onset of sleep; an increase in the total amount of sleep; an increase the amount and percentage of REM sleep; an increase in the duration and occurrence of REM sleep; a reduction in the fragmentation of REM sleep; an increase in the amount and percentage of slow-wave (i.e. stage 3 or 4) sleep; an increase in the amount and percentage of stage 2 sleep; a decrease in the number of awakenings, especially in the early morning; an increase in daytime alertness; and increased sleep maintenance. Secondary outcomes which may be provided by the present invention include enhanced cognitive function and increased memory retention. A "method for enhancing the quality of sleep" refers to a method that results in outcomes in a subject which may be correlated to enhancement in sleep quality, including, but not limited to, the outcomes correlated to enhancement of sleep quality as defined above.

The present invention is further useful for the prevention and treatment of sleep disorders and sleep disturbances including sleep problems associated with insomnia, hypersomnia, sleep apnea, narcolepsy, nocturnal myoclonus, REM sleep interruptions, jet-lag, shift workers' sleep disturbances, dysomnias, night terror, night eating syndrome, insomnias associated with depression or with emotional/mood disorders, dysfunctions associated with sleep (parasomnias), as well as sleep walking and enuresis, as well as sleep disorders which accompany aging. Sleep disorders and sleep disturbances are generally characterized by difficulty in initiating or maintaining sleep or in obtaining restful or enough sleep.

In addition, certain drugs may also cause reductions in REM sleep as a side effect and the present invention may be used to correct those types of sleeping disorders as well. The present invention would also be of benefit in the treatment of syndromes such as fibromyalgia which are manifested by non-restorative sleep and muscle pain or sleep apnea which is associated with respiratory disturbances during sleep. It will be clear to one skilled in the art that the present invention is not limited to just sleep disorders and sleep disturbances, but is applicable to a wide variety of conditions which result from a diminished quality of sleep.

The present invention is also concerned with treatment and prevention of these conditions, and with the use of a compound of the present invention, combinations, and compositions thereof, for the manufacture of a medicament useful for treating or preventing these conditions.

In the present invention, it is preferred that the subject mammal is a human. Although the present invention is applicable both old and young people, it may find greater application in elderly people. Further, although the invention may be employed to enhance the sleep of healthy people, it may be especially beneficial for enhancing the sleep quality of people suffering from sleep disorders or sleep disturbances.

The compositions of the present invention may be used in combination with other drugs that may also be useful in the treatment, prevention, or control of disorders, such as hypertension, hypertension associated with obesity, hypertension-related disorders, cardiac hypertrophy, left ventricular hypertrophy, and metabolic syndrome, obesity and obesity-related disorders, for which compounds comprising the compositions are useful. Such other drugs may be administered, by a route and in an amount commonly used therefore, contemporaneously or sequentially with a composition of the present invention. When a composition of the present invention is used contemporaneously with one or more other drugs, a pharmaceutical composition in unit dosage form containing such other drugs and the composition of the present invention is preferred. However, the combination therapy also includes therapies in which the composition of the present invention and one or more other drugs are administered on different overlapping schedules. It is also contemplated that when used in combination with one or more other active ingredients, the composition of the present invention and the other active ingredients may be used in lower doses than when each is used singly. Accordingly, the pharmaceutical compositions of the present invention include those that contain one or more other active ingredients, in addition to a composition of the present invention.

Examples of other active ingredients that may be administered in combination with a composition of the present invention, and either administered separately or in the same pharmaceutical composition, include, but are not limited to:

(a) anti-diabetic agents such as (i) PPARγ agonists such as glitazones (e.g. ciglitazone; darglitazone; englitazone;

isaglitazone (MCC-555); pioglitazone; rosiglitazone; troglitazone; BRL49653; CLX-0921; 5-BTZD, and the like), and GW-0207, LG-100641, and LY-300512, and the like; (ii) biguanides such as buformin; metformin; and phenformin, and the like; (iii) protein tyrosine phosphatase-1B (PTP-1B) inhibitors; (iv) sulfonylureas such as acetohexamide; chlorpropamide; diabinese; glibenclamide; glipizide; glyburide; glimepiride; gliclazide; glipentide; gliquidone; glisolamide; tolazamide; and tolbutamide, and the like; (v) meglitinides such as repaglinide, and nateglinide, and the like; (vi) alpha glucoside hydrolase inhibitors such as acarbose; adiposine; camiglibose; emiglitate; miglitol; voglibose; pradimicin-Q; salbostatin; CKD-711; MDL-25,637; MDL-73,945; and MOR14, and the like; (vii) alphaamylase inhibitors such as tendamistat, trestatin, and A1–3688, and the like; (viii) insulin secreatagogues such as linogliride; and A-4166, and the like; (ix) fatty acid oxidation inhibitors, such as clomoxir, and etomoxir, and the like; (x) A2 antagonists, such as midaglizole; isaglidole; deriglidole; idazoxan; earoxan; and fluparoxan, and the like; (xi) insulin or insulin mimetics, such as biota, LP-100, novarapid, insulin detemir, insulin lispro, insulin glargine, insulin zinc suspension (lente and ultralente); Lys-Pro insulin, GLP-1 (73–7) (insulintropin); and GLP-1 (7–36)—NH$_2$), and the like; (xii) non-thiazolidinediones such as JT-501, and farglitazar (GW-2570/GI-262579), and the like; (xiii) PPARα/γ dual agonists such as MK-0767, CLX-0940, GW-1536, GW1929, GW-2433, KRP-297, L-796449, LR-90, and SB 219994, and the like; (xiv) other insulin sensitizing drugs; and (xv) VPAC2 receptor agonists;

(b) lipid lowering agents such as (i) bile acid sequestrants such as, cholestyramine, colesevelem, colestipol, dialkylaminoalkyl derivatives of a cross-linked dextran; Colestid®; LoCholest®; and Questran®, and the like; (ii) HMG-CoA reductase inhibitors such as atorvastatin, itavastatin, fluvastatin, lovastatin, pravastatin, rivastatin, rosuvastatin, simvastatin, and ZD-4522, and the like; (iii) HMG-CoA synthase inhibitors; (iv) cholesterol absorption inhibitors such as stanol esters, beta-sitosterol, sterol glycosides such as tiqueside; and azetidinones such as ezetimibe, and the like; (v) acyl coenzyme A-cholesterol acyl transferase (ACAT) inhibitors such as avasimibe, eflucimibe, KY505, SMP 797, and the like; (vi) CETP inhibitors such as JTT 705, torcetrapib, CP 532,632, BAY63–2149, SC 591, SC 795, and the like; (vii) squalene synthetase inhibitors; (viii) anti-oxidants such as probucol, and the like; (ix) PPARα agonists such as beclofibrate, benzafibrate, ciprofibrate, clofibrate, etofibrate, fenofibrate, gemcabene, and gemfibrozil, GW 7647, BM 170744, LY518674; and other fibric acid derivatives, such as Atromid®, Lopid® and Tricor®, and the like; (x) FXR receptor modulators such as GW 4064, SR 103912, and the like; (xi) LXR receptor such as GW 3965, T9013137, and XTCO179628, and the like; (xii) lipoprotein synthesis inhibitors such as niacin; (xiii) renin angiotensin system inhibitors; (xiv) PPARδ partial agonists; (xv) bile acid reabsorption inhibitors, such as BARI 1453, SC435, PHA384640, S8921, AZD7706, and the like; (xvi) PPARδ agonists such as GW501516, and GW590735, and the like; (xvii) triglyceride synthesis inhibitors; (xviii) microsomal triglyceride transport (MTTP) inhibitors, such as inplitapide, LAB687, and CP346086, and the like; (xix) transcription modulators; (xx) squalene epoxidase inhibitors; (xxi) low density lipoprotein (LDL) receptor inducers; (xxii) platelet aggregation inhibitors; (xxiii) 5-LO or FLAP inhibitors; and (xiv) niacin receptor agonists; and (c) anti-hypertensive agents such as (i) diuretics, such as thiazides, including chlorthalidone, chlorthiazide, dichlorophenamide, hydroflumethiazide, indapamide, and hydrochlorothiazide; loop diuretics, such as bumetanide, ethacrynic acid, furosemide, and torsemide; potassium sparing agents, such as amiloride, and triamterene; and aldosterone antagonists, such as spironolactone, epirenone, and the like; (ii) betaadrenergic blockers such as acebutolol, atenolol, betaxolol, bevantolol, bisoprolol, bopindolol, carteolol, carvedilol, celiprolol, esmolol, indenolol, metaprolol, nadolol, nebivolol, penbutolol, pindolol, propanolol, sotalol, tertatolol, tilisolol, and timolol, and the like; (iii) calcium channel blockers such as amlodipine, aranidipine, azelnidipine, barnidipine, benidipine, bepridil, cinaldipine, clevidipine, diltiazem, efonidipine, felodipine, gallopamil, isradipine, lacidipine, lemildipine, lercanidipine, nicardipine, nifedipine, nilvadipine, nimodepine, nisoldipine, nitrendipine, manidipine, pranidipine, and verapamil, and the like; (iv) angiotensin converting enzyme (ACE) inhibitors such as benazepril; captopril; cilazapril; delapril; enalapril; fosinopril; imidapril; losinopril; moexipril; quinapril; quinaprilat; ramipril; perindopril; perindropril; quanipril; spirapril; tenocapril; trandolapril, and zofenopril, and the like; (v) neutral endopeptidase inhibitors such as omapatrilat, cadoxatril and ecadotril, fosidotril, sampatrilat, AVE7688, ER4030, and the like; (vi) endothelin antagonists such as tezosentan, A308165, and YM62899, and the like; (vii) vasodilators such as hydralazine, clonidine, minoxidil, and nicotinyl alcohol, and the like; (viii) angiotensin II receptor antagonists such as candesartan, eprosartan, irbesartan, losartan, pratosartan, tasosartan, telmisartan, valsartan, and EXP-3137, FI6828K, and RNH6270, and the like; (viv) α/β adrenergic blockers as nipradilol, arotinolol and amosulalol, and the like; (x) alpha 1 blockers, such as terazosin, urapidil, prazosin, bunazosin, trimazosin, doxazosin, naftopidil, indoramin, WHIP 164, and XEN010, and the like; (xi) alpha 2 agonists such as lofexidine, tiamenidine, moxonidine, rilmenidine and guanobenz, and the like; and (xii) aldosterone inhibitors, and the like; and (d) anti-obesity agents, such as (i) 5HT (serotonin) transporter inhibitors, such as paroxetine, fluoxetine, fenfluramine, fluvoxamine, sertraline, and imipramine; (ii) NE (norepinephrine) transporter inhibitors, such as GW 320659, despiramine, talsupram, and nomifensine; (iii) CB-1 (cannabinoind-1 receptor) antagonist/inverse agonists, such as rimonabant (Sanofi Synthelabo), SR-147778 (Sanofi Synthelabo), BAY 65–2520 (Bayer), and SLV 319 (Solvay), and those disclosed in U.S. Pat. Nos. 5,532,237, 4,973,587, 5,013,837, 5,081, 122, 5,112,820, 5,292,736, 5,624,941 and U.S. Pat. No. 6,028,084; and WO 96/33159, WO 98/33765, WO98/43636, WO98/43635, WO 01/09120, WO 01.96330, WO98/31227, WO98/41519, WO98/37061, WO00/10967, WO00/10968, WO97/29079, WO99/02499, WO 01/58869, WO 02/076949, WO 01/64632, WO 01/64633, WO 01/64634, WO 03/006007, and WO 03/007887; and EPO Application No. EP-658546; (iv) ghrelin antagonists, such as those disclosed in WO 01/87335, and WO 02/08250; (v) H3 (histamine H3) antagonist/inverse agonists, such as thioperamide, 3-(1H-imidazol-4-yl)propyl N-(4-pentenyl)carbamate, clobenpropit, iodophenpropit, imoproxifan, GT2394 (Gliatech), and A331440, and those disclosed in WO 02/15905; and O-[3-(1H-imidazol-4-yl)propanol] carbamates (Kiec-Kononowicz, K. et al., Pharmazie, 55:349–55 (2000)), piperidine-containing histamine H3-receptor antagonists (Lazewska, D. et al., Pharmazie, 56:927–32 (2001), benzophenone derivatives and related compounds (Sasse, A. et al., Arch. Pharm. (Weinheim) 334:45–52 (2001)), substituted N-phenylcarbamates (Reidemeister, S. et al., Pharmazie, 55:83–6 (2000)), and proxifan derivatives (Sasse, A. et al., J. Med. Chem. 43:3335–43 (2000)); (vi) melanin-concentrating hormone 1 receptor (MCH1R) antagonists, such as T-226296 (Takeda), SNP-7941 (Synaptic), and those disclosed in WO 01/82925, WO 01/87834, WO 02/051809, WO 02/06245, WO 02/076929, WO 02/076947, WO 02/04433, WO 02/51809, WO 02/083134, WO 02/094799, WO 03/004027, and Japanese Patent Application No. JP 13226269; (vii) MCH2R (melanin concentrating hormone 2R) agonist/antagonists; (viii) NPY1 (neuropeptide Y Y1) antagonists, such as BIBP3226, 2-[1-(5-chloro-3-isopropyloxycarbonylaminophenyl)ethylamino]-6-[2-(5-ethyl-4-methyl-1,3-thiazol-2-yl)ethyl]-4-morpholi nopyridine, BIBO 3304, LY-357897, CP-671906, and GI-264879A; and those disclosed in U.S. Pat. No. 6,001,836; and WO 96/14307, WO 01/23387, WO 99/51600, WO 01/85690, WO 01/85098, WO 01/85173, and WO 01/89528; (ix) NPY5 (neuropeptide Y Y5) antagonists, such as L-152,804, GW-569180A, GW-594884A, GW-587081X, GW-548118X; FR235, 208; FR226928, FR240662, FR252384; 1229U91, GI-264879A, CGP71683A, LY-377897, LY366377, PD-160170, SR-120562A, SR-120819A, JCF-104, and H409/22; and those compounds disclosed in U.S. Pat. Nos. 6,140,354, 6,191,160, 6,258,837, 6,313,298, 6,337,332, 6,329,395, and 6,340,683; U.S. Pat. Nos. 6,326,375; 6,329,395; 6,337,332; 6,335,345; European Patent Nos. EP-01010691, and EP-01044970; and PCT International Patent Publication Nos. WO 97/19682, WO 97/20820, WO 97/20821, WO 97/20822, WO 97/20823, WO 98/27063, WO 00/107409, WO 00/185714, WO 00/185730, WO 00/64880, WO 00/68197, WO 00/69849, WO 01/09120, WO 01/14376, WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/20488, WO 02/22592, WO 02/48152, WO 02/49648 and WO 02/094789; and Norman et al., J. Med. Chem. 43:4288–4312 (2000); (x) leptin, such as recombinant human leptin (PEG-OB, Hoffman LaRoche) and recombinant methionyl human leptin (Amgen); (xi) leptin derivatives, such as those disclosed in U.S. Pat. Nos. 5,552,524; 5,552,523; 5,552, 522; 5,521,283; and PCT International Publication Nos. WO 96/23513; WO 96/23514; WO 96/23515; WO 96/23516; WO 96/23517; WO 96/23518; WO 96/23519; and WO 96/23520; (xii) opioid antagonists, such as nalmefene (Revex®), 3-methoxynaltrexone, naloxone, and naltrexone; and those disclosed in WO 00/21509; (xiii) orexin antagonists, such as SB-334867-A; and those disclosed in WO 01/96302, WO 01/68609, WO 02/51232, WO 02/51838, and WO 03/023561; (xiv) BRS3 (bombesin receptor subtype 3) agonists; (xv) CCK-A (cholecystokinin-A) agonists, such as AR-R 15849, GI 181771, JMV-180, A-71378, A-71623 and SR146131, and those disclosed in U.S. Pat. No. 5,739,106; (xvi) CNTF (ciliary neurotrophic factors), such as GI-181771 (Glaxo-SmithKline); SR146131 (Sanofi Synthelabo); butabindide; and PD170,292, PD 149164 (Pfizer); (xvii) CNTF derivatives, such as axokine (Regeneron); and WO 94/09134, WO 98/22128, and WO 99/43813; (xviii) GHS (growth hormone secretagogue receptor) agonists, such as NN703, hexarelin, MK-0677, SM-130686, CP-424,391, L-692,429 and L-163,255, and those disclosed in U.S. Pat. No. 6,358,951, U.S. patent application Nos. 2002/049196 and 2002/022637; and WO 01/56592, and WO 02/32888; (xix) 5HT2c (serotonin receptor 2c) agonists, such as BVT933, DPCA37215, IK264; PNU 22394; WAY161503, R-1065, and YM 348; and those disclosed in U.S. Pat. No. 3,914,250; and WO 02/36596, WO 02/48124, WO 02/10169, WO 01/66548, WO 02/44152; WO 02/51844, WO 02/40456, and WO 02/40457; (xx) Mc3r (melanocortin 3 receptor) agonists; (xxi) Mc4r (melanocortin 4 receptor) agonists, such as CHIR86036 (Chiron); ME-10142, and ME-10145 (Melacure), and those disclosed in WO 99/64002, WO 00/74679, WO 01/991752, WO 01/74844, WO 01/70708, WO 01/70337, WO 01/91752, WO 02/059095, WO 02/059107, WO 02/059108, WO 02/059117, WO 02/12166, WO 02/11715, WO 02/12178, WO 02/15909, WO 02/068387, WO 02/068388, WO 02/067869, WO 03/007949, and WO 03/009847; (xxii) monoamine reuptake inhibitors, such as sibutratmine (Meridia®/Reductil®) and a salt thereof, and those compounds disclosed in U.S. Pat. Nos. 4,746,680, 4,806,570, and 5,436,272, and U.S. Patent Publication No. 2002/0006964, and WO 01/27068, and WO 01/62341; (xxiii) serotonin reuptake inhibitors, such as dexfenfluramine, fluoxetine, and those in U.S. Pat. No. 6,365,633, and WO 01/27060, and WO 01/162341; (xxiv) GLP-1 (glucagon-like peptide 1) agonists; (xxv) Topiramate (Topimax®); (xxvi) phytopharm compound 57 (CP 644,673); (xxvii) ACC2(acetyl-CoA carboxylase-2) inhibitors; (xxviii) β3 (beta adrenergic receptor 3) agonists, such as AD9677/TAK677 (Dainippon/Takeda), CL-316,243, SB 418790, BRL-37344, L-796568, BMS-196085, BRL-35135A, CGP12177A, BTA-243, GW 427353, Trecadrine, Zeneca D7114, and SR 59119A, and those disclosed in U.S. patent application No. 5,705,515, U.S. Pat. No. 5,451,677; and WO 01/74782, and WO 02/32897; (xxix) DGAT1 (diacylglycerol acyltransferase 1) inhibitors; (xxx) DGAT2 (diacylglycerol acyltransferase 2)inhibitors; (xxxi) FAS (fatty acid synthase) inhibitors, such as Cerulenin and C75; (xxxii) PDE (phosphodiesterase) inhibitors, such as theophylline, pentoxifylline, zaprinast, sildenafil, amrinone, milrinone, cilostamide, rolipram, and cilomilast; (xxxii) thyroid hormone β agonists, such as KB-2611 (KaroBioBMS), and those disclosed in WO 02/15845; and Japanese Patent Application No. JP 2000256190; (xxxiii) UCP-1 (uncoupling protein 1), 2, or 3 activators, such as phytanic acid, 4-[(E)-2-(5,6,7,8-tetrahydro-5,5,8,8-tetramethyl-2-napthalenyl)-1-propenyl]benzoic acid (TTNPB), and retinoic acid; and those disclosed in WO 99/00123;

(xxxiv) acyl-estrogens, such as oleoyl-estrone, disclosed in del Mar-Grasa, M. et al., Obesity Research, 9:202–9 (2001); (xxxv) glucocorticoid antagonists; (xxxvi) 11β HSD-1 (11-beta hydroxy steroid dehydrogenase type 1) inhibitors, such as BVT 3498, BVT 2733, and those compounds disclosed in WO 01/90091, WO 01/90090, WO 01/90092; (xxxvii) SCD-1 (stearoyl-CoA desaturase-1) inhibitors; (xxxviii) dipeptidyl peptidase IV (DP-IV) inhibitors, such as isoleucine thiazolidide, valine pyrrolidide, NVP-DPP728, LAF237, P93/01, TSL 225, TMC-2A/2B/2C, FE 999011, P9310/K364, VIP 0177, SDZ 274–444; and the compounds disclosed in WO 03/004498, WO 03/004496, EP 1258476, WO 02/083128, WO 02/062764, WO 03/000250, WO 03/002530, WO 03/002531, WO 03/002553, WO 03/002593, WO 03/000180, and WO 03/000181; (xxxviii) lipase inhibitors, such as tetrahydrolipstatin (orlistat/Xenical®), Triton WR1339, RHC80267, lipstatin, teasaponin, and diethylumbelliferyl phosphate, FL-386, WAY-121898, Bay-N-3176, valilactone, esteracin, ebelactone A, ebelactone B, and RHC 80267, and those disclosed in WO 01/77094, and U.S. Pat. Nos. 4,598,089, 4,452,813, 5,512,565, 5,391,571, 5,602,151, 4,405,644, 4,189,438, and 4,242,453; (xxxix) fatty acid transporter inhibitors; (xxxx) dicarboxylate transporter inhibitors; (xxxxi) glucose transporter inhibitors; (xxxxii) phosphate transporter inhibitors; (xxxxiii) melanocortin agonists, such as Melanotan II or those described in WO99/64002 and WO00/746799; (xxxxiv) melanin concentrating hormone antagonists; (xxxxv) galanin antagonists; (xxxxvi) CCK agonists; (xxxxvii) corticotropin-releasing hormone agonists; and (xxxxviii) phosphodiesterase-3B (PDE3B) inhibitors; and the like.

The above combinations include combinations of a composition of the present invention not only with one other active compound, but also with two or more other active compounds. Non-limiting examples include combinations of the compositions of the present invention with one, two or more active compounds selected from lipid-lowering agents, and anti-hypertensive agents. Combinations of the compositions of the present invention with one, two or more active compounds selected from lipid lowering agents, and anti-diabetic agents are useful to treat, control or prevent metabolic syndrome. In particular, compositions comprising an anti-obesity agent, an anti-hypertensive agent, in addition to an anti-diabetic agent and/or a lipid lowering agent will be useful to synergistically treat, control or prevent metabolic syndrome.

The present invention is further described in detail with reference to the following Examples and Reference Examples, but the invention should in no way be restricted thereby.

The compounds with the symbol * in the chemical formulae indicate that the stereo configuration on the asymmetric carbon atom with the symbol * is substantially of a single compound.

EXAMPLES

Example 1

Preparation of 5-[(4S,5S)-4-(4-fluorophenyl)-4-(6-fluoro-3-pyridyl)-5-methyl-2-imidazolin-2-yl]-1-methyl-2-pyridone
(1) Preparation of N-[(1S,2S)-2-amino-2-(4-fluorophenyl)-2-(6-fluoro-3-pyridyl)-1-methylethyl]-1-methyl-2-pyridone-5-carboxamide (1S,2S)-1-(4-fluorophenyl)-1-(6-fluoro-3-pyridyl)-1,2-propanediamine (50 mg) and 1-methyl-2-pyridone-5-carboxylic acid (66 mg) were dissolved in pyridine (5 mL). To the solution was added 1-(3-dimethylaminopropyl)-3-ethylcarbodiimide hydrochloride (95 mg), and the mixture was stirred at room temperature for 3 hours. The reaction mixture was concentrated in vacuo, and the residue was dissolved in chloroform. The solution was washed with brine, dried over anhydrous sodium sulfate, and filtered to remove the sodium sulfate. The organic solvent was evaporated in vacuo, and the residue was purified by column chromatography on silica gel (chloroform:methanol=19:1) to give the title compound (100 mg).

(2) Preparation of 5-[(4S,5S)-4-(4-fluorophenyl)-4-(6-fluoro-3-pyridyl)-5-methyl-2-imidazolin-2-yl]-1-methyl-2-pyridone N-[(1S,2S)-2-amino-2-(4-fluorophenyl)-2-(6-fluoro-3-pyridyl)-1-methylethyl]-1-methyl-2-pyridone-5-carboxamide (100 mg) was dissolved in toluene (2 mL), and ytterbium triflate (15 mg) was added. The mixture was heated in a sealed tube at 150° C. for 6 hours, and saturated aqueous sodium hydrogen carbonate was added. The mixture was extracted twice with chloroform, and the organic layer was dried over anhydrous sodium sulfate. After removal of the sodium sulfate by filtration, the organic solvent was evaporated in vacuo to give a residue. The residue was purified by column chromatography on silica gel (chloroform:methanol=9:1) to give the title compound (64 mg) as a white solid.

$^1$HNMR (300 MHz, CD$_3$OD, δ ppm):0.83 (3H, d, J=6.5 Hz), 3.60 (3H, s), 4.74 (1H, q, J=6.5 Hz), 6.57 (1H, d, J=9.6 Hz), 7.00–7.15 (3H, m), 7.20–7.30 (2H, m), 7.89 (1H, s), 7.90–8.05 (2H, m), 8.26 (2H, dd, J=2.4 Hz, 8.0 Hz)

Example 1-1

Preparation of 1-difluoromethyl-5-[(4S,5S)-4-(4-fluorophenyl)-4-(6-fluoro-3-pyridyl)-5-methyl-2-imidazolin-2-yl]-2-pyridone (1S,2S)-1-(4-fluorophenyl)-1-(6-fluoro-3-pyridyl)-1,2-propanediamine and 1-difluoromethyl-2-pyridone-5-carboxylic acid were condensed according to the procedure of Example 1, followed by dehydrative ring closure to give the title compound as a white solid.

$^1$HNMR (300 MHz, CD$_3$OD, δ ppm): 0.83 (3H, d, J=6.5 Hz), 4.76 (1H, q, J=6.5 Hz), 6.62 (1H, d, J=9.9 Hz), 7.00–7.15 (3H, m), 7.20–7.30 (2H, m), 7.78 (1H, t, J=59.9 Hz), 7.90–8.10 (2H, m), 8.25–8.35 (2H, m)

Example 1-2

Preparation of 1-ethyl-5-[(4S,5S)-4-(4-fluorophenyl)-4-(6-fluoro-3-pyridyl)-5-methyl-2-imidazolin-2-yl]-2-pyridone (1S,2S)-1-(4-fluorophenyl)-1-(6-fluoro-3-pyridyl)-1,2-propanediamine and 1-ethyl-2-pyridone-5-carboxylic acid were condensed according to the procedure of Example 1, followed by dehydrative ring closure to give the title compound as a white solid.

$^1$HNMR (300 MHz, CD$_3$OD, δ ppm): 0.83 (3H, d, J=6.5 Hz), 1.37 (3H, t, J=7.2 Hz), 4.07 (2H, q, J=7.2 Hz), 4.75 (1H, q, J=6.5 Hz), 6.57 (1H, d, J=9.6 Hz), 7.00–7.15 (3H, m), 7.20–7.30 (2H, m), 7.89 (1H, s), 7.90–8.00 (2H, m), 8.20–8.30 (2H, m)

Example 1-3

Preparation of 1-difluoromethyl-5-[(4R,5S)-4-(4-fluorophenyl)-4-(2-fluoro-4-pyridyl)-5-methyl-2-imidazolin-2-yl]-2-pyridone (1R,2S)-1-(4-fluorophenyl)-1-(2-fluoro-4-pyridyl)-1,2-propanediamine and 1-difluoromethyl-2-pyridone-5- carboxylic acid were condensed according to the procedure of Example 1, followed by dehydrative ring closure to give the title compound as a white solid.

¹HNMR (300 MHz, CD$_3$OD, δ ppm): 0.90 (3H, d, J=6.5 Hz), 4.70–4.90 (1H, m), 6.63 (1H, d, J=9.6 Hz), 6.99 (1H, brs), 7.05–7.20 (3H, m), 7.40–7.60 (2H, m), 7.78 (1H, t, J=59.7 Hz), 8.00–8.20 (2H, m), 8.32 (1H, s)

Example 1-4

Preparation of 1-(2,2-difluoroethyl-5-[(4S,5S)-4-(4-fluorophenyl)-4-(6-fluoro-3-pyridyl)-5-methyl-2imidazolin-2-yl]-2-pyridone (1S,2S)-1-(4-fluorophenyl)-1-(6-fluoro-3-pyridyl)-1,2-propanediamine and 1-(2,2-difluoroethyl)-2-pyridone-5carboxylic acid were condensed according to the procedure of Example 1, followed by dehydrative ring closure to give the title compound as a pale brown solid.

¹HNMR (300 MHz, CD$_3$OD, δ ppm): 0.83 (3H, d, J=6.3 Hz), 4.41 (2H, dt, J=3.3 Hz, 13.6 Hz), 4.70–4.80 (1H, m), 6.00–6.40 (1H, m), 6.61 (1H, d, J=9.6 Hz), 7.00–7.20 (3H, m), 7.20–7.40 (2H, m), 7.90–8.10 (2H, m), 8.20–8.40 (2H, m)

Example 1-5

Preparation of 5-[(4S,5S)-4-(4-fluorophenyl)-4-(6-fluoro-3-pyridyl)-5-methyl-2-imidazolin-2-yl]-1-propyl-2-pyridone (1S,2S)-1-(4-fluorophenyl)-1-(6-fluoro-3-pyridyl)-1,2-propanediamine and 1-propyl-2-pyridone-5-carboxylic acid were condensed according to the procedure of Example 1, followed by dehydrative ring closure to give the title compound as a white solid.

¹HNMR (400 MHz, CD$_3$OD, δ ppm): 0.84 (3H, d, J=5.6 Hz), 0.97 (3H, t, J=7.6 Hz), 1.80 (2H, sextet, J=7.6 Hz), 3.98 (2H, t, J=7.6 Hz), 4.70–4.80 (1H, m), 6.56 (1H, d, J=9.6 Hz), 7.00–7.10 (3H, m), 7.20–7.30 (2H, m), 7.90–8.00 (2H, m), 8.20–8.30 (2H, m)

Example 1-6

Preparation of 5-[(4S,5S)-4-(4-fluorophenyl)-4-(6-fluoro-3-pyridyl)-5-methyl-2-imidazolin-2-yl]-1-isopropyl-2-pyridone (1S,2S)-1-(4-fluorophenyl)-1-(6-fluoro-3-pyridyl)-1,2-propanediamine and 1-isopropyl-2-pyridone-5-carboxylic acid were condensed according to the procedure of Example 1, followed by dehydrative ring closure to give the title compound as a white solid.

¹HNMR (400 MHz, CD$_3$OD, δ ppm): 0.84 (3H, d, J=6.4 Hz), 1.42 (3H, d, J=4.4 Hz), 1.44 (3H, d, J=4.4 Hz), 4.75 (1H, q, J=6.4 Hz), 5.18 (1H, septet, J=4.4 Hz), 6.56 (1H, d, J=9.2 Hz), 7.00–7.10 (3H, m), 7.20–7.30 (2H, m), 7.90–8.00 (2H, m), 8.27 (2H, d, J=2.4 Hz)

Example 1-7

Preparation of Optically Active 1-difluoromethyl-5-[(5S)-4-(4-fluorophenyl)-5-methyl-4-(6-trifluoromethyl-3-pyridyl)-2-imidazolin-2-yl]-2-pyridone with the Diamine of Reference Example 3-2 as the Starting Material The diamine obtained in Reference Example 3-2 and 1-difluoromethyl-2-pyridone-5-carboxylic acid were condensed according to the procedure of Example 1, followed by dehydrative ring closure to give the title compound as a pale brown solid.

¹HNMR (400 MHz, CD$_3$OD, δ ppm): 0.88 (3H, d, J=7.2 Hz), 4.80–4.90 (1H, m), 6.63 (1H, d, J=9.6 Hz), 7.10 (2H, t, J=8.4 Hz), 7.45–7.55 (2H, m), 7.76 (1H, d, J=7.6 Hz), 7.78 (1H, t, J=60.0 Hz), 7.89 (1H, d, J=7.6 Hz), 8.09 (1H, d, J=9.6 Hz), 8.31 (1H, s), 8.53 (1H, s)

Example 1-8

Preparation of Optically Active 1-ethyl-5-[(5S)-4-(4-fluorophenyl)-5-methyl-4-(6-trifluoromethyl-3-pyridyl)-2-imidazolin-2-imidazolin-2-yl]-2-pyridone with the Diamine of Reference Example 3-2 as the Starting Material The diamine obtained in Reference Example 3-2 and 1-ethyl-2-pyridone-5-carboxylic acid were condensed according to the procedure of Example 1, followed by dehydrative ring closure to give the title compound as a white solid.

¹HNMR (400 MHz, CD$_3$OD, δ ppm): 0.89 (3H, d, J=6.4 Hz), 1.38 (3H, t, J=7.2 Hz), 4.07 (2H, q, J=7.2 Hz), 4.80–4.90 (1H, m), 6.57 (1H, d, J=9.6 Hz), 7.10 (2H, t, J=8.4 Hz), 7.45–7.55 (2H, m), 7.76 (1H, d, J=8.8 Hz), 7.85–7.90 (1H, m), 7.97 (1H, dd, J=2.0 Hz, 9.6 Hz), 8.27 (1H, d, J=2.0 Hz), 8.53 (1H, brs)

Example 1-9

Preparation of Optically Active 5-[(5S)-4-(4-fluorophenyl)-5-methyl-4-(6-trifluoromethyl-3-pyridyl)-2-imidazolin-2-yl]-1-propyl-2-pyridone with the Diamine of Reference Example 3-2 as the Starting Material The diamine obtained in Reference Example 3-2 and 1-propyl-2-pyridone-5-carboxylic acid were condensed according to the procedure of Example 1, followed by dehydrative ring closure to give the title compound as a white solid.

¹HNMR (400 MHz, CD$_3$OD, δ ppm): 0.89 (3H, t, J=6.4 Hz), 0.98 (3H, t, J=7.2 Hz), 1.81 (2H, sextet, J=7.2 Hz), 3.99 (2H, t, J=7.2 Hz), 4.80–5.00 (1H, m), 6.57 (1H, d, J=9.2 Hz), 7.10 (2H, t, J=8.8 Hz), 7.45–7.55 (1H, m), 7.76 (1H, d, J=1H, d, J=8.0 Hz), 7.85–7.90 (1H, m), 7.97 (1H, dd, J=2.8 Hz, 9.2 Hz), 8.24 (1H, d, J=2.8 Hz), 8.53 (1H, d, J=2.0 Hz)

Example 1-10

Preparation of Optically Active 1-(2,2-difluoroethyl)-5-[(5S)-4-(4-fluorophenyl)-5-methyl-4-(6-trifluoromethyl-3-pyridyl)-2-imidazolin-2-yl]-2-pyridone with the Diamine of Reference Example 3-2 as the Starting Material The diamine obtained in Reference Example 3-2 and 1-(2,2-difluoroethyl)-2-pyridone-5-carboxylic acid were condensed according to the procedure of Example 1, followed by dehydrative ring closure to give the title compound as a pale brown solid.

¹HNMR (300 MHz, CD$_3$OD, δ ppm): 0.89 (3H, t, J=6.4 Hz), 4.42 (2H, dt, J=4.0 Hz, 14.0 Hz), 4.80–4.90 (1H, m), 6.21 (1H, tt, J=4.0 Hz, 55.2 Hz), 6.62 (1H, d, J=9.6 Hz), 7.10 (2H, t, J=8.4 Hz), 7.45–7.55 (2H, m), 7.76 (1H, d, J=8.0 Hz), 7.80–7.90 (1H, m), 8.03 (1H, dd, J=2.8 Hz, 9.6 Hz), 8.23 (1H, d, J=2.8 Hz), 8.50–8.60 (1H, m)

Example 1-11

Preparation of Optically Active 3-chloro-1-ethyl-5-[(5S)-4-(4-fluorophenyl)-5-methyl-4-(6-trifluoromethyl-3-pyridyl)-2-imidazolin-2-yl]-2-pyridone with the Diamine of Reference Example 3-2 as the Starting Material The diamine obtained in Reference Example 3-2 and 3-chloro-1-ethyl-2-pyridone-5-carboxylic acid were condensed according to the procedure of Example 1, followed by dehydrative ring closure to give the title compound as a white solid.

¹HNMR (300 MHz, CD$_3$OD, δ ppm): 0.88 (3H, d, J=6.3 Hz), 1.40 (3H, m), 4.14 (2H, m), 7.15 (2H, m), 7.52 (2H, m), 7.78 (1H, d, J=7.8 Hz), 7.90 (1H, m), 8.21–8.28 (2H, m), 8.51 (1H, brs)

Example 1-12

Preparation of 5-[(4S,5S)-4-(3-bromo-4-fluorophenyl)-4-(6-fluoro-3-pyridyl)-5-methyl-2-imidazolin-2yl]-1-difluoromethyl-2-pyridone (1S,2S)-1-(3-bromo-4-fluorophenyl)-1-(6-fluoro-3-pyridyl)-1,2-propanediamine and 1-difluoromethyl-2- pyridone-5-carboxylic acid were condensed according to the procedure of Example 1, followed by dehydrative ring closure to give the title compound as a pale yellow solid.

$^1$HNMR (400 MHz, CD$_3$OD, δ ppm): 0.90–1.00 (3H, m), 4.70–4.80 (1H, m), 6.61 (1H, d, J=9.6 Hz), 7.00–7.10 (1H, m), 7.20–7.30 (2H, m), 7.60–7.70 (1H, m), 7.77 (1H, t, J=59.6 Hz), 8.00–8.20 (2H, m), 8.28 (2H, brs)

Example 1-13
Preparation of 1-difluoromethyl-5-[(4S,5S)-4-(4-fluorophenyl)-4-(2-fluoro-4-pyridyl)-5-methyl-2-imidazolin-2-yl]-2-pyridone (1S,2S)-1-(4-fluorophenyl)-1-(2-fluoro-4-pyridyl)-1,2-propanediamine and 1-difluoromethyl-2-pyridone-5-carboxylic acid were condensed according to the procedure of Example 1, followed by dehydrative ring closure to give the title compound as a white solid.

$^1$HNMR (400 MHz, CD$_3$OD, δ ppm): 0.87 (3H, d, J=7.2 Hz), 4.70–4.80 (1H, m), 6.62 (1H, d, J=9.6 Hz), 7.06 (2H, t, J=8.4 Hz), 7.16 (1H, brs), 7.20–7.30 (2H, m), 7.39 (1H, brd, 50 Hz), 7.77 (1H, t, J=59.6 Hz), 7.88 (1H, s), 8.05–8.10 (1H, m), 8.14 (1H, d, J=5.0 Hz), 8.30 (1H, brs)

Example 1-14
Preparation of 1-ethyl-5-[(4S,5S)-4-(4-fluorophenyl)-4-(2-fluoro-4-pyridyl)-5-methyl-2-imidazolin-2-yl]-2-pyridone (1S,2S)-1-(4-fluorophenyl)-1-(2-fluoro-4-pyridyl)-1,2-propanediamine and 1-ethyl-2-pyridone-5-carboxylic acid were condensed according to the procedure of Example 1, followed by dehydrative ring closure to give the title compound as a white solid.

$^1$HNMR (400 MHz, CD$_3$OD, δ ppm): 0.87 (3H, d, J=6.8 Hz), 1.37 (3H, t, J=7.6 Hz), 4.07 (2H, q, J=7.6 Hz), 4.70–4.80 (1H, m), 6.56 (1H, d, J=9.2 Hz), 7.06 (2H, t, J=8.8 Hz), 7.16 (1H, brs), 7.20–7.30 (2H, m), 7.30–7.40 (1H, m), 7.88 (1H, s), 7.96 (1H, dd, J=2.2 Hz, 9.2 Hz), 8.14 (1H, d, J=5.2 Hz), 8.25 (1H, d, J=2.2 Hz)

Example 1-15
Preparation of 1-(2,2-difluoroethyl)-5-[(4S,5S)-4-(4-fluorophenyl)-4-(2-fluoro-4-pyridyl)-5-methyl-2-imidazolin-2-yl]-2-pyridone (1S,2S)-1-(4-fluorophenyl)-1-(2-fluoro-4-pyridyl)-1,2-propanediamine and 1-(2,2-difluoroethyl)-2-pyridone-5-carboxylic acid were condensed according to the procedure of Example 1, followed by dehydrative ring closure to give the title compound as a yellow solid.

$^1$HNMR (400 MHz, CD$_3$OD, δ ppm): 0.87 (3H, d, J=6.4 Hz), 4.42 (2H, dt, J=4.0 Hz, 14.0 Hz), 4.70–4.80 (1H, m), 6.21 (1H, tt, J=14.0 Hz, 55.2 Hz), 6.61 (1H, d, J=9.6 Hz), 7.08 (2H, t, J=6.8 Hz), 7.16 (1H, s), 7.20–7.30 (2H, m), 7.38 (1H, d, J=5.2 Hz), 8.01 (1H, dd, J=2.4 Hz, 9.6 Hz), 8.14 (1H, d, J=5.2 Hz), 8.21 (1H, d, J=2.4 Hz)

Example 1-16
Preparation of Optically Active 1-difluoromethyl-5-[(5S)-4-(2-fluoro-4-pyridyl)-5-methyl-4-(4-trifluorophenyl)-2-imidazolin-2-yl]-2-pyridone with the Diamine of Reference Example 3 as the Starting Material The diamine obtained in Reference Example 3 and 1-difluoromethyl-2-pyridone-5-carboxylic acid were condensed according to the procedure of Example 1, followed by dehydrative ring closure to give the title compound as a white solid.

$^1$HNMR (400 MHz, CD$_3$OD, δ ppm): 0.85 (3.0H, d, J=6.0 Hz), 4.75 (1.0H, m), 6.62 (1.0H, d, J=10 Hz), 7.19 (1H, brs), 7.39 (1H, brs), 7.49 (2H, d, J=7.6 Hz), 7.64 (2H, d, J=7.6 Hz), 8.10–8.17 (2H, m), 8.30 (1H, brs)

Example 1-17
Preparation of 1-ethyl-5-[(4R,5S)-4-(4-fluorophenyl)-4-(2-fluoro-4-pyridyl)-5-methyl-2-imidazolin-2-yl]-2-pyridone (1R,2S)-1-(4-fluorophenyl)-1-(2-fluoro-4-pyridyl)-1,2-propanediamine and 1-ethyl-2-pyridone-5-carboxylic acid were condensed according to the procedure of Example 1, followed by dehydrative ring closure to give the title compound as a pale yellow solid.

$^1$HNMR (400 MHz, CD$_3$OD, δ ppm): 0.92 (3H, d, J=6.4 Hz), 1.37 (3H, t, J=7.6 Hz), 4.07 (2H, q, J=7.6 Hz), 4.75–4.85 (1H, m), 6.56 (1H, d, J=9.6 Hz), 6.99 (1H, s), 7.05–7.15 (3H, m), 7.45–7.55 (2H, m), 7.88 (1H, s), 7.96 (1H, dd, J=2.4 Hz, 9.6 Hz), 8.10 (1H, d, J=5.6 Hz), 8.26 (1H, d, J=2.4 Hz)

Example 1-18
Preparation of 3-chloro-1-ethyl-5-[(4S,5S)-4-(4-fluorophenyl)-4-(6-fluoro-3-pyridyl)-5-methyl-2-imidazolin-2-yl)]-2-pyridone (1S,2S)-1-(4-fluorophenyl)-1-(6-fluoro-3-pyridyl)-1,2-propanediamine and 3-chloro-1-ethyl-2-pyridone-5-carboxylic acid were condensed according to the procedure of Example 1, followed by dehydrative ring closure to give the title compound as a white solid.

$^1$HNMR (300 MHz, CD$_3$OD, δ ppm): 0.82 (3H, d, J=6.6 HZ), 1.38 (3H, t, d=7.2 Hz), 4.12 (2H, q, J=7.2 Hz), 4.74 (1H, m), 7.02–7.10 (3H, m), 7.26 (2H, m), 7.98 (1H, td, J=2.7 Hz, 8.4 Hz), 8.20–8.27 (3H, m)

Example 1-19
Preparation of Optically Active 5-[(5S)-4-(4-fluorophenyl)-5-methyl-4-(6-trifluoromethyl-3-pyridyl)-2-imidazolin-2-yl]-1-methyl-2-pyridone with the Diamine of Reference Example 3-2 as the Starting Material The diamine obtained in Reference Example 3-2 and 1-methyl-2-pyridone-5-carboxylic acid were condensed according to the procedure of Example 1, followed by dehydrative ring closure to give the title compound as a white solid.

$^1$HNMR (400 MHz, CD$_3$OD, δ ppm): 0.89 (3H, d, J=6.8 Hz), 3.61 (3H, s), 4.80–4.90 (1H, m), 6.57 (1H, d, J=9.6 Hz), 7.10 (2H, t, J=8.8 Hz), 7.45–7.55 (2H, m), 7.76 (1H, d, J=8.0 Hz), 7.85–7.90 (1H, m), 7.98 (1H, dd, J=2.8 Hz, 9.6 Hz), 8.27 (1H, d, J=2.8 Hz), 8.53 (1H, d, J=2.4 Hz)

Example 1-20
Preparation of 1-difluoromethyl-5-[(4R,5S)-4-(4-fluorophenyl)-4-(6-fluoro-3-pyridyl)-5-methyl-2-imidazolin-2-yl]-2-pyridone (1R,2S)-1-(4-fluorophenyl)-1-(6-fluoro-3-pyridyl)-1,2-propanediamine and 1-difluoromethyl-2-pyridone-5-carboxylic acid were condensed according to the procedure of Example 1, followed by dehydrative ring closure to give the title compound as a white solid.

$^1$HNMR (400 MHz, CD$_3$OD, δ ppm): 0.91 (3H, d, J=6.4 Hz), 4.75–4.85 (1H, m), 6.62 (1H, d, J=9.6 Hz), 7.01 (1H, dd, J=2.4 Hz, 8.4 Hz), 7.09 (2H, t, J=8.8 Hz), 7.45–7.55 (2H, m), 7.70–7.80 (1H, m), 7.77 (1H, t, J=59.6 Hz), 7.88 (1H, s), 8.01 (1H, d, J=2.8 Hz), 8.05–8.10 (1H, m), 8.30 (1H, brs)

Example 1-21
Preparation of Optically Active 1-difluoromethyl-5-[(5S)-4-(4-chlorophenyl)-4-(2-fluoro-4-pyridyl)-5-methyl-2-imidazolin-2-yl]-2-pyridone with the Diamine of Reference Example 3-1 as the Starting Material The diamine obtained in Reference Example 3-1 and 1-difluoromethyl-2-pyridone-5-carboxylic acid were condensed according to the procedure of Example 1, followed by dehydrative ring closure to give the title compound as a white solid.

¹HNMR (400 MHz, CD₃OD, δ ppm): 0.90 (3.0H, d, J=5.6 Hz), 4.74 (1.0H, m), 6.61 (1.0H, d, J=10 Hz), 6.99 (1.0H, brs), 7.10 (1H, brd, J=5.2 Hz), 7.36 (3.0H, brs), 7.46 (1.0H, brs), 8.10 (2.0H, brd, J=6.0 Hz), 8.29 (1.0H, brs)

Example 1-22
Preparation of Optically Active 1-ethyl-5-[(5S)-4-(2-fluoro-4-pyridyl)-5-methyl-4-(4-trifluoromethylphenyl)-2-imidazolin-2-yl]-2-pyridone with the Diamine of Reference Example 3 as the Starting Material The diamine obtained in Reference Example 3 and 1-ethyl-2-pyridone-5-carboxylic acid were condensed according to the procedure of Example 1, followed by dehydrative ring closure to give the title compound as a white solid.

¹HNMR (400 MHz, CD₃OD, δ ppm): 0.85 (3.0H, d, J=6.0 Hz), 1.37 (3.0H, t, J=7.6 Hz), 4.06 (2.0H, q, J=7.6 Hz), 4.78 (1.0H, m), 6.56 (1.0H, d, J=8.0 Hz), 7.18 (1.0H, m), 7.38 (1.0H, d, J=5.6 Hz), 7.47 (2.0H, d, J=8.0 Hz), 7.64 (2.0H, d, J=8.4 Hz), 7.97 (1.0H, dd, J=9.6 Hz, 2.8 Hz), 8.14 (1.0H, d, J=5.2 Hz), 8.27 (1.0H, d, J=2.4 Hz)

Example 1-23
Preparation of Optically Active 1-ethyl-5-[(5S)-4-(4-chlorophenyl)-4-(2-fluoro-4-pyridyl)-5-methyl-2-imidazolin-2-yl]-2-pyridone with the Diamine of Reference Example 3-1 as the Starting Material The diamine obtained in Reference Example 3-1 and 1-ethyl-2-pyridone-5-carboxylic acid were condensed according to the procedure of Example 1, followed by dehydrative ring closure to give the title compound as a white solid.

¹HNMR (400 MHz, CD₃OD, δ ppm): 0.91 (3.0H, d, J=6.8 Hz), 1.38 (3.0H, t, J=7.2 Hz), 4.07 (2.0H, q, J=7.2 Hz), 4.78 (1.0H, m), 6.56 (1.0H, d, J=9.6 Hz), 7.01 (1.0H, s), 7.10 (1.0H, m), 7.36 (2.0H, d, J=8.8 Hz), 7.45 (2.0H, d, J=8.0 Hz), 7.96 (1.0H, dd, J=9.6 Hz, 2.8 Hz), 8.11 (1.0H, d, J=5.6 Hz), 8.27 (1.0H, d, J=2.0 Hz)

Example 1-24
Preparation of 3-chloro-1-ethyl-5-[(4R,5S)-4-(4-fluorophenyl)-4-(2-fluoro-4-pyridyl)-5-methyl-2-imidazolin-2-yl]-2-pyridone (1R,2S)-1-(4-fluorophenyl)-1-(2-fluoro-4-pyridyl)-1,2-propanediamine and 3-chloro-1-ethyl-2-pyridone-5carboxylic acid were condensed according to the procedure of Example 1, followed by dehydrative ring closure to give the title compound as a white solid.

¹HNMR (300 MHz, CD₃OD, δ ppm): 0.89 (3.0H, m), 1.39 (3H, m), 4.12 (2H, m), 4.75 (1H, m), 7.0 (1H, brs), 7.10 (3H, brs), 7.49 (2H, m), 8.1 (1H, m), 8.25 (1H, brs), 8.26 (1H, m)

Example 1-25
Preparation of 1-ethyl-3-fluoro-5-[(4S,5S)-4-(4-fluorophenyl)-4-(6-fluoro-3-pyridyl)-5-methyl-2-imidazolin-2-yl]-2-pyridone (1S,2S)-1-(4-fluorophenyl)-1-(6-fluoro-3-pyridyl)-1,2-propanediamine and 1-ethyl-3-fluoro-2-pyridone-5carboxylic acid were condensed according to the procedure of Example 1, followed by dehydrative ring closure to give the title compound as a white solid.

¹HNMR (300 MHz, CD₃OD, δ ppm): 0.83 (3H, d, J=5.1 Hz), 1.38 (3H, t, J=7.2 Hz), 4.12 (2H, q, J=7.2 Hz), 4.74 (1H, m), 7.03–7.29 (5H, m), 7.81 (1H, d, J=10.2 Hz), 7.98 (1H, m), 8.10 (1H, s), 8.28 (1H, brs)

Example 1-26
Preparation of 3-chloro-5-[(4S,5S)-4-(4-fluorophenyl)-4-(6-fluoro-3-pyridyl)-5-methyl-2-imidazolin-2-yl]-1-methyl-2-pyridone (1S,2S)-1-(4-fluorophenyl)-1-(6-fluoro-3-pyridyl)-1,2-propanediamine and 3-chloro-1-methyl-2-pyridone-5carboxylic acid were condensed according to the procedure of Example 1, followed by dehydrative ring closure to give the title compound as a white solid.

¹HNMR (300 MHz, CD₃OD, δ ppm): 0.82 (3H, brs), 3.31 (3H, s), 4.75 (1H, m), 7.02–7.29 (5H, m), 7.98 (H, m), 8.21–8.29 (3H, m)

Example 1-27
Preparation of 1-ethyl-5-[(4S,5S)-4-(4-fluorophenyl)-4-(6-fluoro-3-pyridyl)-5-methyl-2-imidazolin-2-yl]-3-methyl-2-pyridone (1S,2S)-1-(4-fluorophenyl)-1-(6-fluoro-3-pyridyl)-1,2-propanediamine and 1-ethyl-3-methyl-2-pyridone-5-carboxylic acid were condensed according to the procedure of Example 1, followed by dehydrative ring closure to give the title compound as a white solid.

¹HNMR (400 MHz, CD₃OD, δ ppm): 0.84 (3.0H, d, J=6.8 Hz), 1.37 (3.0H, t, J=7.2 Hz), 2.16 (3.0H, s), 4.07 (2.0H, q, J=6.8 Hz), 4.74 (1.0H, q, J=6.8 Hz), 7.03 (1.0H, dd, J=8.0 Hz, 2.4 Hz), 7.05–7.09 (2.0H, m), 7.24–7.28 (2.0H, m), 7.85 (1.0H, m), 7.96–8.01(1.0H, m), 8.11 (1.0H, d, J=2.4 Hz), 8.27 (1.0H, d, J=2.8 Hz)

Example 1-28
Preparation of Optically Active 3-chloro-5-[(5S)-4-(4-fluorophenyl)-5-methyl-4-(6-trifluoromethyl-3-pyridyl)-2-imidazolin-2-yl]-1-methyl-2-pyridone with the Diamine of Reference Example 3-2 as the Starting Material The diamine obtained in Reference Example 3-2 and 3-chloro-1-methyl-2-pyridone-5-carboxylic acid were condensed according to the procedure of Example 1, followed by dehydrative ring closure to give the title compound as a white solid.

¹HNMR (400 MHz, CD₃OD, δ ppm): 0.88 (3H, d, J=6.3 Hz), 3.68 (3H, s), 7.12 (2H, t, J=8.1 Hz), 7.51 (2H, brs), 7.78 (1H, d, J=8.4 Hz), 7.90 (1H, m), 8.25 (2H, m), 8.55 (1H, s)

Example 1-29
Preparation of Optically Active 1-ethyl-3-fluoro-5-[(5S)-4-(4-fluorophenyl)-5-methyl-4-(6-trifluoromethyl-3-pyridyl)-2-imidazolin-2-yl]-2-pyridone with the Diamine of Reference Example 3-2 as the Starting Material The diamine obtained in Reference Example 3-2 and 1-ethyl-3-fluoro-2-pyridone-5-carboxylic acid were condensed according to the procedure of Example 1, followed by dehydrative ring closure to give the title compound as a white solid.

¹HNMR (300 MHz, CD₃OD, δ ppm): 0.89 (3H, d, J=6.6 Hz), 1.40 (3H, t, J=6.9 Hz), 4.14 (2H, q, J=7.2 Hz), 7.12 (2H, t, J=8.7 Hz), 7.52 (2H, m), 7.77–7.91 (3H, m), 8.15 (1H, s), 8.55 (1H, m)

Example 1-30
Preparation of 1-ethyl-5-[(4R,5S)-4-(4-fluorophenyl)-4-(6-fluoro-3-pyridyl)-5-methyl-2-imidazolin-2-yl]-2-pyridone (1R,2S)-1-(4-fluorophenyl)-1-(6-fluoro-3-pyridyl)-1,2-propanediamine and 1-ethyl-2-pyridone-5-carboxylic acid were condensed according to the procedure of Example 1, followed by dehydrative ring closure to give the title compound as a white solid.

¹HNMR (400 MHz, CD₃OD, δ ppm): 0.92 (3H, d, J=6.4 Hz), 1.37 (3H, t, J=7.6 Hz), 4.07 (2H, q, J=7.6 Hz), 4.80–4.90 (1H, m), 6.56 (1H, d, J=9.2 Hz), 7.01 (1H, dd, J=2.4 Hz, 8.8 Hz), 7.09 (2H, t, J=8.4 Hz), 7.45–7.55 (2H, m), 7.65–7.75 (1H, m), 7.88 (1H, s), 7.96 (1H, dd, J=2.4 Hz, 9.2 Hz), 8.01 (1H, d, J=2.4 Hz), 8.25 (1H, d, J=2.0 Hz)

Example 1-31
Preparation of 1-(2,2-difluoroethyl)-5-[(4R,5S)-4-(4-fluorophenyl)-4-(6-fluoro-3-pyridyl)-5-methyl-2-imidazolin-2-yl]-2-pyridone (1R,2S)-1-(4-fluorophenyl)-1-(6-fluoro-3-pyridyl)-1,2-propanediamine and 1-(2,2-difluoroethyl)-2-pyridone-5-carboxylic acid were condensed according to the procedure of Example 1, followed by dehydrative ring closure to give the title compound as a yellow solid.

$^1$HNMR (400 MHz, CD$_3$OD, δ ppm): 0.91 (3H, d, J=6.0 Hz), 4.42 (2H, dt, J=4.0 Hz, 13.6 Hz), 4.80–4.90 (1H, m), 6.21 (1H, tt, J=4.0 Hz, 55.2 Hz), 6.61 (1H, d, J=9.6 Hz), 7.01 (1H, dd, J=2.0 Hz, 8.0 Hz), 7.09 (2H, t, J=8.8 Hz), 7.45–7.55 (2H, m), 7.65–7.75 (1H, m), 7.88 (1H, s), 7.95–8.05 (2H, m), 8.21 (1H, d, J=2.0 Hz)

Example 1-32
Preparation of 5-[(4S,5S)-4-(4-fluorophenyl)-4-(6-fluoro-3-pyridyl)-5-methyl-2-imidazolin-2-yl]-1,3-dimethyl-2-pyridone (1S,2S)-1-(4-fluorophenyl)-1-(6-fluoro-3-pyridyl)-1,2-propanediamine and 1,3-dimethyl-2-pyridone-5-carboxylic acid were condensed according to the procedure of Example 1, followed by dehydrative ring closure to give the title compound as a white solid.

$^1$HNMR (400 MHz, CD$_3$OD, δ ppm): 0.83 (3.0H, d, J=6.8 Hz), 2.14 (3.0H, s), 3.60 (3.0H, s), 4.73 (1.0H, q, J=6.4 Hz), 7.02 (1H, dd, J=2.4 Hz, 8.4 Hz), 7.04–7.08 (2.0H, m), 7.23–7.26 (2H, m), 7.84 (1.0H, d, J=2.4 Hz), 7.95–7.99 (1.0H, m), 8.10 (1.0H, d, J=2.4 Hz), 8.26 (1.0H, d, J=2.4 Hz)

Example 1-33
Preparation of 3-chloro-5-[(4R,5S)-4-(4-fluorophenyl)-4-(6-fluoro-3-pyridyl)-5-methyl-2-imidazolin-2-yl]-1-methyl-2-pyridone (1R,2S)-1-(4-fluorophenyl)-1-(6-fluoro-3-pyridyl)-1,2-propanediamine and 3-chloro-1-methyl-2-pyridone-5-carboxylic acid were condensed according to the procedure of Example 1, followed by dehydrative ring closure to give the title compound as a white solid.

$^1$HNMR (300 MHz, CD$_3$OD, δ ppm): 0.90 (3H, d, J=6.6 Hz), 3.66 (3H, s), 4.76 (1H, m), 7.00–7.07 (1H, m), 7.10 (2H, t, J=8.4 Hz), 7.51 (2H, m), 7.72 (1H, m), 8.03 (1H, s), 8.23 (2H, d, J=7.8 Hz)

Example 1-34
Preparation of 3-chloro-1-ethyl-5-[(4R,5S)-4-(4-fluorophenyl)-4-(6-fluoro-3-pyridyl)-5-methyl-2-imidazolin-2-yl]-2-pyridone (1R,2S)-1-(4-fluorophenyl)-1-(6-fluoro-3-pyridyl)-1,2-propanediamine and 3-chloro-1-ethyl-2-pyridone-5-carboxylic acid were condensed according to the procedure of Example 1, followed by dehydrative ring closure to give the title compound as a white solid.

$^1$HNMR (300 MHz, CD$_3$OD, δ ppm): 0.90 (3H, d, J=6.6 Hz), 1.39 (3H, t, J=7.2 Hz), 4.13 (2H, q, J=7.5 Hz), 4.77 (1H, m), 7.02 (1H, dd, J=2.4 Hz, 8.7 Hz), 7.10 (2H, t, J=8.1 Hz), 7.50 (2H, m), 7.73 (1H, td, J=2.1 Hz, 9.0 Hz), 8.03 (1H, s), 8.23 (2H, d, J=11.4 Hz)

Example 1-35
Preparation of 1-ethyl-3-fluoro-5-[(4R,5S)-4-(4-fluorophenyl)-4-(6-fluoro-3-pyridyl)-5-methyl-2-imidazolin-2-yl]-2-pyridone (1R,2S)-1-(4-fluorophenyl)-1-(6-fluoro-3-pyridyl)-1,2-propanediamine and 1-ethyl-3-fluoro-2-pyridone-5-carboxylic acid were condensed according to the procedure of Example 1, followed by dehydrative ring closure to give the title compound as a white solid.

$^1$HNMR (300 MHz, CD$_3$OD, δ ppm): 0.91 (3H, d, J=6.6 Hz), 1.39 (3H, t, J=7.2 Hz), 4.13 (2H, q, J=6.9 Hz), 4.78 (1H, m), 7.02 (1H, d, J=8.7 Hz), 7.10 (2H, t, J=8.7 Hz), 7.51 (2H, m), 7.73 (1H, td, J=2.1 Hz, 9.2 Hz), 7.82 (1H, d, J=10.2 Hz), 8.03 (1H, s), 8.12 (1H, s)

Example 1-36
Preparation of Optically Active 1-difluoromethyl-5-[(5S)-4-(6-difluoromethyl-3-pyridyl)-4-(4-fluorophenyl)-5-methyl-2-imidazolin-2-yl]-2-pyridone with the Diamine of Reference Example 3-4 as the Starting Material The diamine obtained in Reference Example 3-4 and 1-difluoromethyl-2-pyridone-5-carboxylic acid were condensed according to the procedure of Example 1, followed by dehydrative ring closure to give the title compound as a white solid.

$^1$HNMR (300 MHz, CD$_3$OD, δ ppm): 0.84 (3H, brs), 6.62 (1H, d, J=9.6 Hz), 6.70 (1H, t, J=55 Hz), 7.08 (2H, t, J=8.7 Hz), 7.27 (2H, m), 7.67 (1H, d, J=8.4 Hz), 7.78 (1H, t, J=60 Hz), 8.05 (2H, m), 8.30 (1H, brs), 8.70 (1H, brs)

Example 1-37
Preparation of 5-[(4R,5S)-4-(4-fluorophenyl)-4-(6-fluoro-3-pyridyl)-5-methyl-2-imidazolin-2-yl]-1-methyl-2-pyridone (1R,2S)-1-(4-fluorophenyl)-1-(6-fluoro-3-pyridyl)1,2-propanediamine and 1-methyl-2-pyridone-5-carboxylic acid were condensed according to the procedure of Example 1, followed by dehydrative ring closure to give the title compound as a white solid.

$^1$HNMR (400 MHz, CD$_3$OD, δ ppm): 0.91 (3H, d, J=6.4 Hz), 3.61 (3H, s), 4.70–4.80 (1H, m), 6.57 (1H, d, J=9.2 Hz), 7.01 (1H, dd, J=2.4 Hz, 8.4 Hz), 7.09 (2H, t, J=8.8 Hz), 7.45–7.55 (2H, m), 7.65–7.75 (1H, m), 7.88 (1H, s), 7.97 (1H, dd, J=2.8 Hz, 9.2 Hz), 8.01 (1H, d, J=2.8 Hz), 8.25 (1H, d, J=2.4 Hz)

Example 1-38
Preparation of Optically Active 1-ethyl-3-fluoro-5-[(5S)-4(4-chlorophenyl)-4-(2-fluoro-4-pyridyl)-5-methyl-2-imidazolin-2-yl]-2-pyridone with the Diamine of Reference Example 3-4 as the Starting Material The diamine obtained in Reference Example 3-4 and 1-ethyl-3-fluoro-2-pyridone-5-carboxylic acid were condensed according to the procedure of Example 1, followed by dehydrative ring closure to give the title compound as a white solid.

$^1$HNMR (300 MHz, CD$_3$OD, δ ppm): 0.90 (3H, d, J=6.6 Hz), 1.39 (3H, t, J=7.2 Hz), 4.13 (2H, q, J=7.2 Hz), 4.79 (1H, m), 7.01 (1H, s), 7.11 (1H, d, J=4.8 Hz), 7.37 (2H, d, J=8.4 Hz), 7.46 (2H, brs), 7.82 (1H, d, J=10.2 Hz), 8.12 (2H, brs)

Example 1-39
Preparation of 3-ethyl-5-[(4S,5S)-4-(4-fluorophenyl)-4-(6-fluoro-3-pyridyl)-5-methyl-2-imidazolin-2-yl]-1-methyl-2-pyridone (1S,2S)-1-(4-fluorophenyl)-1-(6-fluoro-3-pyridyl)-1,2-propanediamine and 3-ethyl-1-methyl-2-pyridone-5-carboxylic acid were condensed according to the procedure of Example 1, followed by dehydrative ring closure to give the title compound as a white solid.

$^1$HNMR (400 MHz, CD$_3$OD, δ ppm): 0.83 (3.0H, d, J=6.4 Hz), 1.21 (3.0H, t, J=7.2 Hz), 2.55 (2.0H, q, J=7.2 Hz), 3.60 (3.0H, s), 4.73 (1.0H, q, J=6.4 Hz), 7.02 (1.0H, m), 7.03–7.08 (2.0H, m), 7.23–7.27 (2.0H, m), 7.84 (1H, d, J=2.8 Hz), 7.95–8.00 (1.0H, m), 8.11 (1.0H, d, J=2.4 Hz), 8.26 (1.0H, d, J=2.4 Hz)

Example 1-40
Preparation of 3-ethyl-5-[(4R,5S)-4-(4-fluorophenyl)-4-(2-fluoro-4-pyridyl)-5-methyl-2-imidazolin-2-yl]-1-methyl-2-pyridone (1R,2S)-1-(4-fluorophenyl)-1-(2-fluoro-4-pyridyl)-1,2-propanediamine and 3-ethyl-1-methyl-2-pyridone-5carboxylic acid were condensed according to the procedure of Example 1, followed by dehydrative ring closure to give the title compound as a white solid.

$^1$HNMR (400 MHz, CD$_3$OD, δ ppm): 0.91 (3.0H, d, J=6.4 Hz), 1.21 (3.0H, t, J=7.2 Hz), 2.56 (2.0H, q, J=7.2 Hz), 3.61 (3.0H, s), 4.80 (1.0H, m), 6.97 (1.0H, s), 7.06–7.11 (3.0H, m), 7.48 (2.0H, m), 7.84 (1.0H, d, J=2.8 Hz), 8.10 (1.0H, d, J=5.6 Hz), 8.12 (1.0H, d, J=2.0 Hz)

Example 1-41

Preparation of 3-ethyl-5-[(4R,5S)-4-(4-fluorophenyl)-4-(6-fluoro-3-pyridyl)-5-methyl-2-imidazolin-2-yl]-1-methyl-2-pyridone (1R,2S)-1-(4-fluorophenyl)-1-(6-fluoro-3-pyridyl)-1,2-propanediamine and 3-ethyl-1-methyl-2-pyridone-5carboxylic acid were condensed according to the procedure of Example 1, followed by dehydrative ring closure to give the title compound as a white solid.

$^1$HNMR (400 MHz, CD$_3$OD, δ ppm): 0.91 (3.0H, d, J=6.4 Hz), 1.21 (3.0H, t, J=7.2 Hz), 2.55 (2.0H, q, J=7.2 Hz), 3.60 (3.0H, s), 4.76 (2.0H, q, J=6.4 Hz), 7.01 (1.0H, dd, J=8.4 Hz, 2.4 Hz), 7.06–7.11 (2.0H, m), 7.47–7.51 (2.0H, m), 7.68–7.73 (1.0H, m), 7.84 (1.0H, d, J=2.4 Hz), 8.00 (1.0H, d, J=2.4 Hz), 8.12 (1.0H, d, J=2.4 Hz)

Example 1-42

Preparation of Optically Active 1-difluoromethyl-5-[(5S)-4-(6-difluoromethyl-3-pyridyl)-4-(4-fluorophenyl)-5-methyl-2-imidazolin-2-yl]-2-pyridone with the Diamine of Reference Example 3–5 as the Starting Material The diamine obtained in Reference Example 3-5 and 1-difluoromethyl-2-pyridone-5-carboxylic acid were condensed according to the procedure of Example 1, followed by dehydrative ring closure to give the title compound as a white solid.

$^1$HNMR (300 MHz, CD$_3$OD, δ ppm): 0.98 (3H, d, J=6.6 Hz), 6.63 (1H, d, J=9.6 Hz), 6.71 (1H, t, J=55.8 Hz), 7.11 (2H, t, J=9.0 Hz), 7.49–7.54 (2H, m), 7.66 (1H, d, J=8.1 Hz), 8.00 (1H, t, J=60.0 Hz), 8.07–8.11 (1H, m), 8.33 (1H, s), 8.47 (1H, s)

Example 1-43

Preparation of Optically Active 5-[(5S)-4-(6-difluoromethyl-3-pyridyl)-4-(4-fluorophenyl)-5-methyl-2-imidazolin-2-yl]-1-ethyl-2-pyridone with the Diamine of Reference Example 3-5 as the Starting Material The diamine obtained in Reference Example 3-5 and 1-ethyl-2-pyridone-5-carboxylic acid were condensed according to the procedure of Example 1, followed by dehydrative ring closure to give the title compound as a white solid.

$^1$HNMR (300 MHz, CD$_3$OD, δ ppm): 0.89 (3H, d, J=6.6 Hz), 1.37 (3H, t, J=6.3 Hz), 4.08 (2H, q, J=7.2 Hz), 6.58 (1H, d, J=9.9 Hz), 6.71 (1H, t, J=55.5 Hz), 7.1 (2H, t, J=9.0 Hz), 7.49–7.53 (2H, m), 7.66 (1H, d, J=8.1 Hz), 7.82 (1H, d, J=8.1 Hz), 7.98 (1H, dd, J=1.8 Hz, 9.4 Hz), 8.29 (1H, s)

Example 1-44

Preparation of Optically Active 5-[(5S)-4-(6-difluoromethyl-3-pyridyl)-4-(4-fluorophenyl)-5-methyl-2-imidazolin-2-yl]-1-ethyl-2-pyridone with the Diamine of Reference Example 3-4 as the Starting Material The diamine obtained in Reference Example 3-4 and 1-ethyl-2-pyridone-5-carboxylic acid were condensed according to the procedure of Example 1, followed by dehydrative ring closure to give the title compound as a white solid.

$^1$HNMR (300 MHz, CD$_3$OD, δ ppm): 0.85 (3H, d, J=6.3 Hz), 1.36 (3H, t, J=7.2 Hz), 4.06 (2H, q, J=6.3 Hz), 6.55 (1H, d, J=9.6 Hz), 6.70 (1H, t, J=55.5 Hz), 7.08 (2H, t, J=9.0 Hz), 7.25–7.29 (3H, m), 7.67 (1H, d, J=8.4 Hz), 7.94–8.04 (1H, m), 8.06 (1H, d, J=8.4 Hz), 8.26 (1H, s), 8.70 (1H, s)

Example 1-45

Preparation of Optically Active 5-[(5S)-4-(6-difluoromethyl-3-pyridyl)-4-(4-fluorophenyl)-5-methyl-2-imidazolin-2-yl]-1-ethyl-3-fluro-2-pyridone with the Diamine of Reference Example 3-5 as the Starting Material The diamine obtained in Reference Example 3-5 and 1-ethyl-3-fluoro-2-pyridone-5-carboxylic acid were condensed according to the procedure of Example 1, followed by dehydrative ring closure to give the title compound as a white solid.

$^1$HNMR (300 MHz, CD$_3$OD, δ ppm): 0.88 (3H, d, J=6.6 Hz), 1.39 (3H, t, J=6.6 Hz), 4.13 (2H, q, J=7.2 Hz), 6.71 (1H, t, J=54.3 Hz), 7.11 (2H, t, J=9.6 Hz), 7.48–7.53 (2H, m), 7.66 (1H, d, J=8.4 Hz), 7.81–7.89 (2H, m), 8.14 (1H, s), 8.47 (1H, s)

Example 1-46

Preparation of Optically Active 5-[(5S)-4-(6-difluoromethyl-3-pyridyl)-4-(4-fluorophenyl)-5-methyl-2-imidazolin-2-yl]-1-ethyl-3-fluro-2-pyridone with the Diamine of Reference Example 3-4 as the Starting Material The diamine obtained in Reference Example 3-4 and 1-ethyl-3-fluoro-2-pyridone-5-carboxylic acid were condensed according to the procedure of Example 1, followed by dehydrative ring closure to give the title compound as a white solid.

$^1$HNMR (300 MHz, CD$_3$OD, δ ppm): 0.85 (3H, d, J=6.6 Hz), 1.39 (3H, t, J=7.2 Hz), 4.12 (2H, q, J=6.9 Hz), 6.70 (1H, t, J=55.2 Hz), 7.05–7.30 (4H, m), 7.68 (1H, d, J=11.7 Hz), 7.81 (1H, dd, J=2.4 Hz, 9.0 Hz), 8.06 (1H, dd, J=1.8 Hz, 8.1 Hz), 8.11 (1H, s), 8.70 (1H, s)

Example 1-47

Preparation of 5-[(4S,5S)-4-(4-fluorophenyl)-4-(6-fluoro-3-pyridyl)-5-methyl-2-imidazolin-2-yl]-1-methoxy-2-pyridone (1S,2S)-1-(4-fluorophenyl)-1-(6-fluoro-3-pyridyl)-1,2-propanediamine and 1-methoxy-2-pyridone-5-carboxylic acid were condensed according to the procedure of Example 1, followed by dehydrative ring closure to give the title compound as a pale yellow solid.

$^1$HNMR (400 MHz, CD$_3$OD, δ ppm): 0.83 (3H, d, J=6.4 Hz), 4.08 (3H, s), 4.75 (1H, q, J=6.4 Hz), 6.69 (1H, d, J=9.6 Hz), 7.02 (1H, dd, J=2.4 Hz, 8.4 Hz), 7.04–7.08 (2H, m), 7.24–7.27 (2H, m), 7.95–7.99 (2H, m), 8.26 (1H, d, J=2.8 Hz), 8.47 (1H, d, J=2.4 Hz)

Example 1-48

Preparation of 5-[(4R,5S)-4-(4-fluorophenyl)-4-(6-fluoro-3-pyridyl)-5-methyl-2-2-imidazolin-2-yl]-1-methoxy-2-pyridone (1R,2S)-1-(4-fluorophenyl)-1-(6-fluoro-3-pyridyl)-1,2-propanediamine and 1-methoxy-2-pyridone-5-carboxylic acid were condensed according to the procedure of Example 1, followed by dehydrative ring closure to give the title compound as a white solid.

$^1$HNMR (400 MHz, CD$_3$OD, δ ppm): 0.92 (3H, d, J=6.4 Hz), 4.09 (3H, s), 4.81 (1H, q, J=6.8 Hz), 6.70 (1H, d, J=9.2 Hz), 7.01 (1H, dd, J=2.4 Hz, 8.4 Hz), 7.07–7.11 (2H, m), 7.47–7.51 (2H, m), 7.69–7.74 (1H, m), 7.98 (1H, dd, J=2.8 Hz, 9.6 Hz), 8.02 (1H, d, J=2.8 Hz), 8.51 (1H, d, J=2.4 Hz)

Example 1-49

Preparation of 1-ethoxy-5-[(4R,5S)-4-(4-fluorophenyl)-4-(6-fluoro-3-pyridyl)-5-methyl-2-imidazolin-2-yl]-2-pyridone (1R,2S)-1-(4-fluorophenyl)-1-(6-fluoro-3-pyridyl)-1,2-propanediamine and 1-ethoxy-2-pyridone-5-carboxylic acid were condensed according to the procedure of Example 1, followed by dehydrative ring closure to give the title compound as a white solid.

¹HNMR (400 MHz, CD₃OD, δ ppm): 0.92 (3H, d, J=6.8 Hz), 1.40 (3H, t, J=7.2 Hz), 4.34 (2H, q, J=6.8 Hz), 4.78 (1H, brs), 6.70 (1H, d, J=9.2 Hz), 7.01 (1.0H, dd, J=2.4 Hz, 8.8 Hz), 7.08–7.12 (2H, m), 7.47–7.55 (2H, m), 7.70–7.75 (1H, m), 7.99 (1H, dd, J=2.0 Hz, 10 Hz), 8.02 (1H, d, J=3.2 Hz), 8.47 (1H, d, J=2.4 Hz)

Example 1-50
Preparation of 1-cyclopropyl-5-[(4S,5S)-4-(4-fluorophenyl)-4-(6-fluoro-3-pyridyl)-5-methyl-2-imidazolin-2-yl]-2-pyridone (1S,2S)-1-(4-fluorophenyl)-1-(6-fluoro-3-pyridyl)-1,2-propanediamine and 1-cyclopropyl-5-methyl-2-pyridone-5-carboxylic acid were condensed according to the procedure of Example 1, followed by dehydrative ring closure to give the title compound as a white solid.

¹HNMR (300 MHz, CD₃OD, δ ppm): 0.88 (3H, d, J=6.3 Hz), 1.00–1.10 (2H, m), 1.15–1.24 (2H, m), 3.39–3.50 (1H, m), 4.78–4.85 (1H, m), 6.61 (1H, d, J=9.6 Hz), 7.05–7.17 (3H, m), 7.27–7.35 (2H, m), 7.98–7.88 (2H, m), 8.25 (1H, d, J=2.6 Hz), 8.32 (1H, d, J=0.9 Hz)

Example 1-51
Preparation of 1-cyclopropyl-5-[(4R,5S)-4-(4-fluorophenyl)-5-methyl-4-(6-trifluoromethyl-3-pyridyl)-2-imidazolin-2-yl]-2-pyridone (1R,2S)-1-(4-fluorophenyl)-1-(6-trifluoromethyl-3-pyridyl)-1,2-propanediamine and 1-cyclopropyl-2-pyridone-5-carboxylic acid were condensed according to the procedure of Example 1, followed by dehydrative ring closure to give the title compound as a white solid.

¹HNMR (300 MHz, CD₃OD, δ ppm): 0.88 (3H, d, J=6.9 Hz), 0.98–1.03 (2H, m), 1.12–1.17 (2H, m), 3.36–3.44 (1H, m), 4.78–4.90 (1H, m), 6.57 (1H, d, J=6.6 Hz), 7.11 (2H, t, J=8.4 Hz), 7.45–7.56 (2H, m), 7.77 (1H, d, J=8.0 Hz), 7.88 (1H, dd, J=6.6 Hz, 1.6 Hz), 7.99 (1H, dd, J=9.7 Hz, 2.4 Hz), 8.22 (1H, d, J=2.3 Hz), 8.53 (1H, s)

Example 1-52
Preparation of 5-[(4S,5S)-4-(4-fluorophenyl)-4-(2-fluoro-4-pyridyl)-5-methyl-2-imidazolin-2-yl]-1-methoxy-2-pyridone (1S,2S)-1-(4-fluorophenyl)-1-(2-fluoro-4-pyridyl)-1,2-propanediamine and 1-methoxy-2-pyridone-5-carboxylic acid were condensed according to the procedure of Example 1, followed by dehydrative ring closure to give the title compound as a white solid.

¹HNMR (400 MHz, CD₃OD, δ ppm): 0.82–0.90 (3H, brd), 4.08 (3H, s), 4.71–4.77 (1H, brs), 6.70 (1H, d, J=9.6 Hz), 7.04–7.08 (2H, m), 7.16 (1H, s), 7.23–7.28 (2H, m), 7.38 (1H, d, J=6.4 Hz), 7.99 (1H, d, J=9.6 Hz), 8.14 (1H, d, J=6.4 Hz), 8.48 (1H, d, J=2.0 Hz)

Example 1-53
Preparation of 5-[(4R,5S)-4-(4-fluorophenyl)-5-methyl-4-(6-trifluoromethyl-3-pyridyl)-2-imidazolin-2-yl]-1-methoxy-2-pyridone (1R,2S)-1-(4-fluorophenyl)-1-(6-trifluoromethyl-3-pyridyl)-1,2-propanediamine and 1-methoxy-2-pyridone-5-carboxylic acid were condensed according to the procedure of Example 1, followed by dehydrative ring closure to give the title compound as a white solid.

¹HNMR (400 MHz, CD₃OD, δ ppm): 0.88 (3H, d, J=6.4 Hz), 4.09 (3H, s), 4.78–4.88 (1H, m), 6.70 (1H, d, J=9.2 Hz), 7.07–7.11 (2H, m), 7.46–7.54 (2H, m), 7.76 (1H, d, J=8.0 Hz), 7.88 (1H, d, J=9.2 Hz), 8.01 (1H, brd, J=8.0 Hz), 8.50 (1H, d, J=2.4 Hz), 8.53 (1H, d, J=2.4 Hz)

Example 1-54
Preparation of 5-[(4R,5S)-4-(4-chlorophenyl)-4-(2-fluoro-4-pyridyl)-5-methyl-2-imidazolin-2-yl]-1-methoxy-2-pyridone (1R,2S)-1-(4-chlorophenyl)-1-(2-fluoro-4-pyridyl)-1,2-propanediamine and 1-methoxy-2-pyridone-5-carboxylic acid were condensed according to the procedure of Example 1, followed by dehydrative ring closure to give the title compound as a white solid.

¹HNMR (400 MHz, CD₃OD, δ ppm): 0.85–0.87 (3H, brd), 4.08 (3H, s), 4.71–4.75 (1H, m), 6.70 (1H, d, J=9.6 Hz), 7.04–7.06 (2H, m), 7.16 (1H, s), 7.23–7.27 (2H, m), 7.38 (1H, brd, J=6.4 Hz), 7.99 (1H, d, J=9.6 Hz), 8.14 (1H, brd, J=6.4 Hz), 8.48 (1H, d, J=2.0 Hz)

Example 1-55
Preparation of 1-difluoromethyl-5-[(4S,5S)-4-(4-fluorophenyl)-4-(6-fluoro-3-pyridyl)-5-methyl-2-imidazolin-2-yl]-3-methyl-2-pyridone (1S,2S)-1-(4-fluorophenyl)-1-(6-fluoro-3-pyridyl)-1,2-propanediamine and 1-difluoromethyl-3-methyl-2-pyridone-5-carboxylic acid were condensed according to the procedure of Example 1, followed by dehydrative ring closure to give the title compound as a pale yellow solid.

¹HNMR (400 MHz, CD₃OD, δ ppm): 0.81–0.88 (3H, brd), 2.16 (3H, s), 4.72–4.78 (1H, brs), 7.10–7.09 (3H, m), 7.23–7.28 (2H, m), 7.80 (1H, t, J=60 Hz), 7.92–8.20 (2H, m), 8.16–8.19 (1H, brs), 8.25–8.30 (1H, brs)

Example 1-56
Preparation of 1-difluoromethyl-5-[(4R,5S)-4-(4-fluorophenyl)-4-(6-fluoro-3-pyridyl)-5-methyl-2-imidazolin-2-yl]-3-methyl-2-pyridone (1R,2S)-1-(4-fluorophenyl)-1-(6-fluoro-3-pyridyl)-1,2-propanediamine and 1-difluoromethyl-3-methyl-2-pyridone-5-carboxylic acid were condensed according to the procedure of Example 1, followed by dehydrative ring closure to give the title compound as a pale yellow solid.

¹HNMR (400 MHz, CD₃OD, δ ppm): 0.91 (3H, d, J=6.0 Hz), 2.17 (3H, s), 4.72–4.80 (1H, brs), 7.02 (1H, dd, J=2.4 Hz, 8.8 Hz), 7.08–7.12 (2H, m), 7.47–7.54 (2H, m), 7.70–7.74 (1H, m), 7.81 (1H, t, J=60 Hz), 7.92–7.97 (1H, brs), 8.01 (1H, d, J=2.8 Hz), 8.16–8.21 (1H, brs)

Example 1-57
Preparation of 1-difluoromethyl-5-[(4S,5S)-4-(4-fluorophenyl)-4-(6-fluoro-3-pyridyl)-5-methyl-2-imidazolin-2-yl]-3-methoxy-2-pyridone (1S,2S)-1-(4-fluorophenyl)-1-(6-fluoro-3-pyridyl)-1,2-propanediamine and 1-difluoromethyl-3-methoxy-2-pyridone-5-carboxylic acid were condensed according to the procedure of Example 1, followed by dehydrative ring closure to give the title compound as a white solid.

¹HNMR (400 MHz, CD₃OD, δ ppm): 0.80–0.88 (3H, brs), 3.90 (3H, s), 4.72–4.80 (1H, brs), 7.02–7.09 (3H, m), 7.25–7.30 (2H, m), 7.42 (1H, s), 7.83 (1H, t, J=60 Hz), 7.94–8.02 (2H, m), 8.26 (1H, brs)

Example 1-58
Preparation of 1-difluoromethyl-5-[(4R,5S)-4-(4-fluorophenyl)-4-(6-fluoro-3-pyridyl)-5-methyl-2-imidazolin-2-yl]-3-methoxy-2-pyridone (1R,2S)-1-(4-fluorophenyl)-1-(6-fluoro-3-pyridyl)-1,2-propanediamine and 1-difluoromethyl-3-methoxy-2- pyridone-5-carboxylic acid were condensed according to the procedure of Example 1, followed by dehydrative ring closure to give the title compound as a pale yellow solid.

¹HNMR (400 MHz, CD₃OD, δ ppm): 0.93 (3H, d, J=6.0 Hz), 3.91 (3H, s), 4.75–4.83 (1H, brs), 7.02 (1H, dd, J=2.8 Hz, 8.8 Hz), 7.08–7.13 (1H, m), 7.42–7.45 (1H, brs), 7.48–7.53 (2H, m), 7.71–7.74 (1H, m), 7.84 (1H, t, J=60 Hz), 7.94–7.98 (1H, brs), 8.02 (1H, d, J=3.2 Hz)

Example 1-59

Preparation of 5-[(5S)-4,4-bis(4-fluorophenyl)-5-methyl-2-imidazolin-2-yl]-1-methoxy-2-pyridone (2S)-1,1-bis(4-fluorophenyl)-1,2-propanediamine and 1-methoxy-2-pyridone-5-carboxylic acid were condensed according to the procedure of Example 1, followed by dehydrative ring closure to give the title compound as a white solid.

¹HNMR (400 MHz, CD₃OD, δ ppm): 0.87 (30H, d, J=6.0 Hz), 4.09 (3H, s), 4.24 (1H, m), 6.70 (1H, d, J=9.6 Hz), 7.00–7.08 (3H, m), 7.16–7.20 (2H, m), 7.44–7.47 (2H, m), 7.98 (1H, dd, J=2.4 Hz, 9.6 Hz), 8.48 (1H, d, J=2.4 Hz)

Example 1-60

Preparation of 1-difluoromethyl-5-[(4S,5S)-4-(6-cyclopropyl-3-pyridyl)-4-(4-fluorophenyl)-5-methyl-2-imidazolin-2-yl]-2-pyridone (1S,2S)-1-(6-cyclopropyl-3-pyridyl)-1-(4-fluorophenyl)-1,2-propanediamine and 1-difluoromethyl-2pyridone-5-carboxylic acid were condensed according to the procedure of Example 1, followed by dehydrative ring closure to give the title compound as a brown solid.

¹HNMR (300 MHz, CD₃OD, δ ppm): 0.88 (3H, d, J=6.3 Hz), 0.90–1.10 (4H, m), 2.07–2.18 (1H, m), 4.80 (1H, q, J=6.4 Hz), 6.67 (1H, d, J=9.8 Hz), 7.11 (2H, t, J=8.6 Hz), 7.26 (1H, d, J=7.2 Hz), 7.30 (2H, dd, J=8.5 Hz, 5.4 Hz), 7.77 (1H, dd, J=8.2 Hz, 2.6 Hz), 7.83 (1H, t, J=60.0 Hz), 8.11 (1H, dd, J=9.7 Hz, 2.5 Hz), 8.36 (1H, d, J=2.0 Hz), 8.46 (1H, d, J=1.6 Hz)

Example 1-61

Preparation of 5-[(4S,5S)-4-(6-cyclopropyl-3-pyridyl)-4-(4-fluorophenyl)-5-methyl-2-imidazolin-2-yl]-1-ethyl-2-pyridone (1S,2S)-1-(6-cyclopropyl-3-pyridyl)-1-(4-fluorophenyl)-1,2-propanediamine and 1-ethyl-2-pyridone-5carboxylic acid were condensed according to the procedure of Example 1, followed by dehydrative ring closure to give the title compound as a white solid.

¹HNMR (300 MHz, CD₃OD, δ ppm): 0.88 (3H, d, J=6.5 Hz), 0.92–1.10 (4H, m), 1.42 (3H, t, J=7.2 Hz), 2.07–2.19 (1H, m), 4.11 (2H, q, J=7.3 Hz), 4.79 (1H, q, J=6.4 Hz), 6.62 (1H, d, J=9.6 Hz), 7.12 (2H, t, J=8.7 Hz), 7.23 (1H, d, J=8.4 Hz), 7.30 (2H, dd, J=8.9 Hz, 5.3 Hz), 7.77 (1H, dd, J=8.4 Hz, 2.4 Hz), 8.00 (1H, dd, J=9.3 Hz, 2.4 Hz), 8.31 (1H, d, J=2.3 Hz), 8.47 (1H, d, J=2.5 Hz)

Example 1-62

Preparation of 5-[(4S,5S)-4-(4-chlorophenyl)-4-(6-fluoro-3-pyridyl)-5-methyl-2-imidazolin-2-yl]-1-methoxy-2-pyridone (1S,2S)-1-(4-chlorophenyl)-1-(6-fluoro-3-pyridyl)-1,2-propanediamine and 1-methoxy-2-pyridone-5-carboxylic acid were condensed according to the procedure of Example 1, followed by dehydrative ring closure to give the title compound as a white solid.

¹HNMR (400 MHz, CD₃OD, δ ppm): 0.83 (3H, d, J=4.4 Hz), 4.08 (3H, s), 4.75–4.80 (1H, brs), 6.69 (1H, d, J=9.6 Hz), 7.02 (1H, d, J=8.8 Hz), 7.23 (2H, d, J=8.0 Hz), 7.33 (2H, d, J=8.4 Hz), 7.92–8.00 (2H, m), 8.26 (1H, brs), 8.47 (1H, d, J=2.4 Hz)

Example 1-63

Preparation of 5-[(4S,5S)-4-(6-fluoro-3-pyridyl)-5-methyl-4-(4-trifluoromethylphenyl)-2-imidazolin-2-yl]-1-methoxy-2-pyridone (1S,2S)-1-(6-fluoro-3-pyridyl)-1-(4-trifluoromethylphenyl)-1,2-propanediamine and 1-methoxy-2-pyridone-5-carboxylic acid were condensed according to the procedure of Example 1, followed by dehydrative ring closure to give the title compound as a white solid.

¹HNMR (400 MHz, CD₃OD, δ ppm): 0.97 (3H, d, J=6.8 Hz), 4.12 (3H, s), 5.18–5.22 (1H, brs), 6.77 (1H, d, J=9.2 Hz), 7.14 (1H, d, J=6.0 Hz), 7.47 (2H, d, J=8.0 Hz), 7.74 (2H, d, J=8.0 Hz), 7.91 (1H, d, J=10.0 Hz), 7.95–8.02 (1H, m), 8.33 (1H, s), 8.77 (1H, s)

Example 1-64

Preparation of 5-[(4R,5S)-4-(4-fluorophenyl)-4-(2-fluoro-4-pyridyl)-5-methyl-2-imidazolin-2-yl]-1-methoxy-2-pyridone (1R,2S)-1-(4-fluorophenyl)-1-(2-fluoro-4-pyridyl)-1,2-propanediamine and 1-methoxy-2-pyridone-5-carboxylic acid were condensed according to the procedure of Example 1, followed by dehydrative ring closure to give the title compound as a white solid.

¹HNMR (400 MHz, CD₃OD, δ ppm): 0.92 (3H, d, J=6.8 Hz), 4.09 (3H, s), 4.82 (1H, q, J=6.4 Hz), 6.71 (1H, d, J=9.6 Hz), 7.00 (1H, s), 7.07–7.12 (3H, m), 7.47–7.51 (2H, m), 7.46 (2H, d, J=8.4 Hz), 8.00 (1H, dd, J=2.8 Hz, 6.8 Hz), 8.11 (1H, d, J=5.6 Hz), 8.50 (1H, d, J=2.4 Hz)

Example 1-65

Preparation of 1-cyclopropyl-5-[(4R,5S)-4-(4-fluorophenyl)-4-(6-fluoro-3-pyridyl)-5-methyl-2-imidazolin-2-yl]-2-pyridone (1R,2S)-1-(4-fluorophenyl)-1-(6-fluoro-3-pyridyl)-1,2-propanediamine and 1-cyclopropyl-2-pyridone-5-carboxylic acid were condensed according to the procedure of Example 1, followed by dehydrative ring closure to give the title compound as a white solid.

¹HNMR (300 MHz, CD₃OD, δ ppm): 0.91 (3H, d, J=6.5 Hz), 0.96–1.04 (2H, m), 1.12–1.19 (2H, m), 3.34–3.42 (1H, m), 4.72–4.82 (1H, m), 6.56 (1H, d, J=9.5 Hz), 7.02 (1H, dd, J=8.6 Hz, 2.7 Hz), 7.10 (2H, t, J=8.8 Hz), 7.44–7.54 (2H, m), 7.72 (1H, td, J=8.6 Hz, 2.4 Hz), 7.97 (1H, dd, J=9.6 Hz, 2.4 Hz), 8.02 (1H, d, J=2.4 Hz), 8.21 (1H, d, J=2.4 Hz)

Example 1-66

Preparation of 1-cyclopropyl-5-[(4R,5S)-4-(4-fluorophenyl)-4-(2-fluoro-4-pyridyl)-5-methyl-2-imidazolin-2-yl]-2-pyridone (1R,2S)-1-(4-fluorophenyl)-1-(2-fluoro-4-pyridyl)-1,2-propanediamine and 1-cyclopropyl-2-pyridone-5-carboxylic acid were condensed according to the procedure of Example 1, followed by dehydrative ring closure to give the title compound as a white solid.

¹HNMR (300 MHz, CD₃OD, δ ppm): 0.90 (3H, d, J=6.6 Hz), 0.96–1.03 (2H, m), 1.10–1.20 (2H, m), 3.34–3.43 (1H, m), 4.73–4.90 (1H, m), 6.57 (1H, d, J=9.3 Hz), 6.98 (1H, s), 7.05–7.16 (3H, m), 7.44–7.53 (2H, m), 7.98 (1H, dd, J=9.5 Hz, 2.6 Hz), 8.12 (1H, d, J=5.4 Hz), 8.22 (1H, d, J=2.4 Hz)

Example 1-67

Preparation of 1-ethyl-5-[(5S)-4,4-bis(6-fluoro-3-pyridyl)-5-methyl-2-imidazolin-2-yl]-2-pyridone (2S)-1,1-bis(6-fluoro-3-pyridyl)-1,2-propanediamine and 1-ethyl-2-pyridone-5-carboxylic acid were condensed according to the procedure of Example 1, followed by dehydrative ring closure to give the title compound as a white solid.

$^1$HNMR (400 MHz, CD$_3$OD, δ ppm): 0.88 (3H, d, J=6.4 Hz), 1.37 (3H, t, J=6.8 Hz), 4.07 (2H, q, J=6.8 Hz), 4.80–4.90 (1H, m), 6.56 (1H, d, J=9.2 Hz), 7.00–7.10 (2H, m), 7.70–7.90 (1H, m), 7.88 (1H, s), 7.96 (1H, dd, J=2.4 Hz, 9.2 Hz), 7.95–8.05 (1H, m), 8.13 (1H, d, J=2.8 Hz), 8.26 (1H, d, J=2.0 Hz), 8.32 (1H, d, J=2.0 Hz)

Example 1-68

Preparation of 5-[(5S)-4,4-bis(6-fluoro-3-pyridyl)-5-methyl-2-imidazolin-2-yl]-1-difluoromethyl-2-pyridone (2S)-1,1-bis(6-fluoro-3-pyridyl)-1,2-propanediamine and 1-difluoromethyl-2-pyridone-5-carboxylic acid were condensed according to the procedure of Example 1, followed by dehydrative ring closure to give the title compound as a white solid.

$^1$HNMR (400 MHz, CD$_3$OD, δ ppm): 0.88 (3H, d, J=6.4H), 4.80–4.90 (1H, m), 6.61 (1H, d, J=9.6 Hz), 7.00–7.10 (2H, m), 7.77 (1H, t, J=59.6 Hz), 8.00–8.20 (3H, m), 8.25–8.35 (2H, m)

Example 1-69

Preparation of 1-cyclopropyl-5-[(4S,5S)-4-(4-fluorophenyl)-4-(2-fluoro-4-pyridyl)-5-methyl-2-imidazolin-2-yl]-2-pyridone (1S,2S)-1-(4-fluorophenyl)-1-(2-fluoro-4-pyridyl)-1,2-propanediamine and 1-cyclopropyl-2-pyridone-5-carboxylic acid were condensed according to the procedure of Example 1, followed by dehydrative ring closure to give the title compound as a white solid.

$^1$HNMR (300 MHz, CD$_3$OD, δ ppm): 0.86 (3H, d, J=6.3 Hz), 0.97–1.02 (2H, m), 1.10–1.20 (2H, m), 3.33–3.44 (1H, m), 4.72 (1H, q, J=6.7 Hz), 6.57 (1H, d, J=9.5 Hz), 7.07 (2H, t, J=8.7 Hz), 7.16 (1H, s), 7.26 (2H, dd, J=8.6 Hz, 5.3 Hz), 7.39 (1H, dt, J=5.2 Hz, 1.3 Hz), 7.99 (1H, dd, J=9.6 Hz, 2.4 Hz), 8.16 (1H, d, J=5.6 Hz), 8.21 (1H, d, J=2.6 Hz)

Example 1-70

Preparation of 1-difluoromethyl-3-ethyl-5-[(4S,5S)-4-(4-fluorophenyl)-4-(6-fluoro-3-pyridyl)-5-methyl-2-imidazolin-2-yl]-2-pyridone (1S,2S)-1-(4-fluorophenyl)-1-(6-fluoro-3-pyridyl)-1,2-propanediamine and 1-difluoromethyl-2-pyridone-5-carboxylic acid were condensed according to the procedure of Example 1, followed by dehydrative ring closure to give the title compound as a white solid.

$^1$HNMR (400 MHz, CD$_3$OD, δ ppm): 0.85 (3H, d, J=6.4 Hz), 1.23 (3H, t, J=7.6 Hz), 2.57 (2H, q, J=7.2 Hz), 4.76–4.83 (1H, brs), 7.03–7.11 (3H, m), 7.24–7.28 (2H, m), 7.81 (1H, t, J=60 Hz), 7.90 (1H, s), 7.95–8.00 (1H, m), 8.20 (1H, s), 8.27 (1H, s)

Example 1-71

Preparation of 1-difluoromethyl-3-ethyl-5-[(4R,5S)-4-(4-fluorophenyl)-4-(6-fluoro-3-pyridyl)-5-methyl-2-imidazolin-2-yl]-2-pyridone (1R,2S)-1-(4-fluorophenyl)-1-(6-fluoro-3-pyridyl)-1,2-propanediamine and 1-difluoromethyl-3-ethyl-2-pyridone-5-carboxylic acid were condensed according to the procedure of Example 1, followed by dehydrative ring closure to give the title compound as a white solid.

$^1$HNMR (400 MHz, CD$_3$OD, δ ppm): 0.93 (3H, d, J=6.4 Hz), 1.24 (3H, t, J=7.2 Hz), 2.57 (2H, q, J=7.2 Hz), 4.82–4.89 (1H, brs), 7.03 (1H, dd, J=2.4 Hz, 8.4 Hz), 7.09–7.13 (2H, m), 7.48–7.52 (2H, m), 7.70–7.75 (1H, m), 7.81 (1H, t, J=60 Hz), 7.90–7.93 (1H, m), 8.02 (1H, d, J=2.4 Hz), 8.22 (1H, d, J=2.0 Hz)

Example 1-72

Preparation of 1-difluoromethoxy-5-[(4S,5S)-4-(4-fluorophenyl)-4-(6-fluoro-3-pyridyl)-5-methyl-2-imidazolin-2-yl]-2-pyridone (1S,2S)-1-(4-fluorophenyl)-1-(6-fluoro-3-pyridyl)-1,2-propanediamine and 1-difluoromethoxy-2-pyridone-5-carboxylic acid were condensed according to the procedure of Example 1, followed by dehydrative ring closure to give the title compound as a white solid.

$^1$HNMR (400 MHz, CD$_3$OD, δ ppm): 0.83 (3H, d, J=6.8 Hz), 4.75 (1H, q, J=6.4 Hz), 6.74 (1H, d, J=9.6 Hz), 7.06 (1H, t, J=70 Hz), 7.02–7.08 (3H, m), 7.23–7.26 (2H, m), 7.95–7.99 (1H, m), 8.05 (1H, d, J=9.6 Hz), 8.26 (1H, s), 8.42 (1H, s)

Example 1-73

Preparation of Optically Active 5-[(5S)-4-(6-difluoromethyl-3-pyridyl)-4-(4-fluorophenyl)-5-methyl-2-imidazolin-2-yl]-1-methoxy-2-pyridone with the Diamine of Reference Example 3-5 as the Starting Material The diamine obtained in Reference Example 3-5 and 1-methoxy-2-pyridone-5-carboxylic acid were condensed according to the procedure of Example 1, followed by dehydrative ring closure to give the title compound as a yellow solid.

$^1$HNMR (300 MHz, CD$_3$OD, δ ppm): 0.88 (3H, d, J=6.6 Hz), 6.71 (1H, t, J=55.2 Hz), 6.73 (1H, s), 7.11 (2H, t, J=9.0 Hz), 7.48–7.53 (2H, m), 7.66 (1H, d, J=8.1 Hz), 7.83 (1H, d, J=8.4 Hz), 8.02 (1H, dd, J=2.4 Hz, 9.6 Hz), 8.48 (1H, s), 8.52 (1H, s)

Example 1-74

Preparation of 1-difluoromethoxy-5-[(4R,5S)-4-(4-fluorophenyl)-4-(6-fluoro-3-pyridyl)-5-methyl-2-imidazolin-2-yl]-2-pyridone (1R,2S)-1-(4-fluorophenyl)-1-(6-fluoro-3-pyridyl)-1,2-propanediamine and 1-difluoromethoxy-2-pyridone-5-carboxylic acid were condensed according to the procedure of Example 1, followed by dehydrative ring closure to give the title compound as a white solid.

$^1$HNMR (400 MHz, CD$_3$OD, δ ppm): 0.90 (3H, d, J=6.8 Hz), 4.75–4.83 (1H, brs), 6.75 (1H, d, J=10 Hz), 7.01 (1H, dd, J=2.4 Hz, 8.8 Hz), 7.07 (1H, t, J=70 Hz), 7.07–7.11 (2H, m), 7.45–7.53 (2H, m), 7.68–7.72 (1H, m), 8.00 (1H, d, J=2.4 Hz), 8.04 (1H, d, J=8.0 Hz), 8.43 (1H, s)

Example 1-75

Preparation of 1-difluoromethyl-3-ethyl-5-[(4R,5S)-4-(4-fluorophenyl)-4-(2-fluoro-4-pyridyl)-5-methyl-2-imidazolin-2-yl]-2-pyridone (1R,2S)-1-(4-fluorophenyl)-1-(2-fluoro-4-pyridyl)-1,2-propanediamine and 1-difluoromethyl-3-ethyl-2-pyridone-5-carboxylic acid were condensed according to the procedure of Example 1, followed by dehydrative ring closure to give the title compound as a white solid.

$^1$HNMR (400 MHz, CD$_3$OD, δ ppm): 0.91 (3H, d, J=6.0 Hz), 1.23 (1H, t, J=7.6 Hz), 2.57 (1H, q, J=7.6 Hz), 4.73–4.85 (1H, brs), 6.92–7.00 (1H, brs), 7.07–7.14 (3H, m), 7.44–7.54 (2H, brs), 7.81 (1H, t, J=60 Hz), 7.91–7.95 (1H, brs), 8.11 (1H, d, J=5.2 Hz), 8.16–8.24 (1H, brs)

Example 1-76

Preparation of 1-difluoromethyl-5-[(4S,5R)-4-(4-fluorophenyl)-4-(6-fluoro-3-pyridyl)-5-hydroxymethyl-2-imidazolin-2-yl]-2-pyridone trifluoroacetate (1S,2R)-1-(4-fluorophenyl)-1-(6-fluoro-3-pyridyl)-3-hydroxy-1,2-propanediamine and 1-difluoromethyl-2-pyridone-5-carboxylic acid were condensed according to the procedure of Example 1, followed by dehydrative ring closure to give the title compound as a brown solid.

$^1$HNMR (400 MHz, CD$_3$OD, δ ppm): 3.30–3.40 (2H, m), 5.19 (1H, t, J=5.6 Hz), 6.74 (1H, d, J=10.0 Hz), 7.10–7.20 (3H, m), 7.25–7.35 (2H, m), 7.81 (1H, t, J=59.2 Hz), 7.94 (1H, dd, J=2.4 Hz, 10.0 Hz), 8.00–8.10 (1H, m), 8.38 (1H, d, J=3.2 Hz), 8.78 (1H, d, J=2.4 Hz)

Example 1-77

Preparation of Sodium 1-difluoromethyl-5-[(4S,5S)-4-(4-fluorophenyl)-4-(6-fluoro-3-pyridyl)-5-methyl-2-imidazolin-2-yl]-2-pyridone-3-olate (1S,2S)-1-(4-fluorophenyl)-1-(6-fluoro-3-pyridyl)-1,2-propanediamine and 1-difluoromethyl-3-methoxy-2-pyridone-5-carboxylic acid were condensed according to the procedure of Example 1, subjected to dehydrative ring closure, followed by deprotection of the resulting product to give the title compound as a pale yellow solid.

$^1$HNMR (400 MHz, CD$_3$OD, δ ppm): 0.86 (3H, d, J=6.8 Hz), 4.83 (1H, q, J=6.4 Hz), 7.05 (1H, dd, J=3.2, 8.4 Hz), 7.06–7.11 (2H, m), 7.22–7.26 (3H, m), 7.82 (1H, t, J=60.0 Hz), 7.90 (1H, d, J=2.0 Hz), 7.95–8.00 (1H, m), 8.27 (1H, d, J=2.4 Hz)

Example 1-78

Preparation of 1-difluoromethyl-5-[(4S,5S)-4-(4-fluoro-3-hydroxyphenyl)-4-(6-fluoro3-hydroxyphenyl)-4-(6-fluoro-3-pyridyl)-5-methyl-2-imidazolin-2-yl]-2-pyridone (1S,2S)-1-(4-fluoro-3-methoxymethoxyphenyl)-1-(6-fluoro-3-pyridyl)-1,2-propanediamine and 1-difluoromethyl-2-pyridone-5-carboxylic acid were condensed according to the procedure of Example 1, subjected to dehydrative ring closure, followed by deprotection of the resulting product to give the title compound as a white solid.

$^1$HNMR (400 MHz, CD$_3$OD, δ ppm): 0.88 (3H, d, J=6.8 Hz), 4.70–4.80 (1H, m), 6.50–6.70 (2H, m), 6.80–6.90 (1H, m), 6.95–7.10 (2H, m), 7.77 (1H, t, J=59.6 Hz), 7.95–8.10 (2H, m), 8.20–8.40 (2H, m)

Example 2

Preparation of 1-ethyl-5-[(4S,5S)-4-(4-fluorophenyl)-4-(6-fluoro-3-pyridyl)-5-methyl-2-imidazolin-2yl]-3-methoxy-2-pyridone 1-ethyl-3-methoxy-2-pyridone-5-carbonitrile (30 mg) was dissolved in methanol (1 mL), and 25% sodium methoxide-methanol solution(6.6 mL) was added thereto. The mixture was stirred at room temperature for 17 hours, and methanesulfonic acid (11 μL) and a solution of (1S,2S)-1-(4-fluorophenyl)-1-(6-fluoro-3-pyridyl)-1,2-propanediamine (44.5 mg) in methanol (1 mL) were successively added. The mixture was stirred at room temperature for two days and concentrated in vacuo. The residue was dissolved in ethyl acetate, and the solution was washed with brine, and dried over anhydrous sodium sulfate. After removal of the sodium sulfate by filtration, the organic solvent was evaporated in vacuo to give a residue, which was purified by column chromatography on silica gel (chloroform:methanol=10:1) to give the title compound (1.8 mg) as a brown solid.

$^1$HNMR (400 MHz, CD$_3$OD, δ ppm): 0.83 (3.0H, brd, J=6.4 Hz), 1.36 (3.0H, t, J=7.6 Hz), 3.87 (3.0H, s), 4.07 (2.0H, q, J=7.2 Hz), 4.73 (1.0H, m), 7.01–7.09 (3.0H, m), 7.23–7.26 (2.0H, m), 7.37 (1.0H, d, J=2.0 Hz), 7.84 (1.0H, d, J=2.0 Hz), 7.97 (1.0H, m), 8.27 (1.0H, brs)

Reference Example 1

Preparation of 1-ethyl-2-pyridone-5-carboxylic Acid

Methyl 2-pyridone-5-carboxylate (1 g), bromoethane (1.46 mL) and cesium fluoride (2.98 g) were dissolved in dimethylformamide (20 mL). The solution was stirred at room temperature for three days, and then water was added. The reaction mixture was extracted with ethyl acetate, and the organic layer was washed successively with water and brine, dried over anhydrous sodium sulfate. After removal of the sodium sulfate by filtration, the organic solvent was evaporated in vacuo. The resulting residue was purified by column chromatography on silica gel (hexane:ethyl acetate= 1:1) to give a methyl ester of the title compound (465 mg) as a white solid. The methyl ester was hydrolyzed under basic conditions to give the title compound as a white solid.

$^1$HNMR (400 MHz, DMSO-d$_6$, δ ppm): 1.61 (3H, t, J=7.2 Hz), 3.98 (2H, q, J=7.2 Hz), 6.38 (1H, d, J=9.5 Hz), 7.83 (1H, dd, J=1.5 Hz, 9.5 Hz), 8.43 (1H, d, J=1.5 Hz)

Reference Example 2

Preparation of 1-difluoromethyl-2-pyridone-5-carboxylic Acid

To a solution of methyl 2-pyridone-5-carboxylate (20 g) in N-methylpyrrolidone (200 mL) was added 60% sodium hydride (5.6 g) at 0° C. After stirring for 15 minutes, lithium bromide (23 g) and sodium chlorodifluoroacetate were successively added. After stirring at 120° C. for 30 minutes, the reaction mixture was cooled to 0° C., and brine and ethyl acetate were added. The resulting mixture was filtered through a Celite pad, and the filtrate was extracted three times with ethyl acetate. The organic layer was dried over anhydrous sodium sulfate, and filtered to remove the sodium sulfate. The organic solvent was evaporated in vacuo and the residue was purified by column chromatography on silica gel (hexane:ethyl acetate=85:15) to give a methyl ester (5.09 g) of the title compound as a yellow solid. The methyl ester was hydrolysed under basic conditions to give the title compound as a white solid.

$^1$HNMR (400 MHz, DMSO-d$_6$, δ ppm): 6.56 (1H, d, J=9.6 Hz), 7.82 (1H, t, J=58.8 Hz), 7.86 (1H, dd, J=1.6 Hz, 9.6 Hz), 8.24 (1H, d, J=1.6 Hz)

Compounds of Reference Examples 2-1 to 2-11 were prepared according to the procedure of the above Reference Examples 1 and 2.

Reference Example 2-1

1-propyl-2-pyridone-5-carboxylic Acid $^1$HNMR (300 MHz, DMSO-d$_6$, δ ppm): 1.43 (3H, t, J=7.5 Hz), 1.82 (2H, sextet, J=7.5 Hz), 3.95 (2H, t, J=7.5 Hz), 6.19 (1H, d, J=9.5 Hz), 7.87 (1H, dd, J=1.6 Hz, 9.6 Hz), 8.21 (1H, d, J=1.6 Hz), 12.40 (1H, s)

Reference Example 2-2

1-isopropyl-2-pyridone-5-carboxylic Acid $^1$HNMR (300 MHz, DMSO-d$_6$, δ ppm): 1.66 (6H, d, J=4.4 Hz), 4.49 (1H, septet, J=4.4 Hz), 6.19 (1H, d, J=9.5 Hz), 7.87 (1H, dd, J=1.6 Hz, 9.5 Hz), 8.14 (1H, d, J=1.6 Hz), 12.43 (1H, brs)

Reference Example 2-3

1-(2,2-difluoroethyl)-2-pyridone-5-carboxylic Acid $^1$HNMR (300 MHz, DMSO-d$_6$, δ ppm): 4.48 (2H, dt, J=4.5 Hz, 32.0Hz), 6.32 (1H, tt, J=4.5 Hz, 84.0 Hz), 6.48 (1H, d, J=9.5 Hz), 7.82 (1H, dd, J=1.6 Hz, 9.5 Hz), 8.45 (1H, d, J=1.6 Hz), 12.97 (1H, s)

Reference Example 2-4

3-chloro-1-methyl-2-pyridone-5-carboxylic Acid $^1$HNMR (300 MHz, DMSO-d$_6$, δ ppm): 3.57 (3H, s), 7.97 (1H, s), 8.49 (1H, s), 13.04 (1H, brs)

Reference Example 2-5
3-chloro-1-ethyl-2-pyridone-5-carboxylic Acid
$^1$HNMR (300 MHz, DMSO-d$_6$, δ ppm): 1.24 (3H, t, J=7.1 Hz), 4.05 (1H, q, J=7.1 Hz), 7.98 (1H, s), 8.50 (1H, s), 13.09 (1H, brs)

Reference Example 2-6
1-ethyl-3-fluoro-2-pyridone-5-carboxylic Acid
$^1$HNMR (300 MHz, DMSO-d$_6$, δ ppm): 1.23 (3H, t, J=7.3 Hz), 4.05 (2H, q, J=7.1 Hz), 7.63 (1H, dd, J=2.3 Hz, 10.0 Hz), 8.36 (1H, s), 13.05 (1H, brs)

Reference Example 2-7
1,3-dimethyl-2-pyridone-5-carboxylic Acid
$^1$HNMR (400 MHz, CD$_3$OD, δ ppm): 2.13 (3H, s), 3.61 (3H, s), 7.81 (1H, d, J=2.0 Hz), 8.30 (1H, d, J=2.0 Hz)

Reference Example 2-8
1-ethyl-3-methyl-2-pyridone-5-carboxylic Acid
$^1$HNMR (400 MHz, CD$_3$OD, δ ppm): 1.34 (3.0H, t, J=7.2 Hz), 2.12 (3.0H, s), 4.07 (2.0H, q, J=7.2 Hz), 7.79 (1.0H, d, J=2.8 Hz), 8.29 (1.0H, d, J=2.8 Hz)

Reference Example 2-9
1-ethyl-3-methoxy-2-pyridone-5-carboxylic Acid
$^1$HNMR (400 MHz, CD$_3$OD, δ ppm): 1.34 (3H, t, J=7.2 Hz), 3.84 (3H, s), 4.09 (2H, q, J=7.2 Hz), 7.25 (1H, d, J=2.4 Hz), 8.05 (1H, d, J=2.4 Hz)

Reference Example 2-10
1-difluoromethyl-3-methyl-2-pyridone-5-carboxylic Acid
$^1$HNMR (400 MHz, CD$_3$OD, δ ppm): 2.14 (3.0H, s), 7.77 (1.0H, t, J=60 Hz), 7.83–7.84 (1.0H, m), 8.25 (1.0H, d, J=2.0 Hz)

Reference Example 2-11
1-difluoromethyl-3-ethyl-2-pyridone-5-carboxylic Acid
$^1$HNMR (400 MHz, CDCl$_3$, δ ppm): 1.23 (3.0H, t, J=7.2 Hz), 2.58 (2.0H, q, J=7.2 Hz), 7.69 (1.0H, t, J=60 Hz), 7.71–7.73 (1.0H, m), 8.30 (1.0H, d, J=2.0 Hz)

Reference Example 3
Preparation of Optically Active (2S)-1-(2-fluoro-4-pyridyl)-1-(4-trifluoromethylphenyl)-1,2-propanediamine

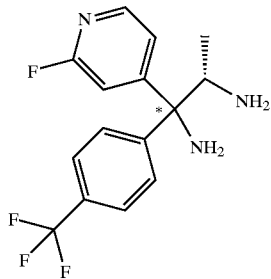

A solution of N-{(1S)-2-[methoxy(methyl)amino]-1-methyl-2-oxoethyl}carbamate (9.6 g) in tetrahydrofuran (180 mL) was dropwise added at 0° C. to a solution of 1.48M 4-trifluoromethylphenylmagnesium bromide in tetrahydrofuran (70 mL) which had been prepared in another batch. The mixture was stirred at room temperature for 14 hours, and cooled down to 0° C. After addition of aqueous sodium hydrogen sulfate, the reaction mixture was extracted with ethyl acetate. The organic layer was washed successively with water and brine, dried over anhydrous sodium sulfate, and filtered to remove the sodium sulfate. Evaporation of the organic solvent in vacuo gave t-butyl N-[(1S)-2-(4-trifluoromethylphenyl)-1-methyl-2-oxoethyl]carbamate (13.4 g) as an orange solid.

A solution of the ketone (13.4 g) obtained above, (R)-2-methyl-2-propanesulfinamide (6.14 g) and titanium tetraethoxide (19.3 g) in tetrahydrofuran (100 mL) was stirred under heating at 80° C. for 18 hours, cooled down to room temperature, and diluted with ethyl acetate. After addition of saturated aqueous sodium sulfate under vigorous stirring, the insoluble materials were filtered off through a Celite pad. The filtrate was washed successively with saturated aqueous sodium hydrogen carbonate and brine, dried over anhydrous sodium sulfate, filtered to remove the sodium sulfate, and evaporated in vacuo to remove the organic solvent. The resulting residue was purified by column chromatography on silica gel (hexane:ethyl acetate=80:20) to give t-butyl N-[(1S)-2-[(R)-(t-butylsulfinyl)imino]-2-(4-trifluoromethylphenyl)-1-methylethyl]carbamate (10.8 g) as a pale yellow solid. 1.0M trimethylaluminum-hexane solution (5.7 mL) was added to a solution of the sulfinylimine (2.0 g) in toluene (2 mL). The mixture was stirred at room temperature for 30 minutes, and was added dropwise at −100° C. to 2-fluoro-4-pyridyllithium solution which was prepared by reacting 4-fluoro-2-bromopyridine (3.18 g) with 1.55M butyllithium-hexane solution (9.21 mL) in a solvent of diethyl ether (20 mL) and tetrahydrofuran (20 mL) at −100° C. After that, the reaction temperature was raised to −78° C. over 1.5 hours, and saturated aqueous sodium sulfate was added, then the reaction temperature was raised to room temperature. The reaction mixture was dried over anhydrous magnesium sulfate, and filtered through a Celite pad. Evaporation of the organic solvent in vacuo gave a residue, which was washed with isopropyl ether to afford optically active t-butyl N-[(1s)-2-[(R)-(t-butylsulfinyl)amino]-2-(4-trifluoromethylphenyl)-2-(2-fluoro-4-pyridyl)-1-methylethyl]carbamate (2.06 g) as a white solid. The product was treated successively with trifluoroacetic acid and 4N hydrogen chloride-dioxane solution to give an optically active diamine (1.22 g) of the title compound as a pale yellow oil.

$^1$HNMR (400 MHz, CDCl$_3$, δ ppm): 1.01 (3H, d, J=6.2 Hz), 4.14 (1H, q, J=6.2 Hz), 7.20 (1H, s), 7.31 (1H, m), 7.56 (2H, d, J=8.2 Hz), 7.61 (2H, d, J=8.2 Hz), 8.11 (1H, d, J=5.6 Hz)

According to the procedure of the above Reference Example 3, diamines of Reference Examples 3-1 to 3-8 were prepared by treating N-{(1S)-2-[methoxy(methyl)amino]-1-methyl-2-oxoethyl}carbamate with an aryl metal compound, reacting the resulting ketone with (R)-2-methyl-2-propanesulfinamide, and subjecting the resulting product to diastereoselective arylation, followed by deprotection. The organometallic compounds used in the reaction, the reaction temperature and the solvents, which were employed for the preparation of ketones are given in Table 1, and those employed for the diastereoselective arylation of the imines are given in Table 2. In the Tables, THF means tetrahydrofuran and Et$_2$O means diethyl ether.

TABLE 1

| Preparation of ketones | | | |
|---|---|---|---|
| Reference Example | Metal reagents | Temperature | Solvent |
| 3-1 | 2-fluoro-4-pyridyl-magnesium chloride | −40° C.→ room temperature | THF |

TABLE 1-continued

Preparation of ketones

| Reference Example | Metal reagents | Temperature | Solvent |
|---|---|---|---|
| 3-2 | 6-trifluoromethyl-3-pyridyllithium | −100° C.→ 0° C. | THF-Et₂O |
| 3-3 | 3-bromo-4-fluorophenyl-magnesium chloride | 0° C. → room temperature | THF |
| 3-4 | 4-fluorophenyl-magnesium bromide | 0° C. → room temperature | THF |
| 3-5 | 6-difluoromethyl-3-pyridyllithium | −100° C.→ 0° C. | THF-Et₂O |
| 3-6 | 4-chlorophenyl-magnesium bromide | 0° C. → room temperature | THF |
| 3-7 | 4-trifluoromethylphenyl-magnesium bromide | 0° C. → room temperature | THF |
| 3-8 | 4-fluorophenyl-magnesium bromide | 0° C. → room temperature | THF |

TABLE 2

Diastereoselective arylation

| Reference Example | Metal reagents | Temperature | Solvent |
|---|---|---|---|
| 3-1 | 4-chlorophenyllithium | −78° C. | THF-Et₂O |
| 3-2 | 4-fluorophenyllithium | −78° C. | THF-Et₂O |
| 3-3 | 6-fluoro-3-pyridyl-lithium | −78° C. | Et₂O |
| 3-4 | 6-difluoromethyl-3-pyridyllithium | −100° C.→ −78° C. | THF-Et₂O |
| 3-5 | 4-fluorophenyl-lithium | −78° C. | THF |
| 3-6 | 6-fluoro-3-pyridyl-lithium | −100° C.→ −78° C. | THF-Et₂O-toluene |
| 3-7 | 6-fluoro-3-pyridyl-lithium | −78° C. | THF-Et₂O-toluene |
| 3-8 | 6-cyclopropyl-3-pyridyllithium | −78° C.→ −40° C. | Et₂O |

Reference Example 3-1

Optically Active (2S)-1-(2-fluoro-4-pyridyl)-1-(4-chlorophenyl)-1,2-propanediamine

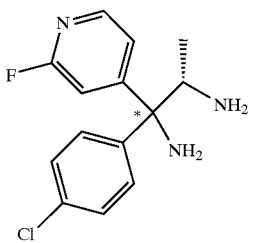

¹HNMR (400 MHz, CDCl₃, δ ppm): 1.00 (3H, d, J=6.0 Hz), 4.00 (1H, q, J=6.0 Hz), 7.09 (1H, s), 7.23 (1H, m), 7.30 (2H, d, J=8.8 Hz), 7.45 (2H, d, J=8.8 Hz), 8.08 (1H, d, J=5.6 Hz)

Reference Example 3-2

Optically Active (2S)-1-(4-fluorophenyl)-1-(6-trifluoromethyl-3-pyridyl)-1,2-propanediamine

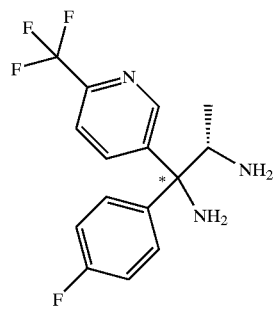

¹HNMR (300 MHz, CDCl₃, δ ppm): 1.01 (3H, d, J=6.3 Hz), 4.14 (1H, q, J=6.3 Hz), 7.03 (2H, m), 7.51 (2H, m), 7.60 (1H, d, J=8.3 Hz), 8.00 (1H, dd, J=2.2 Hz, 8.3 Hz), 8.85 (1H, d, J=2.2 Hz) $[\alpha]_D^{25}$ (c 1.00, ethanol) −16.38°

Reference Example 3-3

(1S,2S)-1-(6-fluoro-3-pyridyl)-1-(3-bromo-4-fluorophenyl)-1,2-propanediamine

¹HNMR (400 MHz, CDCl₃, δ ppm): 1.00 (3H, d, J=6.3 Hz), 4.05 (1H, q, J=6.3 Hz), 6.87 (1H, dd, J=2.7 Hz, 8.4 Hz), 7.08 (1H, m), 7.35 (1H, m), 7.70 (1H, m), 7.96 (1H, m), 8.39 (1H, d, J=2.7 Hz)

Reference Example 3-4

Optically Active (2S)-1-(4-fluorophenyl)-1-(6-difluoromethyl-3-pyridyl)-1,2-propanediamine

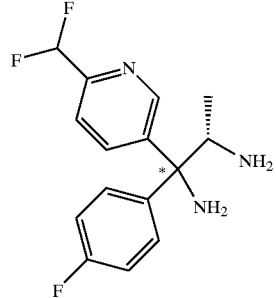

¹HNMR (300 MHz, CDCl₃, δ ppm): 1.04 (3H, d, J=6.3 Hz), 4.14 (1H, q, J=6.3 Hz), 6.60 (1H, t, J=55.5 Hz), 7.00–7.04 (2H, m), 7.26–7.46 (2H, m), 7.56 (1H, d, J=8.4 Hz), 8.03 (1H, dd, J=2.0 Hz, 8.3 Hz), 8.82(1H, s)

Reference Example 3-5

Optically Active (2S)-1-(4-fluorophenyl)-1-(6-difluoromethyl-3-pyridyl)-1,2-propanediamine (Epimer at Position 1 of the Compound of Reference Example 3-4)

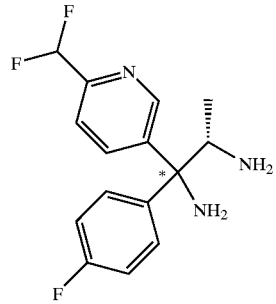

¹HNMR (300 MHz, CDCl₃, δ ppm): 1.01 (3H, d, J=6.3 Hz), 4.12 (1H, q, J=6.6 Hz), 6.60 (1H, t, J=55.2 Hz), 6.99–7.04 (2H, m), 7.49–7.57 (3H, m), 7.96 (1H, dd, J=1.8 Hz, 8.3 Hz), 8.77 (1H, s)

Reference Example 3-6
Optically Active (2S)-1-(4-chlorophenyl)-1-(6-fluoro-3-pyridyl)-1,2-propanediamine

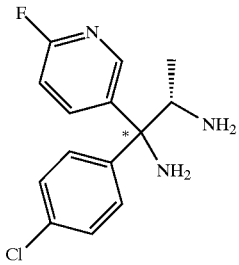

$^1$HNMR (400 MHz, CDCl$_3$, δ ppm): 0.99 (3H, d, J=6.0 Hz), 4.04 (1H, q, J=6.4 Hz), 6.83 (1H, dd, J=2.8 Hz, 8.4 Hz), 7.26 (2H, d, J=8.8 Hz), 7.37 (2H, d, J=8.4 Hz), 7.91–7.96 (1H, m), 8.37 (1H, d, J=2.4 Hz)

Reference Example 3-7
Optically Active (2S)-1-(6-fluoro-3-pyridyl)-1-(4-trifluoromethlphenyl)-1,2-propanediamine

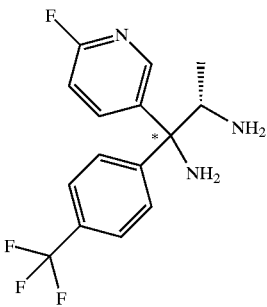

$^1$HNMR (400 MHz, CDCl$_3$, δ ppm): 0.99 (3H, d, J=6.4 Hz), 4.11 (1H, q, J=6.4 Hz), 6.84 (1H, dd, J=2.8 Hz, 8.4 Hz), 7.54 (2H, d, J=9.2 Hz), 7.57 (2H, d, J=9.2 Hz), 7.94–7.98 (1H, m), 8.40 (1H, d, J=2.8 Hz)

Reference Example 3-8
Optically Active (2S)-1-(6-cyclopropyl-3-pyridyl)-1-(4-fluorophenyl)-1,2-propanediamine

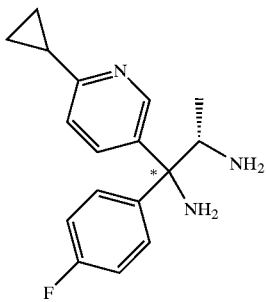

$^1$HNMR (300 MHz, CDCl$_3$, δ ppm): 0.88–1.04 (7H, m), 1.60–1.92 (4H, br), 1.93–2.02 (1H, m), 4.01 (1H, q, J=6.3 Hz), 6.92–7.08 (3H, m), 7.41 (2H, dd, J=8.8 Hz, 5.4 Hz), 7.67 (1H, dd, J=8.2 Hz, 2.6 Hz), 8.57 (1H, d, J=2.5 Hz)

Reference Example 4
1-ethyl-3-methoxy-2-pyridone-5-carbonitrile

To a solution of 1-ethyl-3-methoxy-2-pyridone-5-carboxylic acid (245 mg) of Reference Example 2-9 in chloroform (3 mL) was added 1,1'-carbonyldiimidazole (263 mg), and the mixture was stirred at room temperature for 30 minutes. After addition of 30% aqueous ammonia (6 mL), the mixture was stirred at room temperature for one hour, and extracted with a mixed solution of chloroform and methanol (5:1). The organic layer was washed successively with water and brine, dried over anhydrous sodium sulfate, and filtered to remove the sodium sulfate. The organic solvent was evaporated in vacuo to give an amide (232 mg) as a brown solid. A solution of the above amide (210 mg) in chloroform (3 mL) was cooled to −78° C., and triethylamine (1.49 mL) and trifluoroacetic anhydride (3.21 mL) were successively added thereto. The reaction temperature was raised to −30° C. over a period of 1.5 hours, and the reaction mixture was diluted with chloroform. After addition of saturated aqueous sodium hydrogen carbonate, the reaction mixture was extracted with chloroform. The organic layer was dried over anhydrous sodium sulfate, filtered to remove the sodium sulfate, and the organic solvent was evaporated in vacuo to give a residue. The residue was purified by column chromatography on silica gel (hexane:ethyl acetate= 10:0 to 4:6) to give the title compound (80 mg) as a white solid.

$^1$HNMR (400 MHz, CDCl$_3$, δ ppm): 1.38 (3H, t, J=7.2 Hz), 3.84 (3H, s), 4.04 (2H, q, J=7.2 Hz), 6.59 (1H, d, J=2.2 Hz), 7.44 (1H, s, J=2.2 Hz)

Reference Example 5
Preparation of 1-methoxy-2-pyridone-5-carboxylic Acid
(1) Preparation of Methyl 6-chloronicotinate N-oxide 2-chloro-5-methoxycarbonylpyridine (7.0 g) and urea-hydrogen peroxide adduct (6.93 g) were suspended in acetonitrile (100 mL), and trifluoroacetic anhydride (9.92 mL) was dropwise added thereto at 0° C. The reaction mixture was stirred at room temperature for 5 hours, and evaporated in vacuo to remove the solvent. After addition of saturated aqueous sodium hydrogen carbonate and aqueous sodium thiosulfate to the residue, the mixture was extracted 5 times with ethyl acetate. The organic layer was dried over anhydrous sodium sulfate, and filtered to remove the sodium sulfate. The organic solvent was evaporated in vacuo and the resulting residue was purified by column chromatography on silica gel (hexane:ethyl acetate=2:8) to give the title compound as a pale brown solid (8.0 g).

$^1$HNMR (400 MHz, CD$_3$OD, δ ppm): 3.96 (3H, s), 7.86 (1H, d, J=8.8 Hz), 7.95 (1H, dd, J=1.6 Hz, 8.4 Hz), 8.88 (1H, d, J=2.0 Hz)

(2) Preparation of Methyl 1-hydroxy-2-pyridone-5-carboxylate

Trifluoroacetic anhydride (30 mL) was dropwise added to a solution of 2-chloro-5-methoxycarbonylpyridine-N-oxide (12.2 g) in dry acetonitrile (200 mL) at 0° C., and the mixture was stirred at room temperature for one hour. The solvent was evaporated in vacuo, and methanol was portionwise added to the residue at 0° C. The mixture was stirred at room temperature for 15 minutes, and the solvent was evaporated in vacuo to give a residue. The residue was dried under a vacuum to give a solid. The solid was purified by recrystallization (acetonitrile-diethyl ether) to give the title compound (9.3 g) as a white solid.

$^1$HNMR (400 MHz, CD$_3$OD, δ ppm): 3.83 (3H, s), 6.52 (1H, d, J=9.2 Hz), 7.80 (1H, dd, J=2.4 Hz, 9.2 Hz), 8.51 (1H, d, J=2.4 Hz)

(3) Preparation of 1-methoxy-2-pyridone-5-carboxylic Acid

To a solution of 1-hydroxy-2-pyridone-5-carboxylic acid (1.69 g) and methyl iodide (4.26 g) in dimethylformamide (20 mL) was added sodium hydrogen carbonate (3.36 g), and the mixture was stirred at room temperature overnight. After removal of the solvent by evaporation in vacuo, ethyl acetate and distilled water were added to the residue. The mixture was extracted three times with ethyl acetate, and the organic layer was dried over anhydrous sodium sulfate, filtered to remove the sodium sulfate, and the organic solvent was evaporated in vacuo. The resulting residue was dried in vacuo to give the objective product as a pale yellow oil (2.20 g). The resulting methyl ester was hydrolyzed under a basic condition to give the title compound as a white solid (1.22 g).

$^1$HNMR (400 MHz, CD$_3$OD, δ ppm): 4.07 (3H, s), 6.63 (1H, d, J=9.6 Hz), 7.94 (1H, dd, J=2.4 Hz, 9.6 Hz), 8.58 (1H, d, J=2.4 Hz)

Compounds of Reference Examples 5-1 and 5-2 were synthesized according to the procedure of the above Reference Example 5.

Reference Example 5-1

1-ethoxy-2-pyridone-5-carboxylic Acid $^1$HNMR (400 MHz, CD$_3$OD, δ ppm): 1.38 (3.0H, t, J=7.2 Hz), 4.31 (2.0H, q, J=7.2 Hz), 6.63 (1.0H, d, J=9.6 Hz), 7.93 (1.0H, dd, J=2.4 Hz, 9.6 Hz), 8.55 (1.0H, d, J=2.0 Hz)

Reference Example 5-2

1-difluoromethoxy-2-pyridone-5-carboxylic Acid $^1$HNMR (400 MHz, CD$_3$OD, δ ppm): 6.71 (1.0H, d, J=10.0 Hz), 7.07 (1.0H, t, J=7.0 Hz), 7.97 (1.0H, dd, J=2.4 Hz, 9.6 Hz), 8.50 (1.0H, d, J=2.4 Hz)

Reference Example 6

Preparation of 1-cyclopropyl-2-pyridone-5-carboxylic Acid

Methyl coumalate (1.52 g) was dissolved in methanol (4 mL), and cyclopropylamine (1.5 ml) was added thereto at room temperature. The mixture was stirred for 2 hours and the solvent was evaporated in vacuo to give a residue. Water was added to the residue, and the mixture was extracted with ethyl acetate. The organic layer was washed with brine, and dried over anhydrous magnesium sulfate. After removal of the magnesium sulfate by filtration, the organic solvent was removed by evaporation in vacuo. The resulting solid was triturated with isopropyl ether and filtered to give a methyl ester (471 mg) of the title compound as a white solid. The methyl ester was hydrolyzed under a basic condition to give the title compound as a yellow solid.

$^1$HNMR (400 MHz, CD$_3$OD, δ ppm): 0.91–0.97 (2H, m), 1.12–1.19 (2H, m), 3.34 (1H, m), 6.50 (1H, d, J=9.9 Hz), 7.92 (1H, dd, J=9.5 Hz, 2.6 Hz), 8.29 (1H, d, J=2.6 Hz)

Formulation Example 1

20.0 g of the compound of Example 1, 417 g of lactose, 80 g of crystalline cellulose and 80 g of partial alpha-starch are blended with a V-cone blender. To the mixture is added 3.0 g of magnesium stearate, and the whole is blended. The blended powder is compressed into 3000 tablets by conventional procedure so that each tablet has a weight of 150 mg and a diameter of 7.0 mm.

| The content per one tablet (150 mg) | |
|---|---|
| The compound of Example 1 | 5.0 mg |
| Lactose | 104.25 mg |
| Crystalline cellulose | 20.0 mg |
| Partial alpha-starch | 20.0 mg |
| Magnesium stearate | 0.75 mg |

Formulation Example 2

10.8 g of hydroxypropylcellulose 2910 and 2.1 g of polyethylene glycol 6000 are dissolved in 172.5 g of purified water. To the solution is dispersed 2.1 g of titanium dioxide to provide a coating liquid. 2,500 tablets separately prepared according to Formulation Example 1 are subjected to spray-coating with the coating liquid using HICOATER-MINI to provide film coated tablets with a weight of 155 mg.

| The content per one tablet (155 mg) | |
|---|---|
| The tablet prepared in Formulation Example 1 | 150 mg |
| Hydroxypropylcellulose 2910 | 3.6 mg |
| Polyethylene glycol 6000 | 0.7 mg |
| Titanium dioxide | 0.7 mg |

INDUSTRIAL APPLICABILITY

Compounds of the present invention (I) have NPY antagonistic actions especially on NPY Y5 receptors, show excellent pharmacokinetics such as transport into brain or transport to cerebrospinal fluid, etc., and are very safe. Thus, the compound of the present invention (I) are useful as agents for the treatment of various diseases related to NPY, for example, cardiovascular disorders such as angina, acute or congestive heart failure, myocardial infarction, hypertension, nephropathy, electrolyte abnormality, vasospasm, arteriosclerosis, etc., central nervous system disorders such as bulimia, depression, anxiety, seizure, epilepsy, dementia, pain, alcoholism, drug withdrawal, circadian rhythm disorders, schizophrenia, memory impairment, sleep disorders, cognitive impairment, etc., metabolic diseases such as obesity, diabetes, hormone abnormality, hypercholesterolemia, hyperlipidemia, gout, fatty liver, etc., genital or reproductive disorders such as infertility, preterm labor, sexual dysfunction, etc., gastro-intestinal disorders, respiratory disorders, inflammatory diseases or glaucoma, and the like, also for example, atherosclerosis, hypogonadism, hyperandrogenism, polycystic ovary syndrome, hirsutism, gastro-intestinal motility disorder, obesity-related gastro-esophageal reflux, obesity hypoventilation (Pickwickian syndrome), sleep apnea, inflammation, systemic inflammation of the vasculature, osteoarthritis, insulin resistance, bronchoconstriction, alcohol preference, metabolic syndrome, Alzheimer's disease, cardiac hypertrophy, left ventricular hypertrophy, hypertriglyceridemia, low HDL cholesterol, cardiovascular disorders such as coronary heart disease (CHD), cerebrovascular disease, stroke, peripheral vascular disease, sudden death, etc., gallbladder diseases, cancer (breast, endometrial, colon), breathlessness, hyperuricemia, impaired fertility, low back pain, or increased anesthetic risk, and the like.

What is claimed is:

1. A compound of the formula (I):

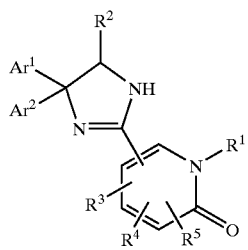

(wherein Ar$^1$ and Ar$^2$ are independently aryl or heteroaryl, any of which is optionally substituted by a substituent selected from the group consisting of cyano, halogen, nitro, lower alkyl, halo-lower alkyl, hydroxy-lower alkyl, cyclo-lower alkyl, cyclo(lower alkyl)-lower alkyl, lower alkenyl, lower alkylamino, di-lower alkylamino, lower alkanoylamino, lower alkylsulfonylamino, arylsulfonylamino, hydroxy, lower alkoxy, halo-lower alkoxy, aryloxy, heteroaryloxy, lower alkylthio, carboxyl, formyl, lower alkanoyl, lower alkoxycarbonyl, carbamoyl, lower alkylcarbamoyl, di-lower alkylcarbamoyl, lower alkylsulfonyl, arylsulfonyl, aryl and heteroaryl;

R$^1$ and R$^2$ are independently lower alkyl, cyclo-lower alkyl, cyclo(lower alkyl)-lower alkyl or lower alkoxy, any of which is optionally substituted by a substituent selected from the group consisting of halogen, lower alkylamino, di-lower alkylamino, lower alkanoylamino, hydroxy, lower alkoxy, formyl, lower alkoxycarbonyl, lower alkylcarbamoyl and di-lower alkylcarbamoyl;

R$^3$, R$^4$ and R$^5$ are independently hydrogen, cyano, halogen or hydroxy, or lower alkyl, lower alkoxy or lower alkylthio, the last three groups being optionally substituted by a substituent selected from the group consisting of halogen, lower alkylamino, di-lower alkylamino, lower alkanoylamino, hydroxy, lower alkoxy, formyl, lower alkoxycarbonyl, lower alkylcarbamoyl and di-lower alkylcarbamoyl), or a salt or ester thereof.

2. The compound, or a salt or ester thereof, as claimed in claim 1, wherein both R$^4$ and R$^5$ are hydrogen.

3. The compound of the formula (I-1), or a salt or ester thereof, as claimed in claim 1:

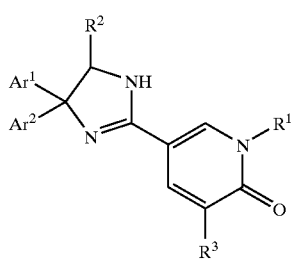

wherein Ar$^1$ and Ar$^2$ are independently aryl or heteroaryl, any of which is optionally substituted by a substituent selected from the group consisting of cyano, halogen, nitro, lower alkyl, halo-lower alkyl, hydroxy-lower alkyl, cyclo-lower alkyl, cyclo(lower alkyl)-lower alkyl, lower alkenyl, lower alkylamino, di-lower alkylamino, lower alkanoylamino, lower alkylsulfonylamino, arylsulfonylamino, hydroxy, lower alkoxy, halo-lower alkoxy, aryloxy, heteroaryloxy, lower alkylthio, carboxyl, formyl, lower alkanoyl, lower alkoxycarbonyl, carbamoyl, lower alkylcarbamoyl, di-lower alkylcarbamoyl, lower alkylsulfonyl, arylsulfonyl, aryl and heteroaryl;

R$^1$ and R$^2$ are independently lower alkyl, cyclo-lower alkyl, cyclo(lower alkyl)-lower alkyl or lower alkoxy, any of which is optionally substituted by a substituent selected from the group consisting of halogen, lower alkylamino, di-lower alkylamino, lower alkanoylamino, hydroxy, lower alkoxy, formyl, lower alkoxycarbonyl, lower alkylcarbamoyl and di-lower alkylcarbamoyl;

R$^3$ is hydrogen, cyano, halogen or hydroxy, or lower alkyl, lower alkoxy or lower alkylthio, the last three groups being optionally substituted by a substituent selected from the group consisting of halogen, lower alkylamino, di-lower alkylamino, lower alkanoylamino, hydroxy, lower alkoxy, formyl, lower alkoxycarbonyl, lower alkylcarbamoyl and di-lower alkylcarbamoyl.

4. The compound, or a salt thereof, as claimed in claim 1, wherein one of Ar$^1$ and Ar$^2$ is aryl which is substituted by a substituent selected from the group consisting of halogen and halo-lower alkyl, and one of the remainder is heteroaryl which is substituted by a substituent selected from the group consisting of halogen and halo-lower alkyl.

5. The compound, or a salt or ester thereof, as claimed in claim 1, wherein R$^1$ is lower alkyl, cyclo-lower alkyl or lower alkoxy, any of which is optionally substituted by a substituent selected from the group consisting of halogen, lower alkylamino, di-lower alkylamino, lower alkanoylamino, hydroxy, lower alkoxy, formyl, lower alkoxycarbonyl, lower alkylcarbamoyl and di-lower alkylcarbamoyl.

6. The compound, or a salt or ester thereof, as claimed in claim 1, wherein R$^2$ is lower alkyl which is optionally substituted by a substituent selected from the group consisting of halogen, lower alkylamino, di-lower alkylamino, lower alkanoylamino, hydroxy, lower alkoxy, formyl, lower alkoxycarbonyl, lower alkylcarbamoyl and di-lower alkylcarbamoyl.

7. The compound, or a salt or ester thereof, as claimed in claim 2, wherein R$^3$ is hydrogen, halogen or hydroxy, or lower alkyl which is optionally substituted by a substituent selected from the group consisting of halogen, lower alkylamino, di-lower alkylamino, lower alkanoylamino, hydroxy, lower alkoxy, formyl, lower alkoxycarbonyl, lower alkylcarbamoyl and di-lower alkylcarbamoyl.

8. The compound, or a salt thereof, as claimed in claim 2, wherein one of Ar$^1$ and Ar$^2$ is aryl which is substituted by a substituent selected from the group consisting of halogen and halo-lower alkyl, and one of the remainder is heteroaryl which is substituted by a substituent selected from the group consisting of halogen and halo-lower alkyl;

R$^1$ is lower alkyl, cyclo-lower alkyl or lower alkoxy, any of which is optionally substituted by a substituent selected from the group consisting of halogen, lower alkylamino, di-lower alkylamino, lower alkanoylamino, hydroxy, lower alkoxy, formyl, lower alkoxycarbonyl, lower alkylcarbamoyl and di-lower alkylcarbamoyl;

R$^2$ is lower alkyl which is optionally substituted by a substituent selected from the group consisting of halogen, lower alkylamino, di-lower alkylamino, lower alkanoylamino, hydroxy, lower alkoxy, formyl, alkoxycarbonyl, lower alkylcarbamoyl and di-lower alkylcarbamoyl; and R³ is hydrogen, halogen or hydroxy, or lower alkyl which is optionally substituted by a substituent selected from the group consisting of halogen, lower alkylamino, di-lower alkylamino, lower alkanoylamino, hydroxy, lower alkoxy, formyl, lower alkoxycarbonyl, lower alkylcarbamoyl and di-lower alkylcarbamoyl.

9. The compound, or a salt thereof, as claimed in claim 1, wherein the compound is selected from the group consisting of 5-[(4S,5S)-4-(4-fluorophenyl)-4-(6-fluoro-3-pyridyl)-5-methyl-2-imidazolin-2yl]-1-methyl-2-pyridone, 1-difluoromethyl-5-[(4S,5S)-4-(4-fluorophenyl)-4-(6-fluoro-3-pyridyl)-5-methyl-2-imidazolin-2-yl]-pyridone, 1-ethyl-5-[(4S,5S)-4-(4-fluorophenyl)-4-(6-fluoro-3-pyridyl)-5-methyl-2-2-imidazolin-2-yl]-pyridone, 1-difluoromethyl-5-[(4R,5S)-4-(4-fluorophenyl)-4-(2-fluoro-4-pyridyl)-5-methyl-2-imidazolin-2-yl]-pyridone, 1-(2,2-difluoroethyl)-5-[(4S,5S)-4-(4-fluorophenyl)-4-(6-fluoro-3-pyridyl)-5-methyl-2-imidazolin-2-yl]-2-pyridone, 5-[(4S,5S)-4-(4-fluorophenyl)-4-(6-fluoro-3-pyridyl)-5-methyl-2-imidazolin-2yl]-1-propyl-2-pyridone, 5-[(4S,5S)-4-(4-fluorophenyl)-4-(6-fluoro-3-pyridyl)-5-methyl-2-imidazolin-2-yl]-2-pyridone, 1-difluoromethyl-5-[(4R,5S)-4-(4-fluorophenyl)-5-methyl-4-(6-trifluoromethyl-3-pyridyl)-2-imidazolin-2-yl]-2-pyridone, 1-difluoromethyl-5-[(4S,5S)-4-(4-fluorophenyl)-5-methyl-4-(6-trifluoromethyl-3-pyridyl)-2-imidazolin-2-yl]-2-pyridone, 1-ethyl-5-[(4R,5S)-4-(4-fluorophenyl)-5-methyl-4-(6-trifluoromethyl-3-pyridyl)-2-imidazolin-2-yl]-2-pyridone, 1-ethyl-5-[(4S,5S)-4-(4-fluorophenyl)-5-methyl-4-(6-trifluoromethyl-3-pyridyl)-2-imidazolin-2-yl]-2-pyridone, 5-[(4R,5S)-4-(4-fluorophenyl)-5-methyl-4-(6-trifluoromethyl-3-pyridyl)-2-imidazolin-2-yl]-1-propyl-2-pyridone, 5-[(4S,5S)-4-(4-fluorophenyl)-5-methyl-4-(6-trifluoromethyl-3-pyridyl)-2-imidazolin-2-yl]-1-propyl-2-pyridone, 1-(2,2-difluoroethyl)-5-[(4R,5S)-4-(4-fluorophenyl)-5-methyl-4-(6-trifluoromethyl-3-pyridyl)-2-imidazolin-2-yl]-2-pyridone, 1-(2,2-difluoroethyl)-5-[(4S,5S)-4-(4-fluorophenyl)-5-methyl-4-(6-trifluoromethyl-3-pyridyl)-2-imidazolin-2-yl]-2-pyridone, 3-chloro-1-ethyl-5-[(4R,5S)-4-(4-fluorophenyl)-5-methyl-4-(6-trifluoromethyl-3-pyridyl)-2-imidazolin-2-yl]-2-pyridone, 3-chloro-1-ethyl-5-[(4S,5S)-4-(4-fluorophenyl)-5-methyl-4-(6-trifluoromethyl-3-pyridyl)-2-imidazolin-2-yl]-2-pyridone, 5-[(4S,5S)-4-(3-bromo-4-fluorophenyl)-4-(6-fluoro-3-pyridyl)-5-methyl-2-imidazolin-2-yl]-1-difluoromethyl-2-pyridone, 1-difluoromethyl-5-[(4S,5S)-4-(4-fluorophenyl)-4-(2-fluoro-4-pyridyl)-5-methyl-2-imidazolin-2-yl]-2-pyridone, 1-ethyl-5-[(4S,5S)-4-(4-fluorophenyl)-4-(2-fluoro-4-pyridyl)-5-methyl-2-imidazolin-2-yl]-2-pyridone, 1-(2,2-difluoroethyl)-5-[(4S,5S)-4-(4-fluorophenyl)-4-(2-fluoro-4-pyridyl)-5-2-imidazolin-2-yl]-2-pyridone, 1-difluoromethyl-5-[(4R,5S)-4-(2-fluoro-4-pyridyl)-5-methyl-4-(4-trifluorophenyl)-2-imidazolin-2-yl]-2-pyridone, 1-difluoromethyl-5-[(4S,5S)-4-(2-fluoro-4-pyridyl)-5-methyl-4-(4-trifluoropheny)-2-imidazolin-2-yl]-2-pyridone, 1-ethyl-5-[(4R,5S)-4-(4-fluorophenyl)-4-(2-fluoro-4-pyridyl)-5-methyl-2-imidazolin-2-yl]-2-pyridone, 3-chloro-1-ethyl-5-[(4S,5S)-4-(4-fluorophenyl)-4-(6-fluoro-3-pyridyl)-5-methyl-2-imidazolin-2-yl]-2-pyridone, 5-[(4R,5S)-4-(4-fluorophenyl)-5-methyl-4-(6-trifluoromethyl-3-pyridyl)-2-imidazolin-2-yl]-1-methyl-2-pyridone, 5-[(4S,5S)-4-(4-fluorophenyl)-5-methyl-4-(6-trifluoromethyl-3-pyridyl)-2-imidazolin-2-yl]-1-methyl-2-pyridone, 1-difluoromethyl-5-[(4R,5S)-4-(4-fluorophenyl)-4-(6-fluoro-3-pyridyl)-5-methyl-2-imidazolin-2-yl]-2-pyridone, 1-difluoromethyl-5-[(4R,5S)-4-(4-chlorophenyl)-4-(2-fluoro-4-pyridyl)-5-methyl-2-imidazolin-2-yl]-2-pyridone, 1-difluoromethyl-5-[(4S,5S)-4-(4-chlorophenyl)-4-(2-fluoro-4-pyridyl)-5-methyl-2-imidazolin-2-yl]-2-pyridone, 1-ethyl-5-[(4R,5S)-4-(2-fluoro-4-pyridyl)-5-methyl-4-(4-trifluoromethylphenyl)-2-imidazolin-2-yl]-2-pyridone, 1-ethyl-5-[(4S,5S)-4-(2-fluoro-4-pyridyl)-5-methyl-4-(4-trifluoromethylphenyl)-2-imidazolin-2-yl]-2-pyridone, 1-ethyl-5-[(4R,5S)-4-(4-chlorophenyl)-4-(2-fluoro-4-pyridyl)-5-methyl-2-imidazolin-2-yl]-2-pyridone, 1-ethyl-5-[(4S,5S)-4-(4-chlorophenyl)-4-(2-fluoro-4-pyridyl)-5-methyl-2-imidazolin-2-yl]-2-pyridone, 3-chloro-1-ethyl-5-[(4R,5S)-4-(4-fluorophenyl)-4-(2-fluoro-4-pyridyl)-5-methyl-2-imidazolin-2-yl]-2-pyridone, 1-ethyl-3-fluoro-5-[(4S,5S)-4-(4-fluorophenyl)-4-(6-fluoro-3-pyridyl)-5-methyl-2-imidazolin-2-yl]-2-pyridone, 3-chloro-5-[(4S,5S)-4-(4-fluorophenyl)-4-(6-fluoro-3-pyridyl)-5-methyl-2-imidazolin-2-yl]-1-methyl-2-pyridone, 1-ethyl-5-[(4S,5S)-4-(4-fluorophenyl)-4-(6-fluoro-3-pyridyl)-5-methyl-2-imidazolin-2-yl]-3-methyl-2-pyridone, 3-chloro-5-[(4R,5S)-4-(4-fluorophenyl)-5-methyl-4-(6-trifluoromethyl-3-pyridyl)-2-imidazolin-2-yl]-1-methyl-2-pyridone, 3-chloro-5-[(4S,5S)-4-(4-fluorophenyl)-5-methyl-4-(6-trifluoromethyl-3-pyridyy-2-imidazolin-2-yl]-1-methyl-2-pyridone, 1-ethyl-3-fluoro-5-[(4R,5S)-4-(4-fluorophenyl)-5-methyl-4-(6-trifluoromethyl-3-pyridyl)-2-imidazolin-2-yl]-1-methyl-2-pyridone, 1-ethyl-3-fluoro-5-[(4S,5S)-4-(4-fluorophenyl)-5-methyl-4-(6- -trifluoromethyl-3-pyridyl)-2-imidazolin-2-yl]-2-pyridone, 1-ethyl-5-[(4R,5S)-4-(4-fluorophenyl)-4-(6-fluoro-3-pyridyl)-5-methyl-2-2-imidazolin-2-yl]-2-pyridone, 1-(2,2-difluoroethyl)-5-[(4R,5S)-4-(4-fluorophenyl)-4-(6-fluoro-3-pyridyl)-5-methyl-2-imidazolin-2-yl]-2-pyridone, 5-[(4S,5S)-4-(4-fluorophenyl)-4-(6-fluoro-3-pyridyl)-5-methyl-2-imidazolin-2-yl]-1,3-dimethyl-2-pyridone,
3-chloro-5-[(4R,5S)-4-(4-fluorophenyl)-4-(6-fluoro-3-pyridyl)-5-methyl-2-imidazolin-2-yl]-1-methyl-2-pyridone,
3-chloro-1-ethyl-5-[(4R,5S)-4-(4-fluorophenyl)-4-(6-fluoro-3-pyridyl)-5-methyl-2-imidazolin-2-yl]-2-pyridone,
1-ethyl-3-fluoro-5-[(4R,5S)-4-(4-fluorophenyl)-4-(6-fluoro-3-pyridyl)-5-methyl-2-imidazolin-2-yl]-2-pyridone,
1-difluoromethyl-5-[(4R,5S)-4-(6-difluoromethyl-3-pyridyl)-4-(4-fluorophenyl)-5-methyl-2-imidazolin-2-yl]-2-pyridone,
1-difluoromethyl-5-[(4S,5S)-4-(6-difluoromethyl-3-pyridyl)-4-(4-fluorophenyl)-5-methyl-2-imidazolin-2-yl]-2-pyridone,
5-[(4R,5S)-4-(4-fluorophenyl)-4-(6-fluoro-3-pyridyl)-5-methyl-2-imidazolin-2-yl]-1-2-pyridone,
1-ethyl-3-fluoro-5-[(4R,5S)-4-(4-chlorophenyl)-4-(2-fluoro-4-pyridyl)-5-methyl-2-imidazolin-2-yl]-2-pyridone,
1-ethyl-3-fluoro-5-[(4S,5S)-4-(4-chlorophenyl)-4-(2-fluoro-4-pyridyl)-5-methyl-2-imidazolin-2-yl]-2-pyridone,
3-ethyl-5-[(4S,5S)-4-(4-fluorophenyl)-4-(6-fluoro-3-pyridyl)-5-methyl-2-imidazolin-2-yl]-1-methyl-2-pyridone,
3-ethyl-5-[(4R,5S)-4-(4-fluorophenyl)-4-(2-fluoro-4-pyridyl)-5-methyl-2-imidazolin-2-yl]-1-methyl-2-pyridone,
3-ethyl-5-[(4R,5S)-4-(4-fluorophenyl)-4-(6-fluoro-3-pyridyl)-5-methyl-2-imidazolin-2-yl]-1-methyl-2-pyridone,
1-ethyl-5-[(4S,5S)-4-(4-fluorophenyl)-4-(6-fluoro-3-pyridyl)-5-methyl-2-imidazolin-2-yl]-3-methoxy-2-pyridone,
1-difluoromethyl-5-[(4R,5S)-4-(6-difluoromethyl-3-pyridyl)-4-(4-fluorophenyl)-5-methyl-2-imidazolin-2-yl]-2-pyridone,
1-difluoromethyl-5-[(4S,5S)-4-(6-difluoromethyl-3-pyridyl)-4-(4-fluorophenyl)-5-methyl-2-imidazolin-2-yl]-2-pyridone,
5-[(4R,5S)-4-(6-difluoromethyl-3-pyridyl)-4-(4-fluorophenyl)-5-methyl-2-imidazolin-2-yl]-1-ethyl-2-pyridone,
5-[(4S,5S)-4-(6-difluoromethyl-3-pyridyl)-4-(4-fluorophenyl)-5-methyl-2-imidazolin-2-yl]-1-ethyl-2-pyridone,
5-[(4R,5S)-4-(6-difluoromethyl-3-pyridyl)-4-(4-fluorophenyl)-5-methyl-2-imidazolin-2-yl]-1-ethyl-3-fluoro-2-pyridone,
5-[(4S,5S)-4-(6-difluoromethyl-3-pyridyl)-4-(4-fluorophenyl)-5-methyl-2-imidazolin-2-yl]-1-ethyl-3-fluoro-2-pyridone,
5-[(4S,5S)-4-(4-fluorophenyl)-4-(6-fluoro-3-pyridyl)-5-methyl-2-imidazolin-2-yl]-1-methoxy-2-pyridone,
5-[(4R,5S)-4-(4-fluorophenyl)-4-(6-fluoro-3-pyridyl)-5-methyl-2-imidazolin-2-yl]-1-methoxy-2-pyridone,
1-ethoxy-5-[(4R,5S)-4-(4-fluorophenyl)-4-(6-fluoro-3-pyridyl)-5-methyl-2-imidazolin-2-yl]-2-pyridone,
1-cyclopropyl-5-[(4S,5S)-4-(4-fluorophenyl)-4-(6-fluoro-3-pyridyl)-5-methyl-2-imidazolin-2-yl]-2-pyridone,
1-cyclopropyl-5-[(4R,5S)-4-(4-fluorophenyl)-5-methyl-4-(6-trifluoromethyl-3-pyridyl)-2-imidazolin-2-yl]-2-pyridone,
5-[(4S,5S)-4-(4-fluorophenyl)-4-(2-fluoro-4-pyridyl)-5-methyl-2-imidazolin-2-yl]-1-methoxy-2-pyridone,
5-[(4R,5S)-4-(4-fluorophenyl)-5-methyl-4-(6-trifluoromethyl-3-pyridyl)-2-imidazolin-2-yl]-1-methoxy-2-pyridone,
5-[(4R,5S)-4-(4-chlorophenyl)-4-(2-fluoro-4-pyridyl)-5-methyl-2-imidazolin-2-yl]-1-methoxy-2-pyridone,
1-difluoromethyl-5-[(4S,5S)-4-(4-fluorophenyl)-4-(6-fluoro-3-pyridyl)-5-methyl-2-imidazolin-2-yl]-3-methyl-2-pyridone,
1-difluoromethyl-5-[(4R,5S)-4-(4-fluorophenyl)-4-(6-fluoro-3-pyridyl)-5-methyl-2-imidazolin-2-yl]-3-methyl-2-pyridone,
1-difluoromethyl-5-[(4S,5S)-4-(4-fluorophenyl)-4-(6-fluoro-3-pyridyl)-5-methyl-2-imidazolin-2-yl]-3-methoxy-2-pyridone,
1-difluoromethyl-5-[(4R,5S)-4-(4-fluorophenyl)-4-(6-fluoro-3-pyridyl)-5-methyl-2-imidazolin-2-yl]-3-methoxy-2-pyridone,
5-[(5S)-4,4-bis(4-fluorophenyl)-5-methyl-2-imidazolin-2-yl]-1-methoxy-2-pyridone,
1-difluoromethyl-5-[(4S,5S)-4-(6-cyclopropyl-3-pyridyl)-4-(4-fluorophenyl)-5-methyl-2-imidazolin-2-yl]-2-pyridone,
5-[(4S,5S)-4-(6-cyclopropyl-3-pyridyl)-4-(4-fluorophenyl)-5-methyl-2-imidazolin-2-yl]-1-2-pyridone,
5-[(4S,5S)-4-(4-chlorophenyl)-4-(6-fluoro-3-pyridyl)-5-methyl-2-imidazolin-2-yl]-1-methoxy-2-pyridone,
5-[(4S,5S)-4-(6-fluoro-3-pyridyl)-5-methyl-4-(4-trifluoromethylphenyl)-2-imidazolin-2-yl]-1-methoxy-2-pyridone,
5-[(4R,5S)-4-(4-fluorophenyl)-4-(2-fluoro-4-pyridyl)-5-methyl-2-imidazolin-2-yl]-1-methoxy-2-pyridone,
1-cyclopropyl-5-[(4R,5S)-4-(4-fluorophenyl)-4-(6-fluoro-3-pyridyl)-5-methyl-2-imidazolin-2-yl]-2-pyridone,
1-cyclopropyl-5-[(4R,5S)-4-(4-fluorophenyl)-4-(2-fluoro-4-pyridyl)-5-methyl-2-imidazolin-2-yl]-2-pyridone,
1-ethyl-5-[(5S)-4,4-bis(6-fluoro-3-pyridyl)-5-methyl-2-imidazolin-2-yl]-2-pyridone,
5-[(5S)-4,4-bis(6-fluoro-3-pyridyl)-5-methyl-2-imidazolin-2-yl]-1-difluoromethyl-2-pyridone,
1-cyclopropyl-5-[(4S,5S)-4-(4-fluorophenyl)-4-(2-fluoro-4-pyridyl)-5-methyl-2-imidazolin-2-yl]-2-pyridone,
1-difluoromethyl-3-ethyl-5-[(4S,5S)-4-(4-fluorophenyl)-4-(6-fluoro-3-pyridyl)-5-methyl-2-imidazolin-2-yl]-2-pyridone,
1-difluoromethyl-3-ethyl-5-[(4R,5S)-4-(4-fluorophenyl)-4-(6-fluoro-3-pyridyl)-5-methyl-2-imidazolin-2-yl]-2-pyridone,
1-difluoromethoxy-5-[(4S,5S)-4-(4-fluorophenyl)-4-(6-fluoro-3-pyridyl)-5-methyl-2-imidazolin-2-yl]-2-pyridone,
5-[(4R,5S)-4-(6-difluoromethyl-3-pyridyl)-4-(4-fluorophenyl)-5-methyl-2-imidazolin-2-yl]-1-methoxy-2-pyridone,
5-[(4S,5S)-4-(6-difluoromethyl-3-pyridyl)-4-(4-fluorophenyl)-5-methyl-2-imidazolin-2-yl]-1-methoxy-2-pyridone, 1-difluoromethoxy-5-[(4R,5S)-4-(4-fluorophenyl)-4-(6-fluoro-3-pyridyl)-5-methyl-2-imidazolin-2-yl]-2-pyridone, 1-difluoromethyl-3-ethyl-5-[(4R,5S)-4-(4-fluorophenyl)-4-(2-fluoro-4-pyridyl)-5-methyl-2-imidazolin-2-yl]-2-pyridone, 1-difluoromethyl-5-[(4S,5S)-4-(4-fluorophenyl)-4-(6-fluoro-3-pyridyl)-5-methyl-2-imidazolin-2-yl]-3-hydroxy-2-pyridone, 1-difluoromethyl-5-[(4S,5S)-4-(4-fluoro-3-hydroxyphenyl)-4-(6-fluoro-3-pyridyl)-5-methyl-2-imidazolin-2-yl]-2-pyridone, and 1-difluoromethyl-5-[(4S,5R)-4-(4-fluorophenyl)-4-(6-fluoro-3-pyridyl)-5-hydroxymethyl-2-imidazolin-2-yl]-2-pyridone.

10. The compound, or a salt thereof, as claimed in claim 1, wherein the compound is
1-difluoromethyl-5-[(4S,5S)-4-(4-fluorophenyl)-4-(6-fluoro-3-pyridyl)-5-methyl-2-imidazolin-2-yl]-2-pyridone.

11. The compound, or a salt thereof, as claimed in claim 1, wherein the compound is
1-ethyl-5-[(4S,5S)-4-(4-fluorophenyl)-4-(6-fluoro-3-pyridyl)-5-methyl-2-imidazolin-2-yl]-2-pyridone.

12. The compound, or a salt thereof, as claimed in claim 1, wherein the compound is
5-[(4S,5S)-4-(4-fluorophenyl)-4-(6-fluoro-3-pyridyl)-5-methyl-2-imidazolin-2-yl]-2-pyridone.

13. The compound, or a salt thereof, as claimed in claim 1, wherein the compound is
5-[(4S,5S)-4-(4-fluorophenyl)-4-(6-fluoro-3-pyridyl)-5-methyl-2-imidazolin-2-yl]-1-isopropyl-2-pyridone.

14. The compound, or a salt thereof, as claimed in claim 1, wherein the compound is
1-difluoromethyl-5-[(4R,5S)-4-(4-fluorophenyl)-5-methyl-4-(6-trifluoromethyl-3-pyridyl)-2-imidazolin-2-yl]-2-pyridone.

15. The compound, or a salt thereof, as claimed in claim 1, wherein the compound is
1-difluoromethyl-5-[(4S,5S)-4-(4-fluorophenyl)-5-methyl-4-(6-trifluoromethyl-3-pyridyl)-2-imidazolin-2-yl]-2-pyridone.

16. The compound, or a salt thereof, as claimed in claim 1, wherein the compound is
1-ethyl-5-[(4R,5S)-4-(4-fluorophenyl)-5-methyl-4-(6-trifluoromethyl-3-pyridyl)-2-imidazolin-2-yl]-2-pyridone.

17. The compound, or a salt thereof, as claimed in claim 1, wherein the compound is
1-ethyl-5-[(4S,5S)-4-(4-fluorophenyl)-5-methyl-4-(6-trifluoromethyl-3-pyridyl)-2-imidazolin-2-yl]-2-pyridone.

18. The compound, or a salt thereof, as claimed in claim 1, wherein the compound is
5-[(4R,5S)-4-(4-fluorophenyl)-5-methyl-4-(6-trifluoromethyl-3-pyridyl)-2-imidazolin-2-yl]-1-propyl-2-pyridone.

19. The compound, or a salt thereof, as claimed in claim 1, wherein the compound is
5-[(4S,5S)-4-(4-fluorophenyl)-5-methyl-4-(6-trifluoromethyl-3-pyridyl)-2-imidazolin-2-yl]-1-propyl-2-pyridone.

20. The compound, or a salt thereof, as claimed in claim 1, wherein the compound is
3-chloro-1-ethyl-5-[(4R,5S)-4-(4-fluorophenyl)-5-methyl-4-(6-trifluoromethyl-3-pyridyl)-2-imidazolin-2-yl]-2-pyridone.

21. The compound, or a salt thereof, as claimed in claim 1, wherein the compound is
3-chloro-1-ethyl-5-[(4S,5S)-4-(4-fluorophenyl)-5-methyl-4-(6-trifluoromethyl-3-pyridyl)-2-imidazolin-2-yl]-2-pyridone.

22. The compound, or a salt thereof, as claimed in claim 1, wherein the compound is
1-difluoromethyl-5-[(4R,5S)-4-(4-fluorophenyl)-4-(6-fluoro-3-pyridyl)-5-methyl-2-imidazolin-2-yl]-2-pyridone.

23. The compound, or a salt thereof, as claimed in claim 1, wherein the compound is
1-difluoromethyl-5-[(4R,5S)-4-(4-chlorophenyl)-4-(2-fluoro-4-pyridyl)-5-methyl-2-imidazolin-2-yl]-2-pyridone.

24. The compound, or a salt thereof, as claimed in claim 1, wherein the compound is
1-difluoromethyl-5-[(4S,5S)-4-(4-chlorophenyl)-4-(2-fluoro-4-pyridyl)-5-methyl-2-imidazolin-2-yl]-2-pyridone.

25. The compound, or a salt thereof, as claimed in claim 1, wherein the compound is
1-ethyl-5-[(4R,5S)-4-(4-chlorophenyl)-4-(2-fluoro-4-pyridyl)-5-methyl-2-imidazolin-2-yl]-2-pyridone.

26. The compound, or a salt thereof, as claimed in claim 1, wherein the compound is
1-ethyl-5-[(4S,5S)-4-(4-chlorophenyl)-4-(2-fluoro-4-pyridyl)-5-methyl-2-imidazolin-2-yl]-2-pyridone.

27. The compound, or a salt thereof, as claimed in claim 1, wherein the compound is
1-ethyl-3-fluoro-5-[(4S,5S)-4-(4-fluorophenyl)-4-(6-fluoro-3-pyridyl)-5-methyl-2-imidazolin-2-yl]-2-pyridone.

28. The compound, or a salt thereof, as claimed in claim 1, wherein the compound is
1-ethyl-3-fluoro-5-[(4R,5S)-4-(4-fluorophenyl)-5-methyl-4-(6-trifluoromethyl-3-pyridyl)-2-imidazolin-2-yl]-2-pyridone.

29. The compound, or a salt thereof, as claimed in claim 1, wherein the compound is
1-ethyl-3-fluoro-5-[(4S,5S)-4-(4-fluorophenyl)-5-methyl-4-(6-trifluoromethyl-3-pyridyl)-2-imidazolin-2-yl]-2-pyridone.

30. The compound, or a salt thereof, as claimed in claim 1, wherein the compound is
3-ethyl-5-[(4S,5S)-4-(4-fluorophenyl)-4-(6-fluoro-3-pyridyl)-5-methyl-2-imidazolin-2-yl]-1-methyl-2-pyridone.

31. The compound, or a salt thereof, as claimed in claim 1, wherein the compound is
1-difluoromethyl-5-[(4R,5S)-4-(6-difluoromethyl-3-pyridyl)4-(4-fluorophenyl)-5-methyl-2-imidazolin-2-yl]-2-pyridone.

32. The compound, or a salt thereof, as claimed in claim 1, wherein the compound is
1-difluoromethyl-5-[(4S,5S)-4-(6-difluoromethyl-3-pyridyl)-4-(4-fluorophenyl)-5-methyl-2-imidazolin-2-yl]-2-pyridone.

33. The compound, or a salt thereof, as claimed in claim 1, wherein the compound is
5-[(4R,5S)-4-(6-difluoromethyl-3-pyridyl)-4-(4-fluorophenyl)-5-methyl-2-imidazolin-2-yl]-1-ethyl-3-fluoro-2-pyridone.

34. The compound, or a salt thereof, as claimed in claim 1, wherein the compound is 5-[(4S,5S)-4-(6-difluoromethyl-3-pyridyl)-4-(4-fluorophenyl)-5-methyl-2-imidazolin-2-yl]-1-3-fluro-2-pyridone.

35. The compound, or a salt thereof, as claimed in claim 1, wherein the compound is 5-[(4S,5S)-4-(4-fluorophenyl)-4-(6-fluoro-3-pyridyl)-5-methyl-2-imidazolin-2-yl]-1-methoxy-2-pyridone.

36. The compound, or a salt thereof, as claimed in claim 1, wherein the compound is 5-[(4R,5S)-4-(4-fluorophenyl)-5-methyl-4-(6-trifluoromethyl-3-pyridyl)-2-imidazolin-2-yl]-1-methoxy-2-pyridone.

37. The compound, or a salt thereof, as claimed in claim 1, wherein the compound is 1-difluoromethyl-3-ethyl-5-[(4S,5S)-4-(4-fluorophenyl)-4-(6-fluoro-3-pyridyl)-5-methyl-2-imidazolin-2-yl]-2-pyridone.

38. A process for preparing a compound of the formula (I):

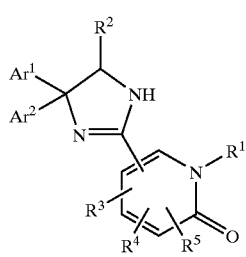

(wherein $Ar^1$ and $Ar^2$ are independently aryl or heteroaryl, any of which is optionally substituted by a substituent selected from the group consisting of cyano, halogen, nitro, lower alkyl, halo-lower alkyl, hydroxy-lower alkyl, cyclo-lower alkyl, cyclo (lower alkyl)-lower alkyl, lower alkenyl, lower alkylamino, di-lower alkylamino, lower alkanoylamino, lower alkylsulfonylamino, arylsulfonylamino, hydroxy, lower alkoxy, halo-lower alkoxy, aryloxy, heteroaryloxy, lower alkylthio, carboxyl, formyl, lower alkanoyl, lower alkoxycarbonyl, carbamoyl, lower alkylcarbamoyl, di-lower alkylcarbamoyl, lower alkylsulfonyl, arylsulfonyl, aryl and heteroaryl;

$R^1$ and $R^2$ are independently lower alkyl, cyclo-lower alkyl, cyclo(lower alkyl)-lower alkyl or lower alkoxy, any of which is optionally substituted by a substituent selected from the group consisting of halogen, lower alkylamino, di-lower alkylamino, lower alkanoylamino, hydroxy, lower alkoxy, formyl, lower alkoxycarbonyl, lower alkylcarbamoyl and di-lower alkylcarbamoyl;

$R^3$, $R^4$ and $R^5$ are independently hydrogen, cyano, halogen or hydroxy, or lower alkyl, lower alkoxy or lower alkylthio, the last three groups being optionally substituted by a substituent selected from the group consisting of halogen, lower alkylamino, di-lower alkylamino, lower alkanoylamino, hydroxy, lower alkoxy, formyl, lower alkoxycarbonyl, lower alkylcarbamoyl and di-lower alkylcarbamoyl), or a salt or ester thereof, which comprises reacting a compound of the formula (II):

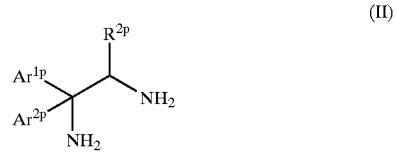

(wherein $Ar^{1p}$ and $Ar^{2p}$ are independently aryl or heteroaryl, any of which is optionally substituted by a substituent selected from the group consisting of cyano, halogen, nitro, lower alkyl, halo-lower alkyl, cyclo-lower alkyl, cyclo (lower alkyl)-lower alkyl, lower alkenyl, di-lower alkylamino, lower alkoxy, halo-lower alkoxy, aryloxy, heteroaryloxy, lower alkylthio, formyl, lower alkanoyl, lower alkoxycarbonyl, di-lower alkylcarbamoyl, lower alkylsulfonyl, arylsulfonyl, aryl, heteroaryl, optionally protected hydroxy-lower alkyl, optionally protected lower alkylamino, optionally protected lower alkanoylamino, optionally protected lower alkylsulfonylamino, optionally protected arylsulfonylamino, optionally protected hydroxy, optionally protected carboxyl, optionally protected carbamoyl and optionally protected lower alkylcarbamoyl;

$R^{2p}$ is lower alkyl, cyclo-lower alkyl, cyclo(lower alkyl)-lower alkyl or lower alkoxy, any of which is optionally substituted by a substituent selected from the group consisting of halogen, di-lower alkylamino, lower alkoxy, formyl, lower alkoxycarbonyl, di-lower alkylcarbamoyl, optionally protected lower alkylamino, optionally protected lower alkanoylamino, optionally protected hydroxy and optionally protected lower alkylcarbamoyl)

with a compound of the formula (III):

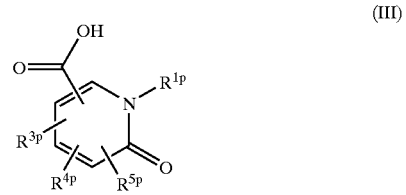

(wherein $R^{1p}$ is lower alkyl, cyclo-lower alkyl, cyclo(lower alkyl)-lower alkyl or lower alkoxy, any of which is optionally substituted by a substituent selected from the group consisting of halogen, di-lower alkylamino, lower alkoxy, formyl, lower alkoxycarbonyl, di-lower alkylcarbamoyl, optionally protected lower alkylamino, optionally protected lower alkanoylamino, optionally protected hydroxy and optionally protected lower alkylcarbamoyl;

$R^{3p}$, $R^{4p}$ and $R^{5p}$ are independently hydrogen, cyano, halogen or optionally protected hydroxy, or lower alkyl, lower alkoxy or lower alkylthio, the last three groups being optionally substituted by a substituent selected from the group consisting of halogen, di-lower alkylamino, lower alkoxy, formyl, lower alkoxycarbonyl, di-lower alkylcarbamoyl, optionally protected lower alkylamino, optionally protected lower alkanoylamino, optionally protected hydroxy and optionally protected lower alkylcarbamoyl), subjecting the resulting compound of the formula (IV):

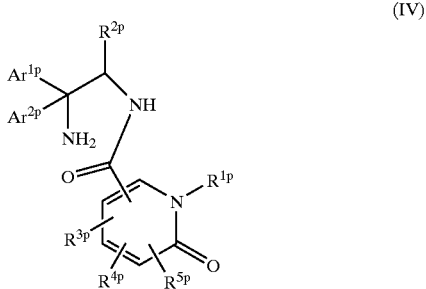

(wherein $Ar^{1p}$, $Ar^{2p}$, $R^{1p}$, $R^{2p}$, $R^{3p}$, $R^{4p}$ and $R^{5p}$ have each the same meaning as defined above) to intramolecular ring closure condensation to give a compound of the formula (V):

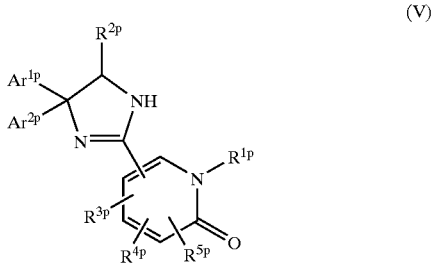

(wherein $Ar^{1p}$, $Ar^{2p}$, $R^{1p}$, $R^{2p}$, $R^{3p}$, $R^{4p}$ and $R^{5p}$ have each the same meaning as defined above), and optionally removing the protecting group(s) from the compound (V).

39. A process for preparing a compound of the formula (I):

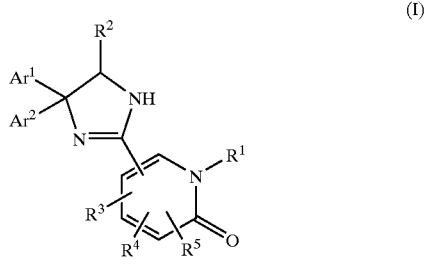

(wherein $Ar^1$ and $Ar^2$ are independently aryl or heteroaryl, any of which is optionally substituted by a substituent selected from the group consisting of cyano, halogen, nitro, lower alkyl, halo-lower alkyl, hydroxy-lower alkyl, cyclo-lower alkyl, cyclo(lower alkyl)-lower alkyl, lower alkenyl, lower alkylamino, di-lower alkylamino, lower alkanoylamino, lower alkylsulfonylamino, arylsulfonylamino, hydroxy, lower alkoxy, halo-lower alkoxy, aryloxy, heteroaryloxy, lower alkylthio, carboxyl, formyl, lower alkanoyl, lower alkoxycarbonyl, carbamoyl, lower alkylcarbamoyl, di-lower alkylcarbamoyl, lower alkylsulfonyl, arylsulfonyl, aryl and heteroaryl;

$R^1$ and $R^2$ are independently lower alkyl, cyclo-lower alkyl, cyclo(lower alkyl)-lower alkyl or lower alkoxy, any of which is optionally substituted by a substituent selected from the group consisting of halogen, lower alkylamino, di-lower alkylamino, lower alkanoylamino, hydroxy, lower alkoxy, formyl, lower alkoxycarbonyl, lower alkylcarbamoyl and di-lower alkylcarbamoyl;

$R^3$, $R^4$ and $R^5$ are independently hydrogen, cyano, halogen or hydroxy, or lower alkyl, lower alkoxy or lower alkylthio, the last three groups being optionally substituted by a substituent selected from the group consisting of halogen, lower alkylamino, di-lower alkylamino, lower alkanoylamino, hydroxy, lower alkoxy, formyl, lower alkoxycarbonyl, lower alkylcarbamoyl and di-lower alkylcarbamoyl), or a salt or ester thereof, which comprises reacting a compound of the formula (II):

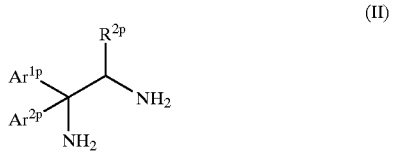

(wherein $Ar^{1p}$ and $Ar^{2p}$ are independently aryl or heteroaryl, any of which is optionally substituted by a substituent selected from the group consisting of cyano, halogen, nitro, lower alkyl, halo-lower alkyl, cyclo-lower alkyl, cyclo (lower alkyl)-lower alkyl, lower alkenyl, di-lower alkylamino, lower alkoxy, halo-lower alkoxy, aryloxy, heteroaryloxy, lower alkylthio, formyl, lower alkanoyl, lower alkoxycarbonyl, di-lower alkylcarbamoyl, lower alkylsulfonyl, arylsulfonyl, aryl, heteroaryl, optionally protected hydroxy-lower alkyl, optionally protected lower alkylamino, optionally protected lower alkanoylamino, optionally protected lower alkylsulfonylamino, optionally protected arylsulfonylamino, optionally protected hydroxy, optionally protected carboxyl, optionally protected carbamoyl and optionally protected lower alkylcarbamoyl;

$R^{2p}$ is lower alkyl, cyclo-lower alkyl, cyclo(lower alkyl)-lower alkyl or lower alkoxy, any of which is optionally substituted by a substituent selected from the group consisting of halogen, di-lower alkylamino, lower alkoxy, formyl, lower alkoxycarbonyl, di-lower alkylcarbamoyl, optionally protected lower alkylamino, optionally protected lower alkanoylamino, optionally protected hydroxy and optionally protected lower alkylcarbamoyl)

with an acid addition salt of a compound of the formula (VI):

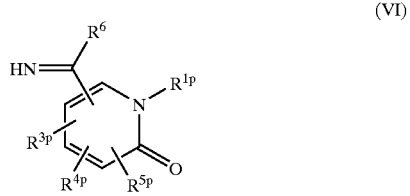

(wherein $R^6$ is amino or lower alkoxy;

$R^{1p}$ is lower alkyl, cyclo-lower alkyl, cyclo(lower alkyl)-lower alkyl or lower alkoxy, any of which is optionally substituted by a substituent selected from the group consisting of halogen, di-lower alkylamino, lower alkoxy, formyl, lower alkoxycarbonyl, di-lower alkylcarbamoyl, optionally protected lower alkylamino, optionally protected lower alkanoylamino, optionally protected hydroxy and optionally protected lower alkylcarbamoyl;

$R^{3p}$, $R^{4p}$ and $R^{5p}$ are independently hydrogen, cyano, halogen or optionally protected hydroxy, or lower alkyl, lower alkoxy or lower alkylthio, the last three groups being optionally substituted by a substituent selected from the group consisting of halogen, di-lower alkylamino, lower alkoxy, formyl, lower alkoxycarbonyl, di-lower alkylcarbamoyl, optionally protected lower alkylamino, optionally protected lower alkanoylamino, optionally protected hydroxy and optionally protected lower alkylcarbamoyl) to give a compound of the formula (V):

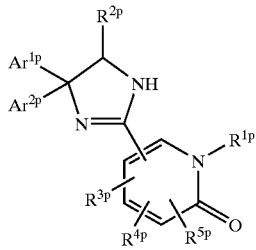

(wherein $Ar^{1p}$, $Ar^{2p}$, $R^{1p}$, $R^{2p}$, $R^{3p}$, $R^{4p}$ and $R^{5p}$ have each the same meaning as defined above), and optionally removing the protecting group(s) from the compound (V).

40. A pharmaceutical composition comprising a compound of the formula (I):

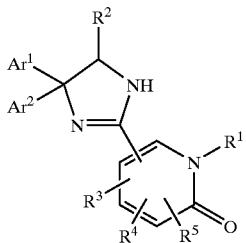

(wherein $Ar^1$ and $Ar^2$ are independently aryl or heteroaryl, any of which is optionally substituted by a substituent selected from the group consisting of cyano, halogen, nitro, lower alkyl, halo-lower alkyl, hydroxy-lower alkyl, cyclo-lower alkyl, cyclo(lower alkyl)-lower alkyl, lower alkenyl, lower alkylamino, di-lower alkylamino, lower alkanoylamino, lower alkylsulfonylamino, arylsulfonylamino, hydroxy, lower alkoxy, halo-lower alkoxy, aryloxy, heteroaryloxy, lower alkylthio, carboxyl, formyl, lower alkanoyl, lower alkoxycarbonyl, carbamoyl, lower alkylcarbamoyl, di-lower alkylcarbamoyl, lower alkylsulfonyl, arylsulfonyl, aryl and heteroaryl;

$R^1$ and $R^2$ are independently lower alkyl, cyclo-lower alkyl, cyclo(lower alkyl)-lower alkyl or lower alkoxy, any of which is optionally substituted by a substituent selected from the group consisting of halogen, lower alkylamino, di-lower alkylamino, lower alkanoylamino, hydroxy, lower alkoxy, formyl, lower alkoxycarbonyl, lower alkylcarbamoyl and di-lower alkylcarbamoyl;

$R^3$, $R^4$ and $R^5$ are independently hydrogen, cyano, halogen or hydroxy, or lower alkyl, lower alkoxy or lower alkylthio, the last three groups being optionally substituted by a substituent selected from the group consisting of halogen, lower alkylamino, di-lower alkylamino, lower alkanoylamino, hydroxy, lower alkoxy, formyl, lower alkoxycarbonyl, lower alkylcarbamoyl and di-lower alkylcarbamoyl), or a salt or ester thereof as an active ingredient, together with a pharmaceutically acceptable additive.

41. A method for the treatment of bulimia, obesity or diabetes, which comprises administering to a patient in need of such treatment a therapeutically effective amount of a compound of the formula (I):

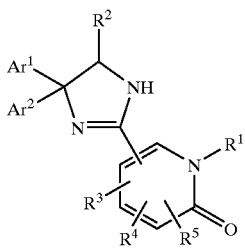

(wherein $Ar^1$ and $Ar^2$ are independently aryl or heteroaryl, any of which is optionally substituted by a substituent selected from the group consisting of cyano, halogen, nitro, lower alkyl, halo-lower alkyl, hydroxy-lower alkyl, cyclo-lower alkyl, cyclo (lower alkyl)-lower alkyl, lower alkenyl, lower alkylamino, di-lower alkylamino, lower alkanoylamino, lower alkylsulfonylamino, arylsulfonylamino, hydroxy, lower alkoxy, halo-lower alkoxy, aryloxy, heteroaryloxy, lower alkylthio, carboxyl, formyl, lower alkanoyl, lower alkoxycarbonyl, carbamoyl, lower alkylcarbamoyl, di-lower alkylcarbamoyl, lower alkylsulfonyl, arylsulfonyl, aryl and heteroaryl;

$R^1$ and $R^2$ are independently lower alkyl, cyclo-lower alkyl, cyclo(lower alkyl)-lower alkyl or lower alkoxy, any of which is optionally substituted by a substituent selected from the group consisting of halogen, lower alkylamino, di-lower alkylamino, lower alkanoylamino, hydroxy, lower alkoxy, formyl, lower alkoxycarbonyl, lower alkylcarbamoyl and di-lower alkylcarbamoyl;

$R^3$, $R^4$ and $R^5$ are independently hydrogen, cyano, halogen or hydroxy, or lower alkyl, lower alkoxy or lower alkylthio, the last three groups being optionally substituted by a substituent selected from the group consisting of halogen, lower alkylamino, di-lower alkylamino, lower alkanoylamino, hydroxy, lower alkoxy, formyl, lower alkoxycarbonyl, lower alkylcarbamoyl and di-lower alkylcarbamoyl), or a salt or ester thereof.

* * * * *